(12) United States Patent
Schwartz et al.

(10) Patent No.: US 12,385,994 B2
(45) Date of Patent: Aug. 12, 2025

(54) SYSTEMS AND METHODS FOR GENERATION OF HYPERPOLARIZED MATERIALS

(71) Applicant: NVISION IMAGING TECHNOLOGIES GMBH, Ulm (DE)

(72) Inventors: Ilai Schwartz, Neu-Ulm (DE); Anna Parker, Ulm (DE); Stephan Knecht, Ulm (DE); Tim Eichhorn, Blaustein (DE); John Blanchard, Ulm (DE)

(73) Assignee: NVision Imaging Technologies GmbH, Ulm (DE)

( * ) Notice: Subject to any disclaimer, the term of this patent is extended or adjusted under 35 U.S.C. 154(b) by 0 days.

(21) Appl. No.: 18/226,960

(22) Filed: Jul. 27, 2023

(65) Prior Publication Data

US 2024/0077552 A1   Mar. 7, 2024

Related U.S. Application Data

(63) Continuation of application No. PCT/IB2022/000032, filed on Jan. 31, 2022.
(Continued)

(51) Int. Cl.
*G01V 3/00* (2006.01)
*A61K 49/10* (2006.01)
(Continued)

(52) U.S. Cl.
CPC .......... *G01R 33/3628* (2013.01); *A61K 49/10* (2013.01); *B01D 11/04* (2013.01)

(58) Field of Classification Search
CPC .............. G01R 33/3628; G01R 33/5601; G01R 33/26; G01R 33/282; G01R 33/62; G01N 24/12; A61K 49/10; B01D 11/04
See application file for complete search history.

(56) References Cited

U.S. PATENT DOCUMENTS

| 2010/0219826 A1* | 9/2010 | Duckett | A61K 49/06 |
| | | | 324/307 |
| 2013/0184565 A1* | 7/2013 | Krummenacker | G01R 33/282 |
| | | | 600/420 |

(Continued)

OTHER PUBLICATIONS

Barskiy et al., "Rapid Catalyst Capture Enables Metal-Free para-Hydrogen-Based Hyperpolarized Contrast Agents", The Journal of Physical Chemistry Letters 2018 9 (11), 2721-2724.
(Continued)

*Primary Examiner* — Thang X Le
(74) *Attorney, Agent, or Firm* — Finnegan, Henderson, Farabow, Garrett & Dunner, LLP

(57) ABSTRACT

Systems and methods are disclosed for increasing a nuclear spin polarization of a target compound. In accordance with such systems and methods, a first non-thermal equilibrium nuclear spin polarization can be imparted to at least one source atom of a source compound, the source atom having a nuclear gyromagnetic ratio of at least 12 megahertz per tesla (MHz/T). A first solution can be obtained that includes the source compound and a target compound. The at least one source atom can be present in a source concentration of at least 0.1 molar (M) in the first solution. A second non-thermal equilibrium nuclear spin polarization of at least 0.01% can be imparted to the at least one target atom of the target compound via a nuclear Overhauser effect (NOE) transfer of the first non-thermal equilibrium nuclear spin polarization to the at least one target atom.

30 Claims, 31 Drawing Sheets

Related U.S. Application Data

(60) Provisional application No. 63/143,794, filed on Jan. 30, 2021, provisional application No. 63/147,263, filed on Feb. 9, 2021, provisional application No. 63/164,675, filed on Mar. 23, 2021, provisional application No. 63/201,153, filed on Apr. 15, 2021, provisional application No. 63/260,174, filed on Aug. 11, 2021, provisional application No. 63/261,152, filed on Sep. 14, 2021.

(51) Int. Cl.
  *B01D 11/04* (2006.01)
  *G01R 33/36* (2006.01)

(56) References Cited

U.S. PATENT DOCUMENTS

| | | | |
|---|---|---|---|
| 2014/0125334 A1* | 5/2014 | Owers-Bradley | G01R 33/282 324/309 |
| 2020/0166592 A1* | 5/2020 | Ibragimova | G01R 33/3808 |
| 2020/0261606 A1* | 8/2020 | Bowers | G01N 24/088 |
| 2020/0386833 A1* | 12/2020 | Breynaert | G01R 33/5605 |

OTHER PUBLICATIONS

Kidd et al. "Facile Removal of Homogeneous SABRE Catalysts for Purifying Hyperpolarized Metronidazole, a Potential Hypoxia Sensor", The Journal of Physical Chemistry C 2018 122 (29), 16848-16852.

Pinon et al., "Hyperpolarized water through dissolution dynamic nuclear polarization with UV-generated radicals", Communications Chemistry, 2020, vol. 3, No. 1, pp. 1-9.

Pinon et al., "Hyperpolarization via dissolution dynamic nuclear polarization: new technological and methodological advances", Magnetic Resonance Materials in Physics, Biology and Medicine, 2020, vol. 34, No. 1, pp. 5-21.

Eichhorn et al., "Hyperpolarized solution-state NMR spectroscopy with optically polarized crystals", arxiv.org, Cornell University Library, 201 Olin Library Cornell University Ithaca, NY 14853, 2021, pp. 1-8.

International Search Report and Written Opinion for European Patent Application No. PCT/IB2022/000032, dated Aug. 12, 2022, 22 pages.

* cited by examiner

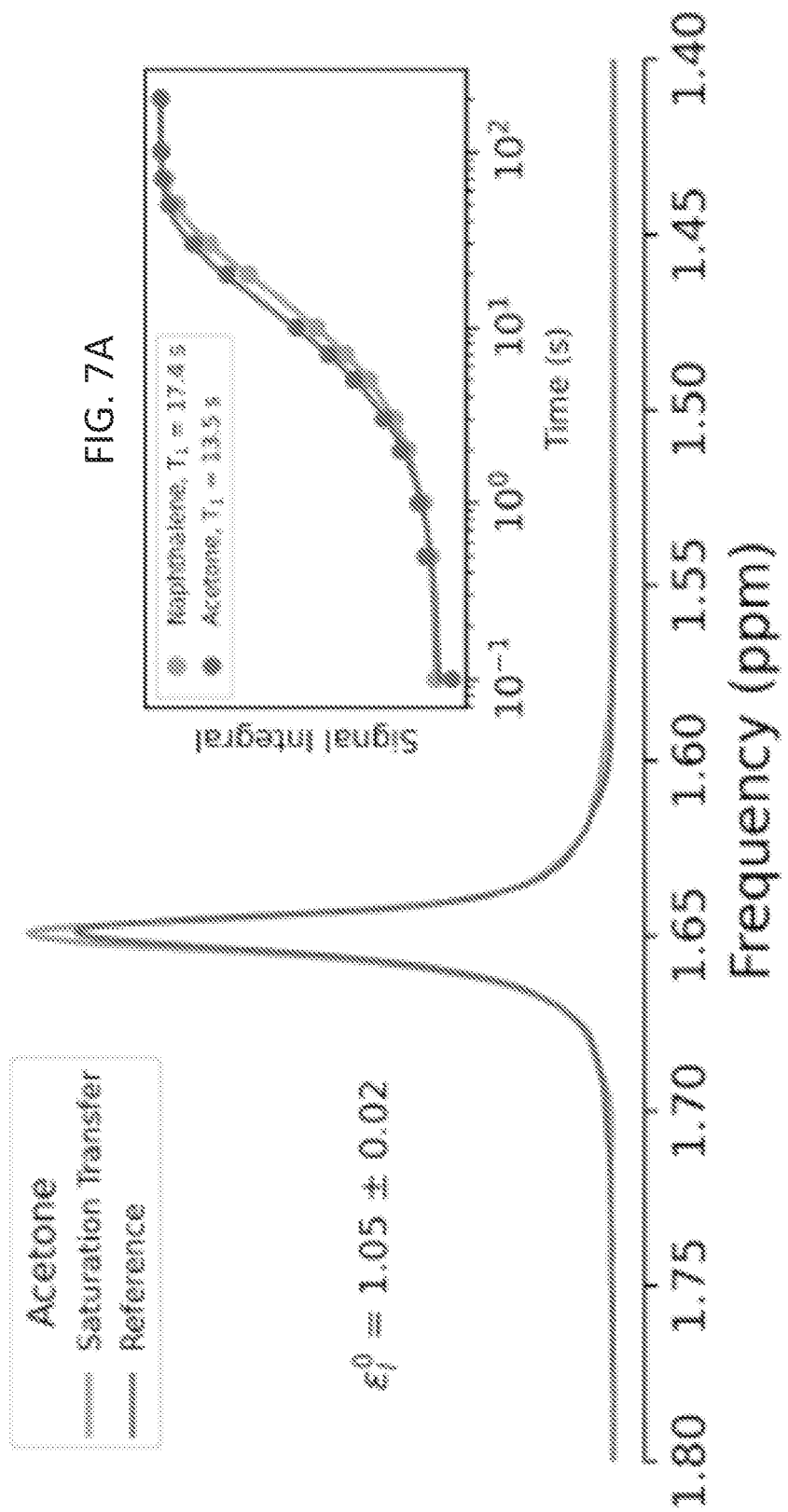

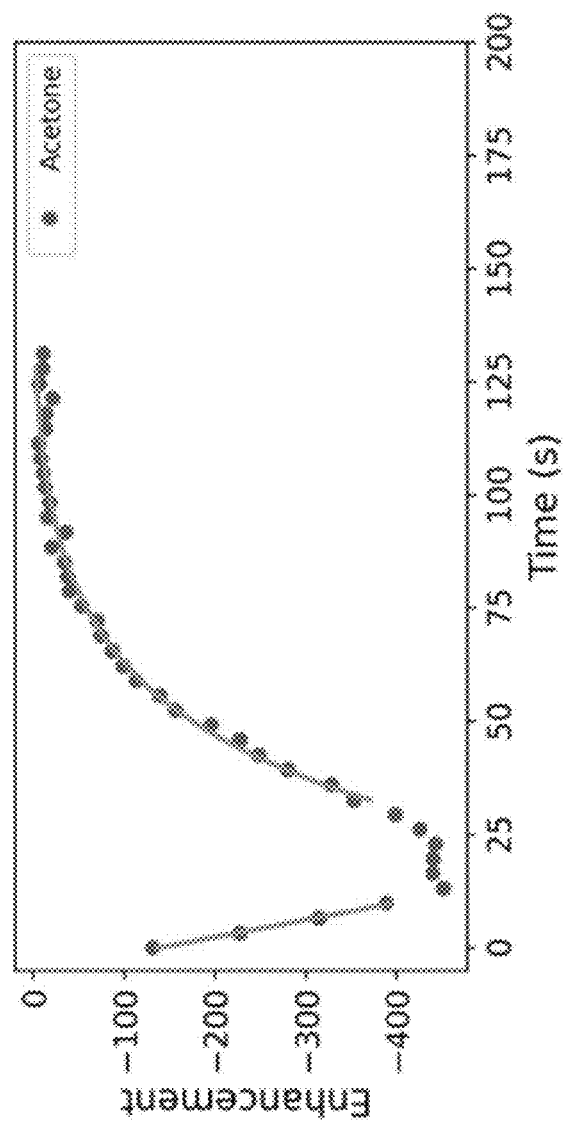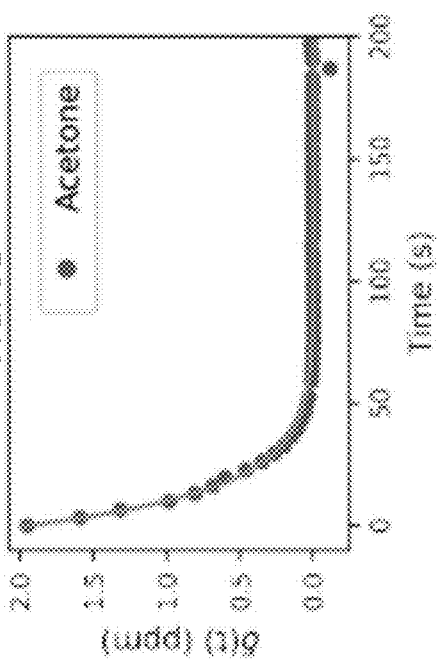

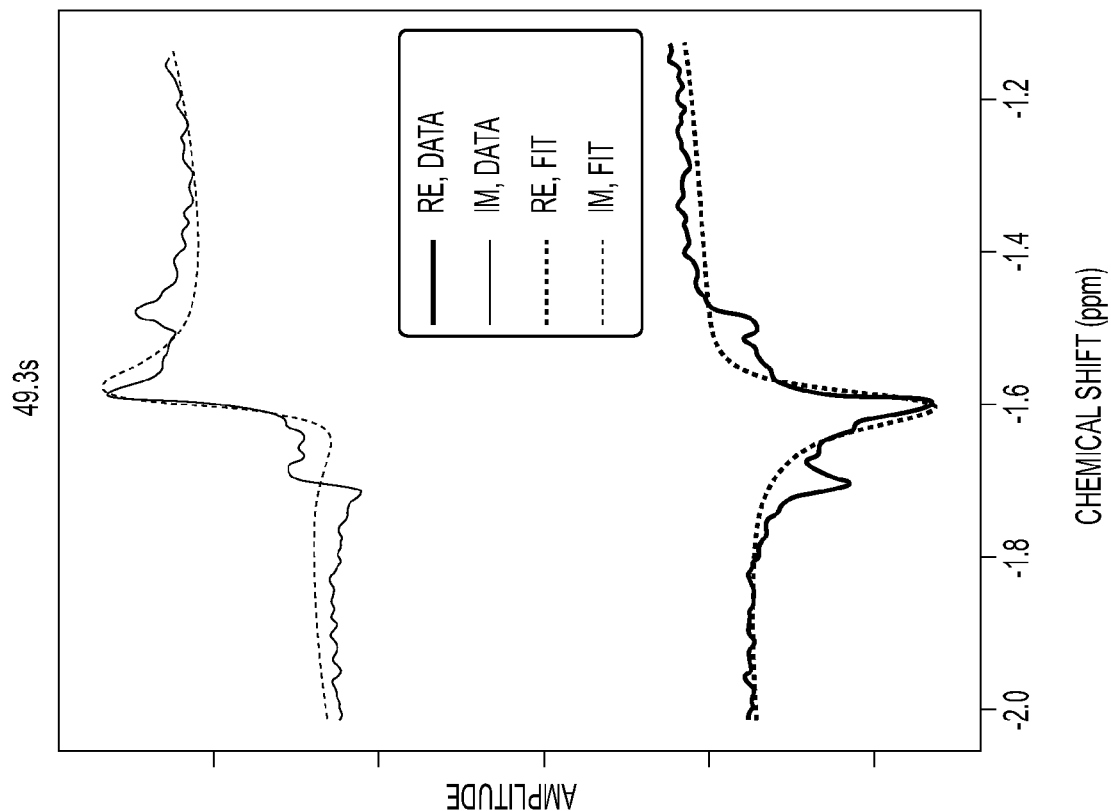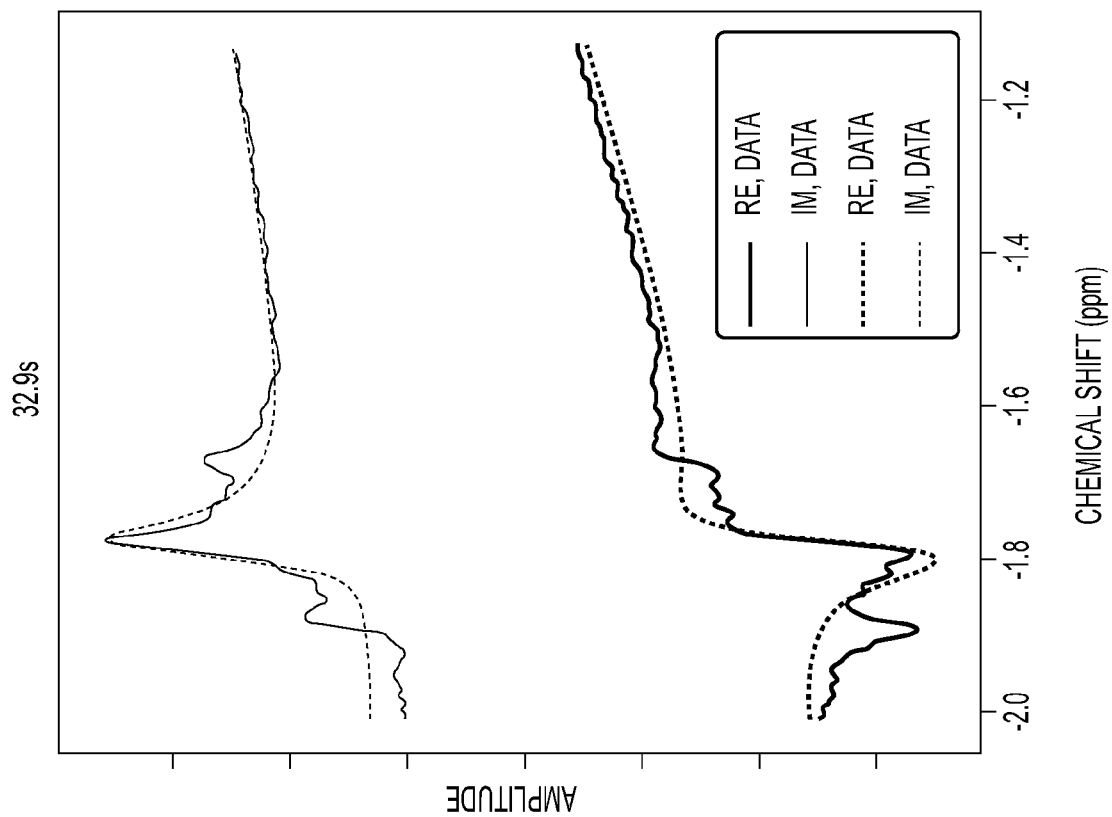
FIG. 10H

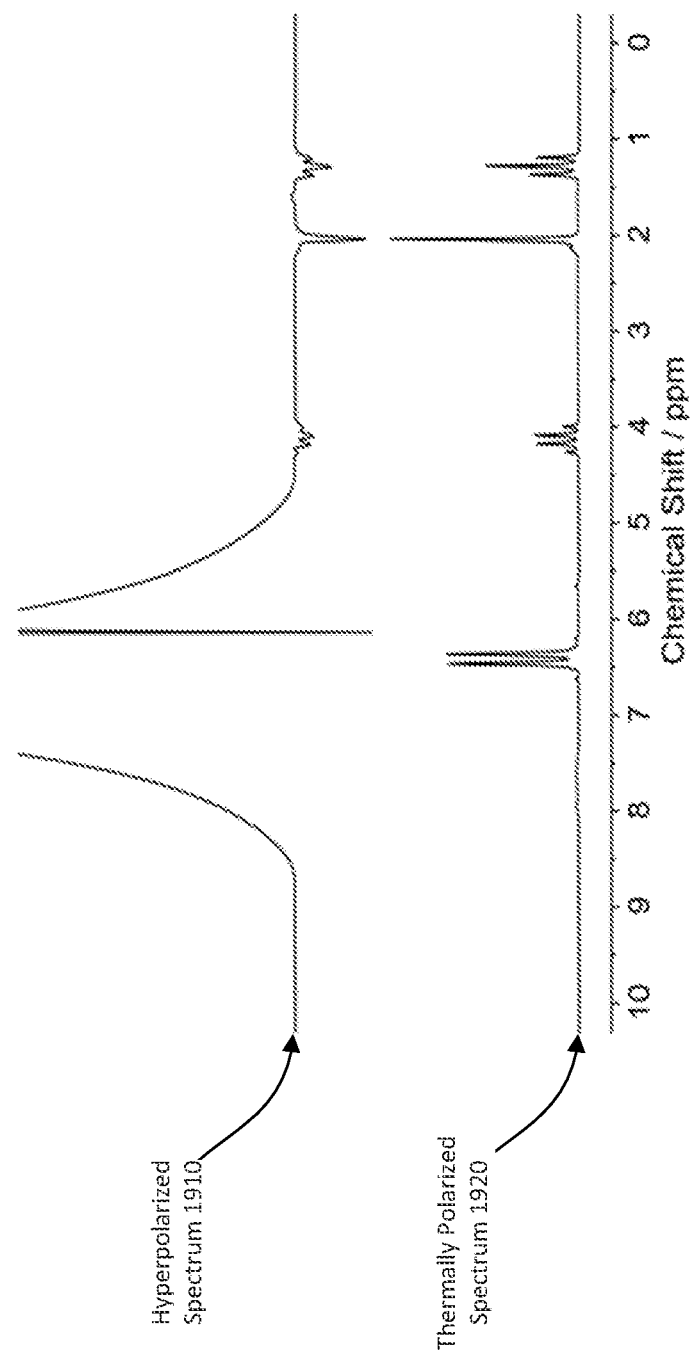

SYSTEMS AND METHODS FOR GENERATION OF HYPERPOLARIZED MATERIALS

CROSS-REFERENCE TO RELATED APPLICATIONS

This application is a continuation of International Application No. PCT/IB2022/000032, filed on Jan. 31, 2022, which claims the benefit of U.S. Provisional Patent Application No. 63/143,794, filed Jan. 30, 2021, U.S. Provisional Patent Application No. 63/147,263, filed Feb. 9, 2021, U.S. Provisional Patent Application No. 63/164,675, filed Mar. 23, 2021, U.S. Provisional Patent Application No. 63/201,153, filed Apr. 15, 2021, U.S. Provisional Patent Application No. 63/260,174, filed Aug. 11, 2021 and U.S. Provisional Patent Application No. 63/261,152, filed Sep. 14, 2021. Each of these applications is incorporated herein by reference in its entirety.

TECHNICAL FIELD

The disclosed embodiments generally relate to generation of hyperpolarized materials for use in nuclear magnetic resonance, magnetic resonance imaging, or similar applications.

BACKGROUND

Nuclear magnetic resonance (NMR) and magnetic resonance imaging (MRI) are technologies with vital applications in chemistry, biology and medical imaging. Despite these successes, it is recognized that nuclear magnetic resonance applications have limitations due to the minute nuclear polarization of analytes (typically on the order of $10^{-5}$). This minute nuclear polarization can result in limited sensitivity in comparison to other analytic techniques such as mass spectrometry.

Increasing nuclear spin polarization beyond its thermal equilibrium value can improve magnetic resonance sensitivity. Nuclear spin polarization can be increased using known techniques like dynamic nuclear polarization. Using such techniques, the nuclear spin polarization of a material can be increased 10,000 times or more. The enhanced nuclear spin polarization can result in a proportional increase in the NMR/MRI signal. While this enhanced polarization decays over time due to the relaxation time of the nuclear spins in the polarized molecules, for many molecules the relaxation time can be on the order of seconds to minutes, during which increased polarization can lead to a dramatic increase in NMR/MRI signal sensitivity. By enabling such a dramatic increase in NMR/MRI signal sensitivity, increased nuclear spin polarization can enable new applications, such as the imaging of in vivo metabolism using metabolites with increased nuclear spin polarization in an MM scanner, accelerate signal NMR spectroscopy investigations, and enable visualization of previously unseen molecular dynamics and structures.

SUMMARY

In accordance with the present disclosure, the intermolecular nuclear Overhauser effect can be used to transfer polarization from a polarized source compound to a target compound. The polarized target compound can then be used in nuclear magnetic resonance (NMR) spectroscopy or magnetic resonance imaging (MM) applications.

The disclosed embodiments include a method for increasing a nuclear spin polarization of a target compound. The method can include an operation of imparting a first non-thermal equilibrium nuclear spin polarization of at least 1% to at least one source atom of a source compound, the source atom having a nuclear gyromagnetic ratio of at least 12 megahertz per tesla (MHz/T). The method can include an operation of obtaining a first solution. The first solution can include the source compound and the target compound. The at least one source atom can be present in a source concentration of at least 0.1 molar (M) in the first solution. The method can include an operation of imparting a second non-thermal equilibrium nuclear spin polarization of at least 0.01% to at least one target atom of the target compound via a nuclear Overhauser effect (NOE) transfer of the first non-thermal equilibrium nuclear spin polarization to the at least one target atom.

The disclosed embodiments include a system for increasing a nuclear spin polarization of a target compound. The system can include a first solution receiving module configured to receive a first solution. The first solution can include a source compound dissolved therein, the source compound comprising at least one source atom, the at least one source non-carbon atom present at a source concentration of at least 0.1 molar (M) in the first solution. The system can include a polarization module coupled to the first solution receiving module, the polarization module configured to impart a first non-thermal equilibrium nuclear spin polarization of at least 1% to the at least one source atom of the source compound. The system can include a second solution receiving module configured to receive a second solution. The second solution can include the target compound dissolved therein. The system can include a mixing module fluidically coupled to the polarization module and to the second solution receiving module, the mixing module configured to mix the first solution and the second solution to thereby permit transfer of the first non-thermal equilibrium nuclear spin polarization to at least one target atom of the target compound via nuclear Overhauser effect (NOE) transfer, thereby imparting a second non-thermal equilibrium nuclear spin polarization of at least 0.01% to the at least one target atom of the target compound.

The disclosed embodiments can include a system for increasing a nuclear spin polarization of a target compound. The system can include a container. The container can include an internal volume configured to house a source compound. The source compound can include at least one PETS moiety. The container can include a first magnetic field source at least partially surrounding the internal volume and configured to generate a first magnetic field within the internal volume. The container can include at least one optical window configured to couple to a light source to thereby permit optical polarization of the at least one PETS moiety. The container can include at least one container port configured to permit passage of the source compound therethrough. The system can include a solution preparation system. The source preparation system can include a dissolution vessel configured to couple to the at least one container port, to receive the source compound following passage of the source compound through the at least one container port, and to receive a pressurized gas and a first solution comprising the compound dissolved therein. The source preparation system can include a second magnetic field source at least partially surrounding the dissolution vessel and configured to generate a second magnetic field within the dissolution vessel. The source preparation system can include a crushing head located within the dissolution vessel and configured to crush the source compound to thereby permit dissolution of the source compound in the first solution to thereby generate a second solution. The source preparation system can include at least one solution port configured to permit passage of the second solution therethrough.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which comprise a part of this specification, illustrate several embodiments and, together with the description, serve to explain the principles and features of the disclosed embodiments. In the drawings:

FIG. 7A depicts the measurement of target thermal $T_1=1/\rho$ relaxation times with a standard non-selective inversion recovery sequence for napathalene and acetone, in accordance with disclosed embodiments.

FIG. 7B depicts the steady-state saturation transfer of naphthalene to acetone, in accordance with disclosed embodiments.

FIG. 9A depicts the polarization buildup and decay for acetone at 1.45 T when the naphthalene source has been optically polarized prior to dissolution in the target solution, in accordance with disclosed embodiments.

FIG. 9B depicts frequency shifts of the resonances for acetone, in accordance with disclosed embodiments.

FIG. 19 depicts a single-shot hyperpolarized spectrum following a 2° flip-angle pulse of propargyl acetate using a PHIP-polarized methyl maleate as a source, compared to a single-shot thermal-equilibrium spectrum of the same mixture acquired following a 90° flip-angle pulse, in accordance with disclosed embodiments.

DETAILED DESCRIPTION

Figure 1:
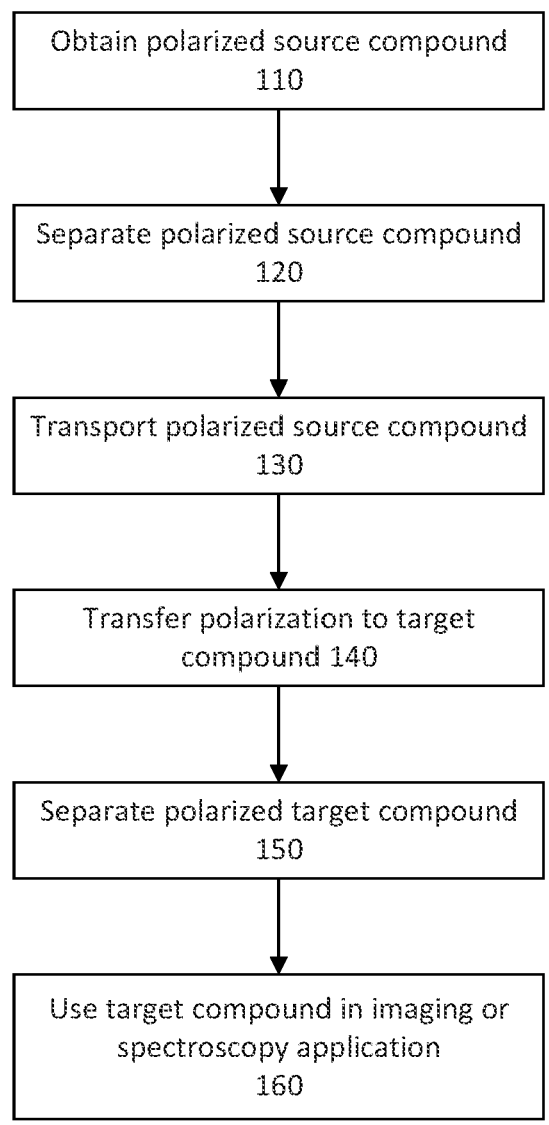
FIG. 1 depicts an exemplary process 100 of preparing and using target compounds in NMR spectroscopy or MM applications, in accordance with disclosed embodiments.

Reference will now be made in detail to exemplary embodiments, discussed with regards to the accompanying drawings. In some instances, the same reference numbers will be used throughout the drawings and the following description to refer to the same or like parts. Unless otherwise defined, technical and/or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

NMR spectroscopy can be used for applications ranging from the determination of chemical structures in synthetic intermediates to the determination of the atomic-level structure and dynamics in proteins and nucleic acids. However, NMR spectroscopy can have limited sensitivity due to a combination of the minute size of nuclear magnetic moments and the correspondingly small polarization at thermal equilibrium. This limited sensitivity can prevent the use of NMR spectroscopy in some application and can render other applications of NMR spectroscopy impractically time- or material-consuming.

NMR sensitivity can be increased through the use of higher magnetic fields and optimized detection systems. However, an alternative approach is to increase NMR sensitivity by increasing nuclear spin polarization to levels significantly greater than thermal equilibrium. Such hyperpolarization techniques may enable new NMR spectroscopy applications, such as observing low-gamma nuclei or low-concentration analytes.

Nuclear spin polarization can be increased using a variety of techniques, including dynamic nuclear polarization (DNP), parahydrogen-induced polarization (PHIP), spin-exchange optical pumping (SEOP), optically initialized electron triplet states (also referred to as photoexcited triplet states (PETS) herein), and other suitable methods. DNP can increase nuclear spin polarization in a wide range of materials but can require equipment capable of generating cryogenic temperatures and high magnetic fields (e.g., as in dissolution dynamic nuclear polarization) or provide only limited signal enhancements (e.g., as in Overhauser DNP). Parahydrogen-induced polarization (PHIP) and spin-exchange optical pumping (SEOP) can produce high polarization levels but only in certain suitable materials.

Polarization via optically initialized electron triplet states (e.g., in organic molecular crystals or in in nitrogen-vacancy (NV) or other defect centers) can produce high polarization levels in certain suitable materials. Such optical polarization methods also benefit from reduce equipment requirements and can produce polarized materials having long relaxation times. Optical polarization methods can produce nuclear-spin polarization in excess of tens of percent at room temperature and low magnetic fields (<1 T). The polarization rate can be controlled by the optical pumping rate. The relaxation time of the nuclear spins following polarization can be exceedingly long, as the paramagnetic electrons may only be present under laser irradiation. For example, $^1$H nuclei in pentacene-doped naphthalene crystals have been polarized to up to 80% polarization, with a lifetime of approximately 50 hours at liquid nitrogen temperatures, long enough to be transported to remote facilities.

Convenient methods of polarization transfer can enable a separation of the originally polarized material (e.g., the source compound) from the material used in NMR spectroscopy (e.g., the target compound). Although referred to as a source compound herein, the originally polarized material may comprise a source molecule or source material. Although referred to herein as a target compound, the material used in NMR spectroscopy may comprise a target molecule or target material. The source compound can then be selected based on the polarization method (e.g., DNP, PHIP, SEOP, optical polarization, or the like); relaxation time, ease of preparation, ease of separability from the target compound, ease of transport, or other technical concerns. The target compound can be selected based on the NMR spectroscopy application of interest. Decoupling the technical requirements of polarization from the technical requirements of NMR spectroscopy can therefore address the technical problem of obtaining high nuclear spin polarization in a suitable target compound.

The disclosed embodiments transfer polarization using the intermolecular nuclear Overhauser effect (NOE). The disclosed embodiments can provide NMR signal enhancements for a range of source and target compounds. The disclosed polarization transfer from source compounds to target compounds can occur on timescales of a few minutes or less and in some embodiments may not require cryogenics. Furthermore, due to an absence of paramagnetic contaminants, target compounds polarized using the disclosed embodiments can be used to generate high-resolution NMR spectra. Unlike conventional polarization-transfer systems, the disclosed embodiments can be automated, can operate at room temperature, and can be used with existing equipment.

As described herein, the disclosed embodiments can be used for polarizing molecules and molecule mixtures. Signal enhancements greater than a factor of 200 and up to a factor of 1730 or more (corresponding to 0.86% polarization or more) can be achieved for the benchmark molecule propargyl acetate at a magnetic field strength of 1.45 T.

"Polarization" can include an imbalance in electron or nuclear spins orientations. In some embodiments, polarization can be the normalized, approximate difference in the number of spins in a first direction minus a number of spins in the opposite direction. As a non-limiting example, given 200,000 $^1$H nuclear spins, a polarization of 2% can correspond to 102,000 spins in the first direction and 98,000 in the opposite direction. In some embodiments, "hyperpolarization" can include polarization of a species (e.g., nuclear, election, or the like) in excess of typical polarization levels for that species observed at thermal equilibrium subject to exposure to a specified magnetic field. As a non-limiting example, a sample in a 1 T magnetic field at thermal equilibrium, with $^1$H nuclear spin polarization in excess of 0.000341% can be hyperpolarized to have a $^1$H nuclear spin polarization substantially higher (e.g., at least one or more orders of magnitude higher) than the 0.000341% thermal equilibrium polarization. As an additional nonlimiting example, a sample in a 3 T magnetic field at thermal equilibrium, with $^{13}$C spin polarization in excess of 0.000257% can be hyperpolarized. As a further nonlimiting example, a sample in an 3 T magnetic field at thermal equilibrium, with $^{15}$N spin polarization in excess of 0.000103% can be hyperpolarized.

A PETS (Photoexcited triplet states) material can contain polarization molecules that, when exposed to suitable optical radiation, have electron spins exceeding 0.1% polarization, 1% polarization, 2% polarization, 3% polarization, 4% polarization, 5% polarization, 6% polarization, 7% polarization, 8% polarization, 9% polarization, 10% polarization, 20% polarization, 30% polarization, 40% polarization, 50% polarization, 60% polarization, 70% polarization, 80% polarization, or more. In some embodiments, the polarizable material can have triplet spin states. In some embodiments, the suitable optical irradiation can induce electron polarization by initial selective population of the triplet spin states. In various embodiments, suitable optical radiation can induce electron polarization through differential decay rates in the triplet spin states. In some embodiments, the suitable optical irradiation can induce electron polarization through a combination of an inversion pulse between triplet states following the optical irradiation and differential decay rates.

In some embodiments, the nuclear spins of a PETS material can be suitable for polarization using spin-polarized electron triplet states of the PETS material. For example, in some embodiments, spin order associated with the spin-polarized electron triplet states of the PETS material can be transferred to nuclei within the PETS material. The spin-polarized photoexcited electron triplet states can provide on-demand electron polarization at a wide range of magnetic fields and temperatures, even combinations where the thermal electron polarization is orders of magnitude below unity. Moreover, the photo-excitable triplet states can have a singlet ground level to which they will decay. Accordingly, whenever the electron is not excited to an excited state, it is not a paramagnetic center and does not cause relaxation. A PETS material can therefore have a nuclear relaxation time at liquid nitrogen temperatures or above, in the absence of optical irradiation, of over an hour, 2 hours, 5 hours, 10 hours, 20 hours, 50 hours, or more. In some embodiments, a PETS material can include a combination of a polarizable material and a host material. The host material may be, for example naphthalene.

A "porous" material can be a material including voids. In some embodiments, a ratio between the surface area of the voids in a quantity of a porous material and the surface area of the quantity of the porous material can be greater than 1, 10, 100, 1000, 10000, or 10000. Accessible voids are void space accessible from the enveloping surface of a quantity of the porous material (e.g., open cells as opposed to closed cells).

A "microparticle" can be a particle that is smaller than 1000 micrometers (μm), 500 μm, 200 μm, 100 μm, 50 μm, 20 μm, 10 μm, 5 μm, 2 μm, or 1 μm in at least one dimension (e.g., smaller than 200 μm in two or three dimensions). In some embodiments, a microparticle can be globular. In various embodiments, a microparticle can have a single dimension significantly greater than the other dimensions. For example, in some embodiments, a microparticle can be rod- or fiber-shaped. In such embodiments, the length of rod- or fiber-like microparticle can be between smaller than 1000 μm, 500 μm, 200 μm, 100 μm, 50 μm, 20 μm, 10 μm, 5 μm, 2 μm, or 1 μm. Similarly, a "nanoparticle" can be a particle that is smaller than 1000 nanometers (nm), 500 nm, 200 nm, 100 nm, 50 nm, 20 nm, 10 nm, 5 nm, 2 nm, or 1 nm in at least one dimension (e.g., smaller than 200 nm in two or three dimensions). In some embodiments, a nanoparticle can be globular. In various embodiments, a nanoparticle can have a single dimension significantly greater than the other dimensions. For example, in some embodiments, a nanoparticle can be rod- or fiber-shaped. In such embodiments, the length of a rod- or fiber-like nanoparticle can be between smaller than 1000 nm, 500 nm, 200 nm, 100 nm, 50 nm, 20 nm, 10 nm, 5 nm, 2 nm, or 1 nm. In some embodiments, micro- or nano-particles may be packed tightly, thereby creating a semi-polycrystalline structure. As used herein, unless otherwise specified, a "particle" can be a nanoparticle or microparticle. The semi-polycrystalline structure can be porous, with accessible voids.

Overview

FIG. 1 depicts an exemplary process 100 of preparing and using target compounds in NMR spectroscopy and MM applications, in accordance with disclosed embodiments. Process 100 decouples the initial polarization of a source compound from the polarization of the target compound used in the NMR spectroscopy or MRI application. Instead, the source compound is polarized and then the polarization is transferred to the target compound. Process 100 can optionally include transporting the polarized source compound and separating the polarized target compound from the source compound prior to using the target compound in the spectroscopy or imaging application. Process 100 can enable greater flexibility in selecting polarization methods, source materials, target materials, and polarization locations. Process 100 can therefore enable generation of more highly polarized target materials, improving NMR spectroscopy or MRI by increasing NMR or MRI sensitivity.

In step 110 of process 100, a polarized source compound can be obtained. In some implementations, obtaining the source compound can include creating the source compound. Consistent with disclosed embodiments, obtaining the polarized source compound can include placing the source compound in a solution. In some embodiments, the source compound can be present in the solution in a source compound concentration of at least 0.01 molar (M), 0.02 M, 0.05 M, at least 0.1 M, at least 0.2 M, at least 0.5 M, 1 M, at least 2 M, at least 5 M, or at least 10 M. The concentration of the source compound can be selected to enable substantial polarization of the source compound. In some embodiments, the source compound can include at least one source atom. In some embodiments, the source atom can be present in the solution in a source atom concentration of at least 0.01 M, 0.02 M, 0.05 M, 0.1 M, at least 0.2 M, at least 0.5 M, at least 1 M, at least 2 M, at least 5 M, or at least 10 M. Polarizing the source compound, in step 110, can include polarizing the at least one source atom. In some embodiments, the ability to transfer polarization between a source atom and a target atom by NOE can depend on the gyromagnetic ratio of the source atom, with higher gyromagnetic ratios enhancing polarization transfer. In such embodiments, the source atom can have a gyromagnetic ratio of at least 12 megahertz per Tesla (MHz/T), at least 14 MHz/T, at least 16 MHz/T, at least 18 MHz/T, at least 20 MHz/T, at least 22 MHz/T, at least 24 MHz/T, at least 26 MHz/T, at least 28 MHz/T, at least 30 MHz/T, at least 32 MHz/T, at least 34 MHz/T, at least 36 MHz/T, at least 38 MHz/T, at least 40 MHz/T, at least 42 MHz/T, or at least 44 MHz/T. For example, a source atom can be a hydrogen atom (e.g., 42.58 MHz/T gyromagnetic ratio), tritium atom (e.g., 45.42 MHz/T gyromagnetic ratio), fluorine-19 atom (e.g., 40.08 MHz/T gyromagnetic ratio), phosphorous-31 atom (e.g., 17.25 MHz/T gyromagnetic ratio), or the like.

In some embodiments, the source compound can be a molecule and the source atom can be part of that molecule. For example, when the source compound is naphthalene then the source atom can be $^1$H. As an additional example, when the source compound is fluorostyrene then the source atom can be $^{19}$F. As a further example, when the source compound is Triphenylphosphine then the source atom can be $^{31}$P. In various embodiments, the source compound can be a combination of molecules and the source atom can be part of one of these molecules. For example, the source compound can be a crystalline host, which can include a dopant molecule. The source atom can be part of the dopant molecule. In some embodiments, the crystalline host can be or include naphthalene, p-terphenyl, or benzoic acid. In various embodiments, the dopant can be or include pentacene.

In some embodiments, the solution can be an organic solution. In some embodiments the organic solution is a common organic solution used in NMR spectroscopy such as acetone, chloroform, DMSO, toluene, ethyl acetate, benzene, methanol, ethanol, other short alcohols, or deuterated version thereof. In some embodiments the solution is an aqueous solution. In some embodiments, the solution can be selected such that the source compound is at least partially soluble in the solution. For example, when the source compound is naphthalene, the solution can be deuterated acetone, DMSO, methanol or chloroform.

Consistent with disclosed embodiments, obtaining the polarized source compound can include polarizing the source compound. The disclosed embodiments are not limited to a particular method of polarizing the source compound. In some embodiments, the source compound can be polarized using dynamic nuclear polarization (DNP), optical polarization, parahydrogen-induced polarization (PHIP) or parahydrogen-induced polarization by side arm hydrogenation (PHIP-SAH), Signal Amplification by Reversible Exchange (SABRE), or another suitable method.

Consistent with disclosed embodiments, the source compound can be polarized using DNP at low temperatures and high magnetic fields. In some implementations, the free electron spins in radicals or paramagnetic defects in the source compound can be highly polarized at thermodynamic equilibrium at temperatures below 4K and magnetic fields above 1 T. Using DNP protocols, this high thermal polarization of the electrons can be transferred to nuclear spins in the source compound. In some embodiments, following polarization, the compound can be dissolved in a solution as done in dissolution DNP.

Figure 5:
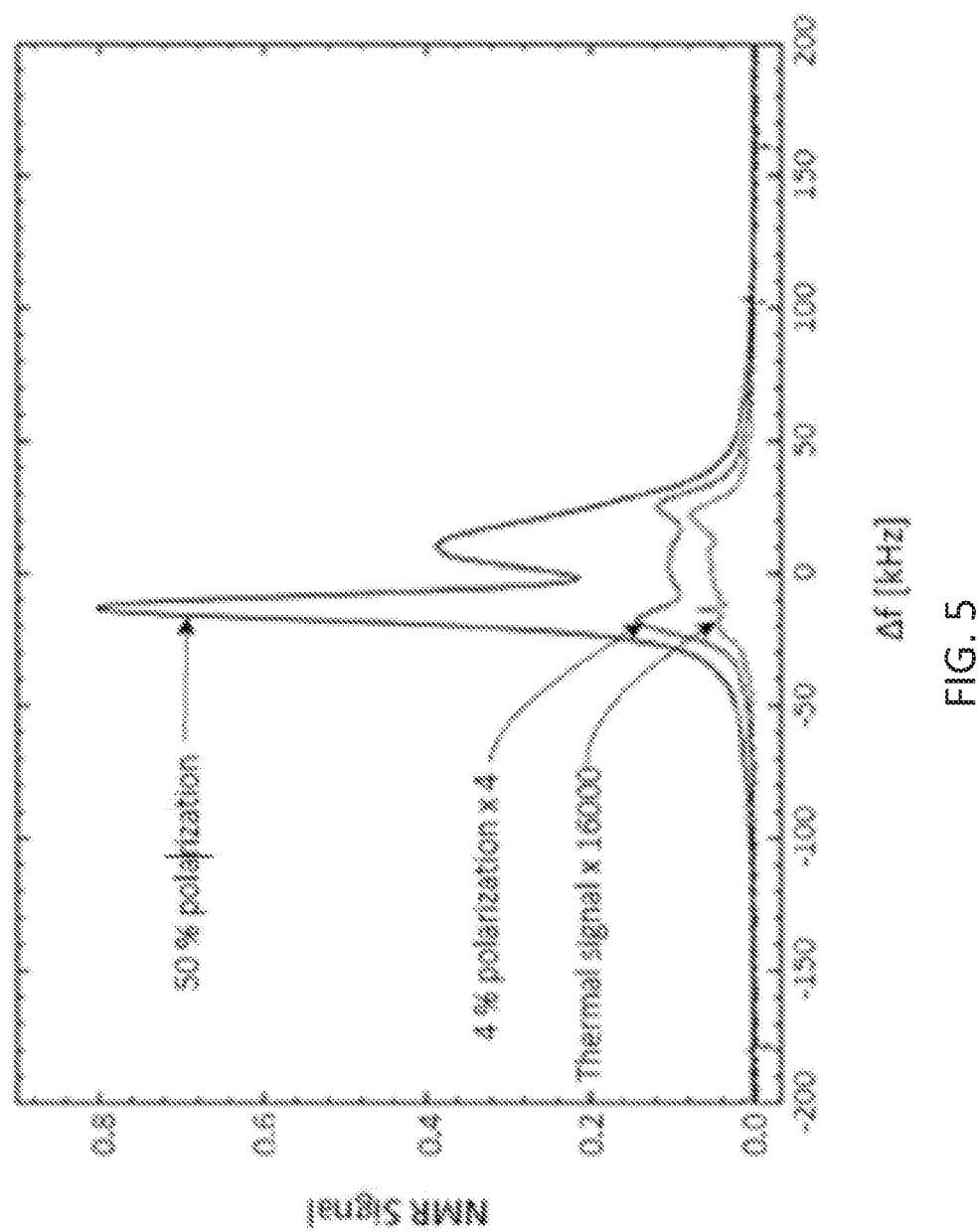
FIG. 5 depicts NMR signal reads from a compound before and after repeated iterations of the polarization sequence depicted in FIG. 4, in accordance with disclosed embodiments.
Figure 6:
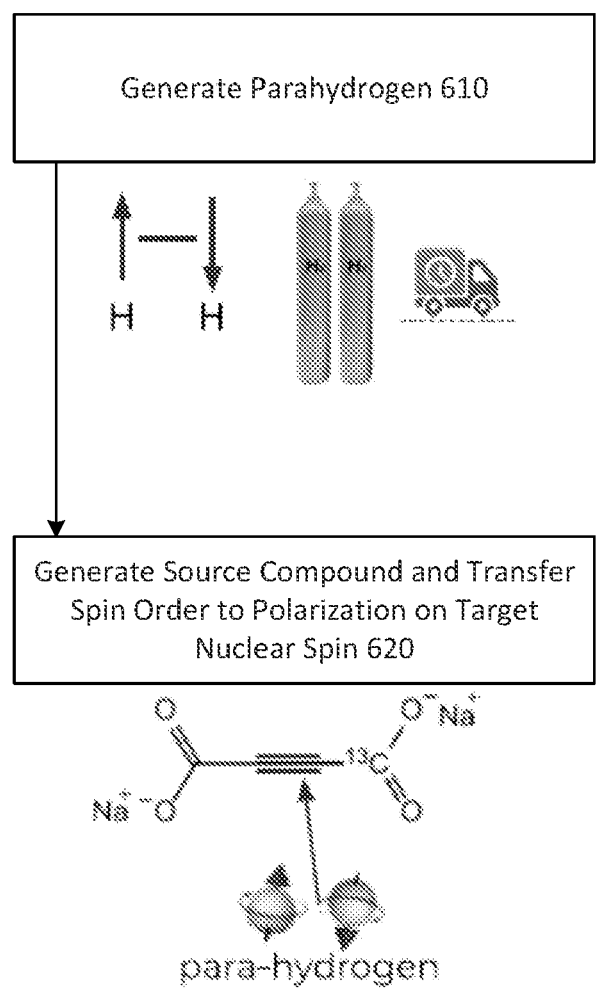
FIG. 6 depicts an exemplary parahydrogen induced polarization (PHIP) precipitation transfer process, in accordance with disclosed embodiments.

Consistent with disclosed embodiments, the source compound can be polarized optically. In some embodiments, optical polarization can use optical defects such as color centers. In such methods, optically active defects in semiconductors such as diamond and silicon carbide can be used to polarize surrounding nuclear spins. In various embodiments, optical polarization can hyperpolarize the nuclear spins in a PETS compound by polarization transfer from optically polarizable electron spins in the PETS polarization molecules to the nuclear spins. FIGS. 2 through 5 depict generation of a polarized source compound using optically initialized electron triplet states, Consistent with disclosed embodiments, the source compound can be polarized using PHIP, PHIP-SAH, or SABRE. Parahydrogen, orthodeuterium, or paratritum can be used to induce electron spin order in the source compound, which can be converted to nuclear spin polarization (e.g., through the application of suitable RF pulse sequences, or the like). In SABRE embodiments, a catalyst can bind the source compound and the parahydrogen, orthodeuterium, or paratritum. The source compound can be polarized while bound to the catalyst. In PHIP or PHIP-SAH embodiments, a precursor compound can be hydrogenated (e.g., using parahydrogen, orthodeuterium, or paratritum) to form a parahydrogenated, orthodeuterated, or paratritiated precursor, respectively. In PHIP embodiments, the hydrogenated precursor can be polarized to form the source compound, while PHIP-SAH embodiments, the hydrogenated precursor can be polarized and the side arm cleaved to form the source compound. In some embodiments, hydrogenation catalysts and/or reaction byproducts can be separated from the source compound. In some embodiments, the source compound can be precipitated or solidified. FIG. 6 depicts generation of a polarized source compound using PHIP.

In some embodiments, polarizing the source compound can include hyperpolarizing the at least one source atom of the source compound. As described herein, such hyperpolarization can include increasing the polarization levels of the at least one source atom above the level observed at thermal equilibrium. In some embodiments, the non-thermal equilibrium polarization imparted to the at least one source atom can exceed at least 1%. In various embodiments, the non-thermal equilibrium polarization imparted to the at least one source atom can exceed at least 2%, 5%, 10%, 20%, or 50%.

In optional step 120, when the source compound is polarized in solution (e.g., when the source compound is polarized using PHIP, PHIP-SAH, or SABRE), the source compound can be extracted from the solution, or undesired solutes can be removed from the solution. Such undesired solutes can include hydrogenation catalysts and reaction byproducts. The disclosed embodiments are not limited to any particular method of separating the source compound. In some embodiments, during the separation the concentration of the compound is increased. In some embodiments the separation is performed by liquid-liquid separation. In various embodiments, the source compound (or the undesired solutes) can be extracted from the solution by precipitation or solidification. Such precipitation or solidification can be induced reducing the solubility of the source compound in the solution. In some embodiments, the solution can be modified (e.g., by changing solution pH, temperature, adding other solvents or solutes, or the like). In various embodiments, application of an electromagnetic stimulus (e.g., optical radiation, such as ultraviolet radiation or optical radiation at another suitable wavelength or wavelengths) or mechanical stimulus (e.g., ultrasound, agitation, or another suitable mechanical stimulus), addition of another solute or solvent to the solution, or another suitable method. In some embodiments, a precursor molecule to the source compound can be modified. For example, a sidearm of the precursor molecule can be cleaved to form the source compound. The source compound can be less soluble in the solution than the precursor, causing the source compound to precipitate. In some embodiments, following precipitation, the precipitated source compound can be separated from the solution (e.g., using a filter, centrifuge, or another suitable method).

In optional step 130 of process 100, the polarized source compound can be transported. In some embodiments, the polarized source compound can be produced in a facility remote from the facility in which the NMR spectroscopy is preformed. For example, the polarized source compound can be produced in a facility dedicated to the production of the polarized source compound, while the NMR spectroscopy is performed at one of many facilities that require polarized target compounds. In this manner, efficiencies of scale can be realized in the production of the source compound. In some embodiments, the polarized source compound can be transported for a period of time in excess of 30 minutes, or an hour, or 2 hours, or 5 hours, or 10 hours, or more. The polarized source compound can be transporting in a cryogenic container. The polarized source compound can be subjected to a predetermined magnetic field during transport. In some embodiments, the predetermined magnetic field can be greater than the magnetic field of the Earth. FIG. 9 depicts an exemplary container for transporting the polarized source compound.

In step 130 of process 100, polarization can be transferred to a target compound. As a preliminary to polarization transfer, the target compound and the source compound can be combined. In some embodiments, the source compound can be combined in solid form. A solid source compound can be combined with a solid target compound. The combined compound can then be mixed into a solution. A solid source compound can be redissolved in a solution. This solution can contain the target compound, or the target compound can be subsequently added.

As may be appreciated, precipitating and redissolving the source compound can enable separate tuning of the solution in which the source compound is polarized (the first solution) and the solution in which polarization transfer occurs (the second solution). Characteristics of the first solution (e.g., biocompatibility, concentration, volume, temperature, pH, polarity, or other relevant characteristics) can differ from such characteristics of the second solution. For example, the concentrations of the source compound in the original solution and subsequent solution can differ. A lower concentration of the source compound in the original solution of step 110 can enable greater polarization of the source compound. A higher concentration of the source compound in the subsequent solution of step 140 can enable greater polarization transfer from the source compound to the target compound.

In some embodiments, source compound or the target compound can remain solid, semi-solid, or in suspension in the solution. For example, the source compound or the target compound can be incorporated in a surface, solid, membrane, nanoparticle, or microparticle. In such embodiments, polarization of the target atom can then occur by cross-relaxation at a liquid-solid interface.

In some embodiments, the source compound can be combined while in solution. In such embodiments, optional step 120 may not be performed. The source compound can remain in the solution of step 110. The target compound can be dissolved into the source compound solution, or a solution including the target compound can be added to the source compound solution.

In some embodiments, the target compound can be or include a small molecule (e.g., a molecule having a molecular weight of less than 1000 daltons, 900 daltons, 800 daltons, 700 daltons, 600 daltons, 500 daltons, 400 daltons, 300 daltons, 200 daltons, or 100 daltons), a peptide, a polypeptide, a protein, a nucleic acid, a ribonucleic acid, a deoxyribonucleic acid, a carbohydrate, a polymer, or another suitable target compound. In some embodiments the target compound can be particles suspended in a solution or particles impregnated with a solution. In some embodiments the target compound can be a surface of a solid or thin material in contact with a solution. In some embodiments the target compound can be an amorphous structure in contact with a solution such as a gel, membrane, polymer or porous material. Transferring the polarization to the target compound can include transferring polarization from the at least one source atom of the source compound to nuclear spin polarization of at least one target atom of the target compound. The target atom can be selected based on the intended NMR spectroscopy application. In some embodiments, the target atom can be hydrogen, tritium, carbon-13, nitrogen-15, fluorine-19, silicon-29, phosphorous-31, iron-57, selenium-77, yttrium-89, rhodium-103, silver-107, silver-109, cadmium-111, cadmium-113, tin-117, tin-119, tellurium-123, tellurium-125, thullium-169, ytterbium-171, tungsten-183, osmium-187, platinum-195, mercury-199, thallium-203, thallium-205, lead-207, polonium-209, or plutonium-239. In some embodiments, the target atom can have a nuclear spin of ½. In other embodiments the target atom can have a nuclear spin of one or more.

In some embodiments, the ability to transfer polarization from a source atom to nuclear spin polarization of the target atom can depend on an electron cloud size of the target atom (e.g., with lower electron cloud size improving the ability to transfer polarization by reducing the minimum distance to other molecules) and the gyromagnetic ratio of the target atom (e.g., with increasing gyromagnetic ratios improving the ability to transfer polarization). In some embodiments, the target atom can have a gyromagnetic ratio greater than at least 2 MHz/T, at least 4 MHz/T, at least 6 MHz/T, at least 8 MHz/T, at least 10 MHz/T, at least 12 MHz/T, at least 14 MHz/T, at least 16 MHz/T, at least 18 MHz/T, at least 20 MHz/T, at least 22 MHz/T, at least 24 MHz/T, at least 26 MHz/T, at least 28 MHz/T, at least 30 MHz/T, at least 32 MHz/T, at least 34 MHz/T, at least 36 MHz/T, at least 38 MHz/T, at least 40 MHz/T, at least 42 MHz/T, or at least 44 MHz/T, at most 44 MHz/T, at most 42 MHz/T, at most 40 MHz/T, at most 38 MHz/T, at most 36 MHz/T, at most 34 MHz/T, at most 32 MHz/T, at most 30 MHz/T, at most 28 MHz/T, at most 26 MHz/T, at most 24 MHz/T, at most 22 MHz/T, at most 20 MHz/T, at most 18 MHz/T, at most 16 MHz/T, at most 14 MHz/T, at most 12 MHz/T, at most 10 MHz/T, at most 8 MHz/T, at most 6 MHz/T, at most 4 MHz/T, at most 2 MHz/T, or within a range defined by any two of the preceding values.

In some embodiments, the target compound can be a molecule and the target atom can be part of that molecule. For example, when the target compound is a metabolite then the target atom can be $^{1}H$, $^{13}C$, $^{15}N$. As an additional example, when the target compound is silicate then the target atom can be $^{29}Si$. In various embodiments, the target compound can be a combination of molecules and the target atom can be part of one of these molecules.

Consistent with disclosed embodiments, polarization can be transferred using SPINOE. A nuclear spin on a target atom can polarized by cross-relaxation from a polarized source atom. In some embodiments, a source compound containing the source atom can be in solution with a target compound containing the target atom. In some embodiments, a concentration of the target compound in the solution can be less than 1,000 millimolar (mM), 500 mM, 200 mM, 100 mM, 50 mM, 20 mM, 10 mM, 5 mM, 2 mM, 1 mM, 500 micromolar (04), 200 µM, 100 µM, 50 µM, 20 µM, 10 µM, 5 µM, 2 µM, 1 µM, 500 nanomolar (nM), 200 nM, 100 nM, 50 nM, 20 nM, 10 nM, 5 nM, 2 nM, 1 nM, or less in the first solution.

In some embodiments, the at least one target atom can be hyperpolarized through polarization transfer. As described herein, such hyperpolarization can include increasing the polarization levels of the at least one target atom above a thermal equilibrium polarization level observed at thermal equilibrium. In some embodiments, a non-thermal equilibrium polarization of at least 0.01% can be imparted through polarization transfer to the at least one target atom. In various embodiments, the non-thermal equilibrium polarization imparted to the at least one target atom can exceed at least 0.02%, 0.05%, 0.1%, 0.2%, 0.5%, 1%, 2%, 5%, or 10%.

In optional step 140 of process 100, the target compound can be separated from the source compound. The disclosed embodiments are not limited to any particular method of separating the target compound from the source compound. In some embodiments, the target compound can be separated from the source compound using liquid-liquid separation. The target compound and the source compound can be selected such that a polarity of the target compound differs from a polarity of the source compound (e.g., a polar target compound and a non-polar source compound). In some embodiments, a solution of the source compound, the target compound, and a first solvent can be combined with a second solvent. For example, when the target compound and source compound are mixed in a cavity, the second solvent can be introduced into the cavity. The source compound can be more soluble in the first solvent, while the target compound can be more soluble in the second solvent. In some embodiments, the first and second solvents can be immiscible. The first solvent can be separated from the second solvent to separate the target compound from the source compound. For example, the source compound can be selected to preferentially dissolve in an organic solvent and the target compound can be selected to preferentially dissolve in an aqueous solvent (or vice versa). Separation of the target compound from the source compound can then be performed by separating the aqueous solution from the organic solution.

In various embodiments, the target compound can be crystalized or precipitated out of the solution. The disclosed embodiments are not limited to any particular method of inducing such precipitation. For example, such precipitation can be induced by through a change in temperature or pH, application of an electromagnetic stimulus (e.g., optical radiation, such as ultraviolet radiation or optical radiation at another suitable wavelength or wavelengths), mechanical stimulus (e.g., ultrasound, agitation, or another suitable mechanical stimulus), addition of another solute or solvent to the solution, or another suitable method, or any combination thereof. In some embodiments, following precipitation, the target compound can be separated from the solution (e.g., using a filter, or another suitable method). In some embodiments, the target compound may then be combined or redissolved into another solution. This second solution may have desirable characteristics (e.g., biocompatibility, concentration, volume, temperature, pH, polarity, or other relevant characteristics, or any combination thereof) for the intended imaging application.

In step 150 of process 100, the target compound can be used in an imaging or spectroscopy application. In some embodiments, at least a portion of the target compound can be injected into a subject or patient. In various embodiments, at least a portion of the target compound can be used in NMR spectroscopy. During performance of step 150, at least one NMR or MRI pulse sequence can be applied to the target compound. In some embodiments, the signal from the source molecules is reduced by at least 50%, 60%, 70%, 80%, 90%, 95%, or 99% in the spectroscopy application. In some embodiments the source polarization is reduced before the detection scheme. In some embodiments a pulse sequence which reduces the transverse oscillating signal of the source molecule compared to the target molecules is utilized. In some embodiments a signal post-processing scheme is applied to the signal reduce the effects of the highly polarized source molecule, including removing signal from the source molecule, improving the phase and the frequency of the target molecules to best match their phase and frequency without the effect of the highly polarized source molecule. In some embodiments, the at least one NMR or MM pulse sequence can include at least one radiation-damping procedure configured to reduce radiation damping of the target compound by at least 50%, 60%, 70%, 80%, 90%, 95%, or 99% compared to a pulse sequence that does not utilize the at least one radiation-damping procedure. Such a radiation-damping procedure can include at least one Q-switching procedure or at least one detuning procedure. The at least one Q-switching procedure or the at least one detuning procedure can be applied to an induction coil configured to receive an NMR signal or an MRI signal from the target compound. In some embodiments, the at least one Q-switching procedure or the at least one detuning procedure comprises modifying a quality (Q) factor of the induction coil from: (i) a first value of at least 100, at least 50, at least 20, or at least 10 during application of a hard excitation pulse to the molecule to (ii) a second value of at most 1, at most 0.5, at most 0.2, or at most 0.1 during application of a frequency-selective pulse to the molecule.

In some embodiments (not depicted in FIG. 1), the target compound and the source compound can be combined in the solution prior to polarization of the source compound in step 110. In some such embodiments, a combination of the target compound and polarized source compound can be transported, as described in optional step 130. This combination can be transported in solution, as a precipitate, or in some other suitable form. In some embodiments, the steps of polarizing the source compound (e.g., using SABRE), transferring the polarization to the target compound and detection of the target compound signal can be repeated. In such embodiments, the source compound can repeatedly increase the polarization of the target compound, obtaining numerous hyperpolarized signals from the target molecules. Such repeated polarization transfer can be used for signal averaging or for performing spectroscopy in two dimensions or more. In some embodiments, the target compound may then be separated in step 150 (e.g., through liquid-liquid separation or precipitation). The separated target compound can be used in an NMR spectroscopy or imaging application in step 160.

Pets Source Compound Creation and Polarization

As described above with regards to step 110 of process 100, the source compound can be a PETS material. As described herein, many organic molecules exhibit a phenomena that when excited with specific wavelengths in the optical or ultraviolet (UV) spectrum, electrons in a low-level singlet state S0 of the molecule get excited to a higher-level singlet electron state S1. From this state, either radiative decay back to the singlet state or inter system crossing (ISC) to a triplet state can occur. These triplet states exhibit two key features: First, they are long-lived (e.g., on the order of microseconds to seconds) and can therefore be addressed on reasonable time scales. Second, the triplet state population between the three spin levels is non-uniform for many molecules, thereby creating a polarized state.

Several polarization molecules suitable for inclusion in PETs materials (e.g. acridine, pentacene, benzophenone, and the like) can have one of the spin states over 90% populated. Such polarization molecules can have almost unity polarization at temperatures and magnetic fields for which the thermodynamic polarization of the electron spins would otherwise be orders of magnitude smaller. Moreover, these polarization molecules can have different triplet spin states that exhibit different decay times to the singlet state, thereby creating another process where a differential population between the spin states, and therefore polarization, can be obtained.

An important aspect of these optically excited triplet states is that the electrons decay from the triplet state back to the singlet ground state. Free electrons can be a principal source of nuclear relaxation at lower temperatures. Thus, when the electrons in a molecule decay back into the singlet state (and are therefore without free electron spin), the molecule no longer contains paramagnetic impurities due to free electron spins which can relax the surrounding nuclear spin. Therefore, the nuclear spin polarization can reach a higher level, and a material can have a significantly longer relaxation time following the polarization sequence. Thus, optically excited triplet states can serve as a long-lasting source for polarizing target compounds via SPINOE.

Polarization molecules can be incorporated into a PETS material, forming a source compound, in several different ways. In some embodiments, the source compound can be a crystal grown from a melt. The disclosed embodiments are not limited to any particular method of growing the crystal from the melt. In some embodiments, the crystal can be grown using rapid temperature reduction, the Bridgman growth method, the Czochralski method, the cell method, another suitable crystal growth method, or any combination thereof. The polarization molecules can be included in the melt in concentration selected to produce a suitable source compound (e.g., a source compound having the desired polarization characteristics).

In some embodiments, the source compound can be a crystal grown using another suitable method, such as from a solution, gel, or vapor. Exemplary suitable crystal growth methods are disclosed in "Growth of bulk single crystals of organic materials for nonlinear optical devices: an overview" by Penn, Benjamin G., et al, which is incorporated herein by reference in its entirety for all purposes. Relevant portions of this publication discuss methods for molecular crystal growth and purification, including growth by physical vapor transport, growth from the melt via the Bridgman-Stockbarger Method, Czochralski Growth or Kyropoulos Method, growth from solutions including slow cooling processes, solvent evaporation processes and temperature difference processes.

In some embodiments, the source compound can be a Shpolsky matrix incorporating suitable polarization molecules. For example, pentacene can be incorporated into n-heptane, n-nonane, n-decane, n-dodecane, n-tetradecane, and n-hexadecane Shpolsky matrices. A method for such incorporation is disclosed in "Spectroscopic characteristics of pentacene in Shpol'skii matrixes", by Banasiewicz, M., I. Deperasinska, and B. Kozankiewicz which is incorporated herein by reference in its entirety for all purposes. As described in this paper, liquid samples can be bubbled with argon to remove oxygen and gently heated to increase the host solubility. Liquid samples can then be quickly frozen in liquid nitrogen before being inserted into a polarizer cryostat.

Figure 2A:
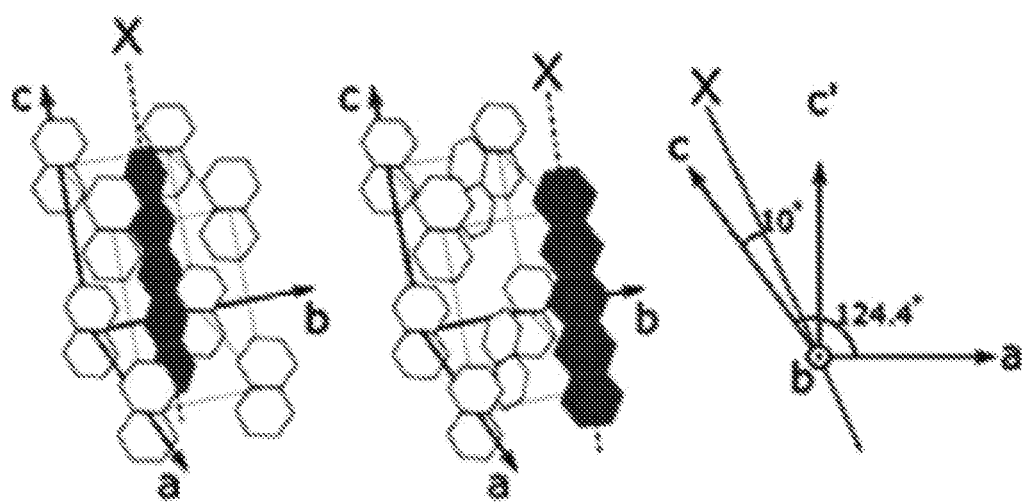
FIG. 2A depicts incorporation of pentacene dopants into naphthalene crystals, in accordance with disclosed embodiments.
Figure 2B:
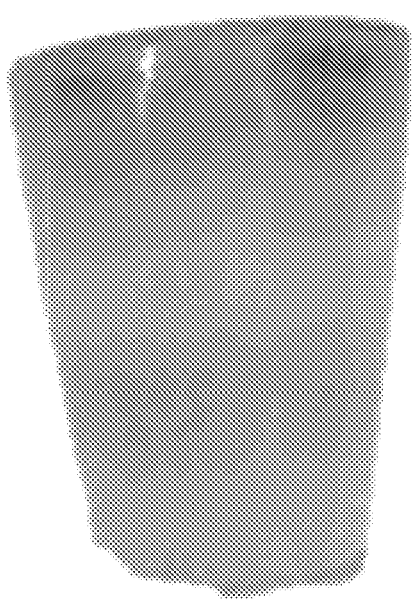
FIG. 2B depicts a naphthalene crystal doped with pentacene, in accordance with disclosed embodiments.

In some embodiments, the source compound can be a pentacene:naphthalene crystal. As depicted in FIG. 2A, pentacene dopants can be incorporated into a crystal lattice of the naphthalene crystals in two possible orientations. The presence of such defined orientations can enable hyperpolarization, consistent with disclosed embodiments. Relatively high amounts, up to around $10^{-4}$ mol/mol, of pentacene can be doped into a naphthalene crystal. An example of such a pentacene:naphthalene crystal is shown in FIG. 2B.

In some embodiments, a pentacene:naphthalene crystal can be grown using the self-seeding vertical Bridgman technique. In a variant of Bridgman growth, a double walled ampule can be used, where the inner wall has an open capillary towards the interspace between the walls. The ampule can be filled with naphthalene and pentacene and then moved through a steep temperature gradient, which includes the melting temperature of naphthalene. This temperature gradient can be achieved by a bath with two liquid phases, which are heated to different temperatures. When the ampule is lowered into the upper and warmer part of the bath, the pentacene-naphthalene mixture melts into a homogeneous liquid. Once the bottom of the ampule reaches the phase separation in the heating bath, crystallization starts in the interspace between the ampule walls. Here, the solidification happens with multiple nuclei, leading to a polycrystalline area in the interspace between the walls. By moving the ampule slowly within that region, the number of nucleation events can be kept minimal, leading to a polycrystal with relatively large grains. Once the ampule is lowered further, the capillary of the inner wall gets in contact with the polycrystal. Ideally, the crystal orientation of only one single grain forms within the capillary. That self-seeding process favors the emergence of a single crystal within the inner wall of the ampule.

Consistent with disclosed embodiments, DNP can be used in step 110 of process 100 to transfer polarization from electron spins to nuclear spins of the source atoms of the source compound. DNP can use electromagnetic irradiation (e.g., microwave or radio frequency irradiation) or magnetic field tuning to transfer electron spins to nuclear spins. In some embodiments, polarization transfer can be accomplished through level avoided crossing (LAC), or other suitable phenomena. DNP protocols can exploit at least one of interactions between electron spins or underlying physical mechanisms (e.g., fulfilling a resonance condition, such as the Hartmann-Hahn condition, or excitation of selective transitions, such as irradiation at a frequency matching the energy gap between two quantum states). DNP protocols can differ in the configurations used to achieve these conditions. DNP protocols can also differ in the usage of microwave pulses or continuous microwave radiation.

In some embodiments, DNP can be used in conjunction with PETS materials to obtain a polarized source compound in step 110 of process 100. In some implementations, high nuclear polarizations can be obtained in PETS materials using DNP (e.g., >10%, >20%, >30%, >40%, >50%, >60%, >70%, or >80%). However, the disclosed embodiments are not limited to using DNP in conjunction with PETS compounds. DNP can be used with other compounds, and PETS materials can be polarized using other methods.

Suitable DNP protocols consistent with disclosed embodiments are discussed in "Room temperature hyperpolarization of nuclear spins in bulk", by Tateishi, Kenichiro, et al. (e.g., for pentacene:p-terphenyl), "High proton spin polarization with DNP using the triplet state of pentacene-d14", by Eichhorn, T R, et al. (e.g., for pentacene:naphthalene), "Dynamic nuclear polarisation by photoexcited-triplet electron spins in polycrystalline samples", by Takeda, Kazuyuki, K. Takegoshi, and Takehiko Terao (e.g., polycrystalline samples of pentacene:naphthalene with random crystal orientations). Suitable DNP methods are also disclosed in Section II of "Dynamic nuclear polarisation at high magnetic fields", by Maly, Thorsten, et al. In addition, sophisticated DNP sequences such as those disclosed "Robust optical polarization of nuclear spin baths using Hamiltonian engineering of nitrogen-vacancy center quantum dynamics", by Schwartz, Ilai, et al, can enable fast polarization transfer. Suitable DNP methods disclosed in "Dynamical nuclear polarization using multi-colour control of color centers in diamond", by Yang, Pengcheng, Martin B Plenio, and Jianming Cai, and "Enhanced dynamic nuclear polarization via swept microwave frequency combs" by Ajoy, A, et al. can enable nuclear polarization transfer in nanocrystals, or polycrystalline source materials or bulk samples (e.g., using colour centers in nanodiamonds). The DNP protocols and preparation techniques disclosed in these references are incorporated herein by reference in their entireties for all purposes.

Consistent with disclosed embodiments, a DNP protocol can include a polarization sequence. Such a polarization sequence can include a polarization step followed by a transfer step. In the polarization step, the source compound can be exposed to a strong optical pulse. The duration of the optical pulse can be at least about 10 nanoseconds (ns), 20 ns, 50 ns, 100 ns, 200 ns, 500 ns, 1 microsecond (μs), 2 μs, 5 μs, 10 μs, 20 μs, 50 μs, 100 μs, or more. The duration of the optical pulse can be at most about 100 μs, 50 μs, 20 μs, 10 µs, 5 µs, 2 µs, 1 µs, 500 ns, 200 ns, 100 ns, 50 ns, 20 ns, 10 ns, or less. The duration of the optical pulse can be within a range defined by any two of the preceding values, such as 100 ns to 10 The energy in an optical pulse can be at least about 0.1 millijoules (mJ), 0.2 mJ, 0.5 mJ, 1 mJ, 2 mJ, 5 mJ, 10 mJ, or more. The energy in an optical pulse can be at most about 10 mJ, 5 mJ, 2 mJ, 1 mJ, 0.5 mJ, 0.2 mJ, 0.1 mJ, or less. The energy in the optical pulse can be within a range defined by any two of the preceding values, such as between 0.1 mJ and 10 mJ, or greater. The energy and duration of the optical pulse can be selected to populate triplet states of polarization molecules in the source compound in a polarized fashion.

In some embodiments, electron spins can be transferred to hydrogen nuclear spins in the source compound in the transfer step using the integrated solid effect (ISE). By changing the parameters of the transfer step, other species of nuclear spins may be affected. In some embodiments, for example, electron spins can be transferred to $^{13}C$ nuclear spins in the compound by using a different B1 microwave (MW) field. In some embodiments, the B1 microwave field is applied in a direction transverse to a magnetizing field B0 in which the compound is located. In various embodiments, electron spins can be transferred to nuclear spins in the transfer step using alternatives to ISE. For example, the solid effect, the cross effect, or low-field thermal mixing (in the case of a very high concentration of the PETS molecules) can be used to effect spin transfer. As an additional example, pulsed DNP methods such as the nuclear spin orientation via electron spin locking (NOVEL) sequence or dressed-state solid effect can be used to effect spin transfer.

Figure 3B:
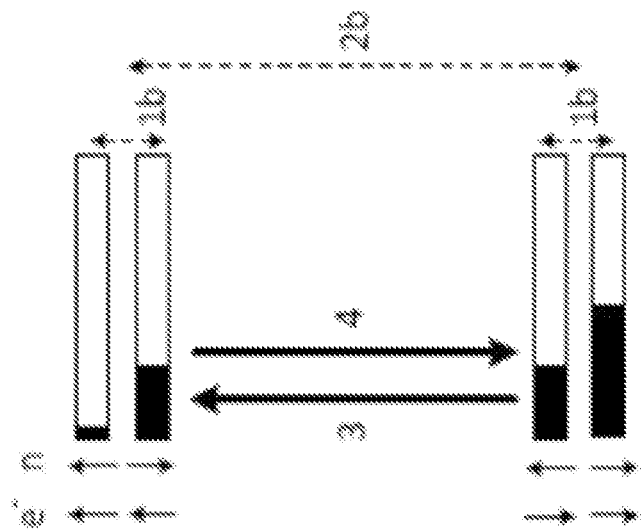
FIGS. 3A and 3B depict spin transference for an exemplary dynamic nuclear polarization (DNP) method that achieves spin transfer using the Solid Effect, in accordance with disclosed embodiments.
Figure 3A:
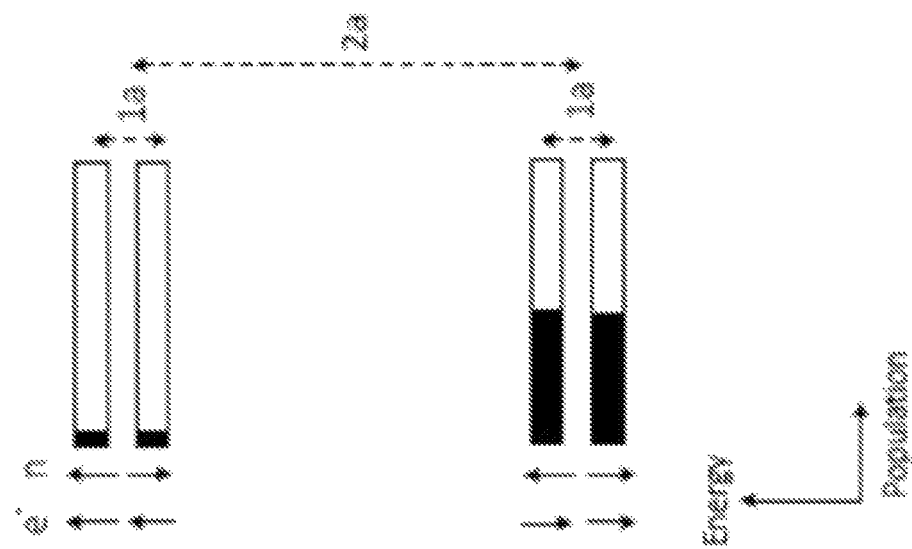

FIGS. 3A and 3B depict spin transference that occurs during an exemplary DNP protocol that achieves spin transfer using the solid effect. This exemplary method transfers polarization from the electron spin to the nuclear spin, increasing the nuclear polarization while decreasing the electron polarization. FIGS. 3A and 3B depict the different electron/nuclear spin states in a source atom of a source compound as four levels, with the black bar representing the population in the source compound at each level. Prior to initiation of spin transfer, as shown in FIG. 3A, the source compound exhibits greater electron spin polarization than nuclear spin polarization. The two bottom levels therefore are depicted with a greater population than the two top levels. Using microwave or rf irradiation on resonance with the so-called forbidden transition between the states $|\uparrow\rangle_e|\downarrow\rangle_n \leftrightarrow |\downarrow\rangle_e|\uparrow\rangle_n$ saturates the population of the two states $|\uparrow\rangle_e|\downarrow\rangle_n$, $|\downarrow\rangle_e|\uparrow\rangle_n$. This saturation increases the overall population of the $|\uparrow\rangle_n$ state and reduces the overall population of the $|\downarrow\rangle_e$ state. Therefore the nuclear spin polarization is increased while the electron spin polarization is decreased, as shown in FIG. 3B, effectively transferring polarization from electron spin to the nuclear spin.

In some embodiments, polarization of the electron spins can be transferred to the nuclear spins using an interaction involving at least two electron spins and a nuclear spin (e.g., using cross effect and low-field thermal mixing DNP protocols). Such an interaction can rely on allowed transitions of several electron spins and a nuclear spin involving a homogeneously or inhomogeneously broadened electron paramagnetic resonance (EPR) line. Energy can be conserved in the broadening of the EPR line when two or more electron spins and a nuclear spin are flipped simultaneously.

In various embodiments, the electron spins can be transferred to the nuclear spins using a variant of the integrated solid effect (ISE), in which a multi-frequency microwave "comb" sweeps several microwave frequencies in parallel. Such a technique can be particularly suitable for transferring polarization in nanocrystals, polycrystalline source materials or bulk samples.

In some embodiments, triplet lifetime can be extended and the polarization of the compound increased by preparing the triplet state before the DNP protocol. This can be done via a population transfer between the excited state sublevels (e.g. by a 180-degree pulse resonant with the transition frequency, or the like) to a different spin state with a longer relaxation time. Additional details of preparing a triplet state before a DNP protocol are provided in "Dynamic Nuclear polarisation with Paramagnetic Centers Created by Photo-Excitation", by Eichhorn, Tim Rolf, which is incorporated herein by reference in its entirety for all purposes.

In some embodiments, polarization transfer from the electron spins to the nuclear spins can be achieved without using microwaves by tuning an external magnetic field to the level avoided crossing (LAC) of the electron spins. Additional details of polarization transfer are provided in "Dynamic Nuclear polarization with Paramagnetic Centers Created by Photo-Excitation", by Eichhorn, Tim Rolf, which is incorporated herein by reference in its entirety for all purposes.

In some embodiments, the external magnetic field can be selected according to the desired application. For example, for polarization of target compounds for hyperpolarized MM applications or NMR spectroscopy in an external spectrometer, the magnetic field can be smaller than 5 tesla (T). In some embodiments, external magnetic fields can be used that have a low magnetic flux density (e.g., less than 2 T, less than 1 T, less than 0.5 T, less than 0.2 T, less than 0.1 T, less than 0.05 T, less than 0.02 T, less than 0.01 T, or lower). Advantageously, such magnetic flux densities can be achieved using a permanent magnet or electromagnet, without requiring use of cryogenic superconducting materials. Furthermore, such magnetic fields can be measured using conventional methods (e.g., using a gaussmeter). Accordingly, the equipment requirements for (and therefore the costs of) such methods can be reduced, as compared to other methods of polarizing the source compound.

Consistent with disclosed embodiments, the induced relaxation of the nuclear spins in the source compound can be reduced by means of actively decoupling the nuclear spins from possible electron spins on the surface of the source compound (e.g., electron spins arising from contaminants on the surface of the source compound). Such decoupling can be achieved by driving the electron spins with microwave or radio frequency irradiation at their Larmor frequency or energy transition frequencies (e.g., when there exists strong hyperfine splitting or spin-1 electron spin), or in the electron-nuclear zero-quantum or double-quantum resonance conditions.

In some embodiments (e.g., NMR spectroscopy applications), it can be advantageous to perform the polarization transfer from the optically polarizable electron spins to the nuclear spins in-situ (e.g., in the NMR device). In such embodiments, steps 110, 130, and 150 of process 100 can be performed in-situ. Accordingly, the same magnet can then be used for obtaining the source compound (e.g., through transfer of polarization to the nuclear spins of the source compound) and for performance of the NMR spectroscopy. For compounds including polycrystals, single crystals, or single crystals in the form of micro or nanoparticles, a low magnetic field (e.g., below 1000 millitesla (mT), 500 mT, 200 mT, 100 mT, 50 mT, 20 mT, 10 mT, 5 mT, 2 mT, 1 mT, or another suitable field) can enable addressing many of the orientations of the PETS electron spins.

Figure 4:
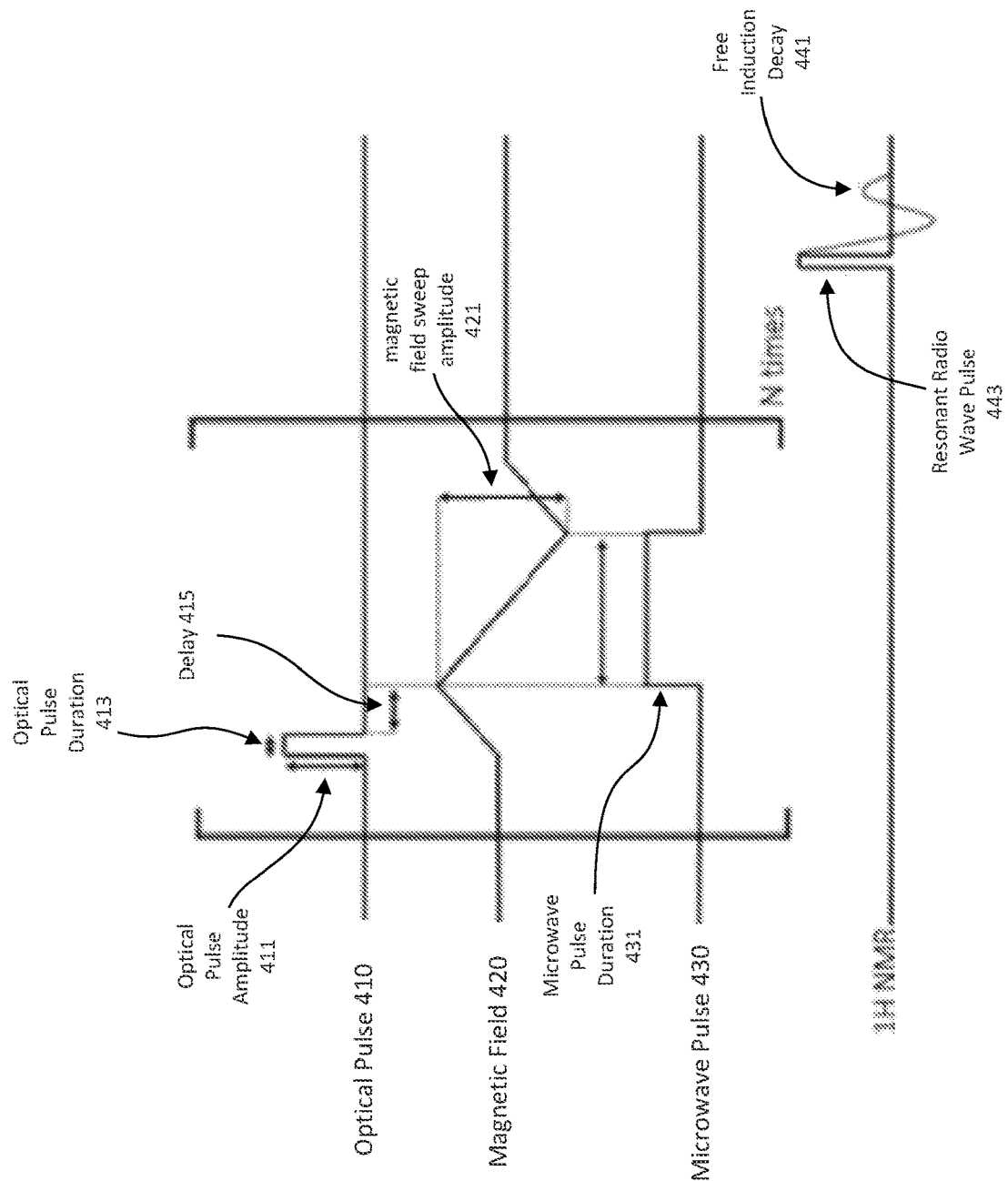
FIG. 4 depicts an exemplary sequence of optical irradiation, magnetic field sweep and electromagnetic irradiation suitable for inducing polarization in a compound, in accordance with disclosed embodiments.

FIG. 4 depicts an exemplary sequence of optical and magnetic interactions (e.g., a polarization sequence) suitable for inducing polarization in a source compound. In this example, the source compound is a sample of pentacene-d14:naphthalene-h8 crystal. The sample can be as large as 100 to 300 mm$^3$. In some embodiments, the sample can be cooled to 100 kelvin (K) or lower, while placed in a magnetic field of at least 1 kilogauss (kG), 2 kG, 5 kG, 10 kG, 20 kG, 50 kG, or 100 kG that is oriented along the pentacene molecules' long axis. The sequence can include multiple repeats of an optical pulse followed by a magnetic field sweep. In each repeat, one or more optical pulses (e.g., laser pulses) can excite the pentacene molecules into a short-lived triplet state. This can be achieved by populating a higher singlet state with optical pulses (e.g., Optical Pulse 410), each optical pulse having an optical pulse amplitude 411 of and an optical pulse duration 413, in which the slower intersystem crossing from the singlet to the triplet state takes place. In some embodiments, the optical pulse amplitude has a pulse energy of at least about 1 mJ, 2 mJ, 5 mJ, 10 mJ, 20 mJ, 50 mJ, 100 mJ, 200 mJ, 500 mJ, 1000 mJ, or more, at most about 1000 mJ, 500 mJ, 200 mJ, 100 mJ, 50 mJ, 20 mJ, 10 mJ, 5 mJ, 2 mJ, 1 mJ, or less, or a pulse energy that is within a range defined by any two of the preceding values. In some embodiments, the pulse duration is at least about 10 ns, 20 ns, 50 ns, 100 ns, 200 ns, 500 ns, 1 µs, 2 µs, 5 µs, 10 µs, 20 µs, 50 µs, 100 µs, or more, at most about 100 µs, 50 µs, 20 µs, 10 µs, 5 µs, 2 µs, 1 µs, 500 ns, 200 ns, 100 ns, 50 ns, 20 ns, 10 ns, or less, or within a range defined by any two of the preceding values. After a delay 415, the magnetic field 420, which has been ramped up before, sweeps through the full triplet's electron spin resonance linewidth (e.g., magnetic field sweep amplitude 421) of a few G, while irradiating with a microwave pulse 430 having a microwave pulse duration 431 in order to facilitate Hartmann-Hahn matching of all spin packets within the line. In some embodiments, the delay is at least about 10 ns, 20 ns, 50 ns, 100 ns, 200 ns, 500 ns, 1000 ns, or more, at most about 1000 ns, 500 ns, 200 ns, 100 ns, 50 ns, 20 ns, 10 ns, or less, or within a range defined by any two of the preceding values. After repeating this sequence for N times, the proton signal can be read out via the free induction decay 441 of a resonant radio frequency pulse 443 with a non-destructive small tip-angle amplitude. As depicted in FIG. 5, this sequence of optical and magnetic interactions can increase polarization in the sample to greater than 50%.

FIG. 5 depicts NMR signal reads from a compound before and after repeated iterations of the polarization sequence depicted in FIG. 4. In FIG. 5, the depicted X-axis is the frequency of the NMR signal and the depicted y-axis is the signal strength. A first trace depicts the NMR signal from the compound at thermal equilibrium (multiplied by 16,000). A second trace depicts the NMR signal read from the compound with 4% polarization (multiplied by 4). A third trace depicts the NMR signal read from a compound with 50% polarization. The increase in polarization can be the result of repeated iterations of the polarization sequence depicted in FIG. 4.

Creation and Polarization of Source Compounds Using Spin Order

Consistent with disclosed embodiments, electron spin order can be transferred to nuclear spins of the source atoms of the source compound in step 110 of process 100, polarizing the source compound. Such methods (e.g., PHIP, PHIP-SAH, SABRE, or the like) are described herein with regards to parahydrogen, for convenience of disclosure, but are similarly applicable to orthodeuterium and paratritium.

FIG. 6 illustrates a process 600 for generating and isolating a polarized source compound using PHIP, PHIP-SAH, or SABRE polarization. In some embodiments, such generation and isolation can be performed as part of step 110 of process 100. In various embodiments, the polarized source compound can then optionally be separated from hydrogenation catalysts or reaction byproducts (e.g., as in step 120 of process 100) and/or transported from the location where it was generated to another location for use (e.g., as in step 130 of process 100). The polarized source compound can be combined with the target compound (e.g., as in step 140 of process 100).

In step 610 of process 600, parahydrogen can be generated and optionally transported. Parahydrogen is a form of molecular hydrogen. In this form of molecular hydrogen, the two proton spins are in the singlet state. In some embodiments, parahydrogen may be formed in a gas form or in a liquid form. For example, in some embodiments, parahydrogen may be generated in gas form by flowing hydrogen gas through a chamber with a catalyst. In some embodiment, the hydrogen gas may be subjected to a low temperature, such as a temperature of at most about 100 K, 90 K, 80 K, 70 K, 60 K, 50 K, 40 K, 30 K, 20 K, 10 K, 9 K, 8 K, 7 K, 6 K, 5 K, 4 K, 3 K, or less. In some embodiment, the catalyst may be iron oxide. In some embodiments, the hydrogen gas contains both parahydrogen and orthohydrogen, and the low temperature brings the hydrogen gas to thermodynamic equilibrium in the chamber, during which the population of parahydrogen grows.

In some embodiments, the gas can be generated at a first location and subsequently transported to a second location for use. In some embodiments, a first location may be a chamber, which may be part of a container, bottle, holder or other regions capable of holding a gas or a liquid. Such a chamber may be maintained at a suitable pressure, temperature, or combination thereof. In some embodiments, the first location may refer to a physical location such as a room, a lab, a particular warehouse, hospital or other location where the parahydrogen may be generated.

In some embodiments, the generated parahydrogen may be transported in a chamber, which may be different from the chamber where the parahydrogen was generated. The chamber transporting the parahydrogen gas may be maintained at a suitable pressure or temperature, which may be transported by vehicle or persons. In some embodiments, transporting the parahydrogen may involve moving the parahydrogen from one container to a different container. In some embodiments, transporting the parahydrogen may involve moving the parahydrogen within the same location, such as from one part of a room to another part of the room. In some embodiments, transporting the parahydrogen may involve moving the parahydrogen from one room in a building to a different room in the same building or to a nearby building. In some embodiments, transporting the parahydrogen may involve moving the parahydrogen to a different location in another part of the same city, or a different city. For example, transporting the parahydrogen may involve bringing the parahydrogen to a vicinity of a polarizer or an NMR/MRI device. In another example, in some embodiments, transporting the parahydrogen may involve packaging or shipping the parahydrogen in suitable containers as illustrated in FIG. 10.

In step 620 of process 600, a source compound can be generated using the parahydrogen. In some embodiments, a solution can be formed by combining a precursor molecule (or the source compound in SABRE embodiments), a solvent, and a catalyst for hydrogenation (e.g., a hydrogenation catalyst). The solution can be formed in a mixing mechanism, which can be configured to introduce, hold, or facilitate a blend, mixture, or solution of two or more materials. In some embodiments, the mixing mechanism may be disposed in a chamber, and the mixing may occur inside the chamber. In some embodiments, the solution may be mixed at a location away from the chamber. In some embodiments, the solution may be at least 10 microliters (μL), 20 μL, 50 μL, 100 μL, 200 μL, 500 μL, 1000 μL, or more in volume. A concentration of the precursor molecule can be at least 10 millimolar (mM), 20 mM, 50 mM, 100 mM, 200 mM, 500 mM, 1 M, 2 M, 5 M, or more. In some embodiments, the mixing mechanism may be a gas-liquid exchange mechanism. For example, the gas-liquid exchange mechanism may be a bubbler or a diffusion system. In some embodiments, the mixing mechanism may comprise membranes adapted to permit diffusion of molecular hydrogen. In some embodiment, the mixture may be formed when the parahydrogen gas is bubbled into the mixture.

In some embodiments, the hydrogenation catalyst can be any molecule, complex or particle system that catalyzes a hydrogenation reaction (for PHIP or PHIP-SAH processes) or that catalyzes a polarization transfer from parahydrogen (for SABRE processes). In some embodiment, a homogeneous metal catalyst such as a rhodium complex or a ruthenium complex may be used for coordination and activation of precursor molecules and parahydrogen. In embodiments utilizing SABRE, iridium complexes can be used as homogeneous catalysts. In some embodiments, a heterogeneous metal catalyst connected to a nanoparticle can be used for coordination and activation of the precursor molecules and the parahydrogen.

In some embodiments, the precursor molecule may have an unsaturated bond that can be hydrogenated by the parahydrogen gas. In PHIP embodiments, the hydrogenated precursor molecule can be the source compound. In PHIP-SAH embodiments, the hydrogenated precursor molecule can be a parahydrogetated precursor to the source compound. Preferably after bubbling the parahydrogen gas through, more than 50%, more than 80% or almost all of the molecules may be hydrogenated. In some embodiments, the hydrogenation may create Iz1Iz2 order, the lower energy state between |↑>|↓>, |↓>|↑> or singlet spin order on two hydrogens spins of the hydrogenated molecule. In such embodiments, the hydrogenated precursor molecule can serve as the source compound of process 100.

In some embodiments, the polarization occurs through a non-hydrogenative PHIP, also termed as signal amplification by reversible exchange (SABRE). In such embodiments, the described hydrogenation and polarization transfer steps can occur by polarization transfer from parahydrogen to the source compound while both are bound to the catalyst. The source compound, e.g. pyridine, may be able to reversibly bind to the catalyst. The bubbled parahydrogen gas may also reversibly bind to the catalyst, allowing for spin order or polarization transfer to the source compound. Preferably at the end of the process, the average polarization (or spin order) of the source atoms of the source compound is at least 1%, 2%, 5%, 10%, 20%, 50%, or more.

Consistent with disclosed embodiments, generation of the source compound in step 620 can include polarization transfer from electron spins to nuclear spins. Such polarization transfer can be performed in a magnetic field and can use electromagnetic irradiation. In some embodiments, polarization transfer can include application of at least one RF waveform to the parahydrogenated precursor molecule.

In some embodiments, the at least one RF waveform may be generated by a waveform generator. The waveform generator may include one more computing unit, processors, controllers, associate memories, PCs, computers services, or any devices capable of carrying computational operations using inputs and producing outputs.

The at least one RF waveform can be applied to the source compound using RF coils. The RF coils can be disposed around the chamber in which parahydrogenation was performed, or around another polarization-transfer chamber. The RF coils may have one or more channels. Such channels may be pathways for applying the RF signals to the source compound. There may be provided at least one channel for each different type of nuclear spin species. In some embodiment, there may be at least one proton ($^1$H) channel and at least one channel (e.g., additional channel(s)) for another nuclear spin species (e.g., $^3$H, $^{13}$C, $^{19}$F, $^{31}$P, or other suitable species). In some embodiments, the RF waveforms applied to the $^1$H channel and each of the additional channel(s) may differ. In some embodiments the at least one proton channel is used to selectively address one of the hydrogenated $^1$H spins. In some embodiments, the RF waveforms on the $^1$H channel and an additional channel (e.g., a $^{13}$C channel) are configured to apply a polarization transfer sequence, such as PH-INEPT, Goldman's sequence, S2M, S2hM or ESO-TERIC.

In some embodiments, the polarization transfer can be performed using a magnetic field having a strength of at least 1 microtesla (μT), 2 μT, 5 μT, 10 μT, 20 μT, 50 μT, 100 μT, 200 μT, 500 μT, 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, 500 μT, 200 μT, 100 μT, 50 μT, 20 μT, 10 μT, 5 μT, 2 μT, 1 μT, or less, or a magnetic field strength that is within a range defined by any two of the preceding values, such as 10 μT to 2000 mT. The magnetic field may be produced by an electro-magnet or a permanent magnet. The magnetic field may be applied to the sample in pulses or continuously. The magnetic field may be static or time varying. The magnetic field applied may be inhomogeneous. The inhomogeneity of the magnetic field can be characterized in parts per million (ppm) over a diameter of a spherical volume. In some embodiment, the magnetic field applied may have inhomogeneity of at least about 1 ppm, 2 ppm, 5 ppm, 10 ppm, 20 ppm, 50 ppm, 100 ppm, or more, at most about 100 ppm, 50 ppm, 20 ppm, 10 ppm, 5 ppm, 2 ppm, 1 ppm, or less, or an inhomogeneity that is within a range defined by any two of the preceding values.

In such a magnetic field, at least one RF waveform can be applied to the source compound to transfer polarization between the parahydrogen and a nuclear spin of the source compound (e.g., a nuclear spin of the source atom). The at least one RF waveform may include a sequence of elements. An element in the sequence of elements can be a RF pulse. For example, an element in the sequence of elements can be an excitation pulse. An excitation pulse may be an RF pulse that modifies energy level or spin phase of a material (e.g., to increase the detectable polarization signal in the source compound), such as a 90-degree (or approximately 90-degree pulse). An element in the sequence of elements can be a decoupling sequence. In some embodiments, a decoupling sequence can include one or more pulses, or one or more groups of RF pulses (e.g., described herein as a block of RF pulses, or pulse block).

In other embodiments, the polarization transfer can be performed using a magnetic field lower than 0.1 G. In such a magnetic field, the polarization can be transferred by utilizing level avoided crossings (LAC) between the proton spins and other spin species of interest, including $^{13}C$, $^{15}N$, $^{19}F$, or $^{31}P$. The magnetic field can be tuned to the exact field for the LAC, or it can be temporally varied, so as for example to sweep through the LAC condition.

In various embodiments utilizing SABRE, the spin order transfer can happen at magnetic fields that allow spontaneous transfer between the parahydrogen and the molecule of choice, for example using signal amplification by reversible exchange in shield enables alignment transfer to heteronuclei (SABRE-SHEATH). The spin order of the parahydrogen may be transferred to polarization on the molecule, or to spin order on the molecule.

In various embodiments, the polarization of $^1H$ molecules using SABRE, PHIP, or PHIP-SAH can be transferred to other molecules by chemical exchange, for example using the SABRE-RELAY method. Such other molecules can form the source compound described herein with regards to FIG. 1.

In various embodiments, the spin order on the protons spins is not transferred to other spin species but is instead converted to polarization on the proton spins. This can be done for example by singlet to magnetization conversion pulses, e.g. S2M, or with spin locking induced crossing (iSLIC), similar to methods used in singlet NMR. In another embodiment, the spin order is transformed to polarization by a PHIP-echo sequence in a high magnetic field.

In some embodiments the spin order on the protons can be transformed to polarization through application of a pulse sequence. In some embodiments, the spin order on the protons of a molecule with a chemical shift difference between the hydrogenated spins can be converted to polarization by first hydrogenating the molecules in a low magnetic field and then transferring the molecules to a high magnetic field, i.e., using an adiabatic longitudinal transport after dissociation engenders net alignment (ALTADENA) sequence. The spin order of the two protons due to the hydrogenation can then be transferred to ALTADENA order, i.e. most spins adiabatically proceeding from the singlet state to the $|\uparrow\rangle|\downarrow\rangle$ state (or alternatively most spins proceeding to the $|\downarrow\rangle|\uparrow\rangle$ state). In order to transfer this spin order to polarization, as the spins are separated by their chemical shift, a selective pulse can be applied flipping only one of the two spins. In another specific embodiment, a molecule with hydrogenated protons with the same chemical shift is hydrogenated in a high or low magnetic field, and the singlet order is transformed to magnetization using a pulse sequence (e.g. S2M, PulsePol) or RF irradiation (e.g. iSLIC).

In some embodiments using a high concentration of the source compound and a high degree of electron or nuclear spin polarization of the source compound, the application of a selective pulse or a pulse sequence can induce substantial radiation damping. In some embodiments the radiation damping effect during the transfer of the spin order to polarization can be mitigated by reducing the effective quality factor Q of a polarizer (e.g., an NMR spectrometer) at the $^1H$ resonance of the spin-ordered spins to less than 20, 10, 5, 1, 0.5, 0.2, or 0.1 during the application of the selective pulse or pulse sequence. In some embodiments this is performed by a controllable retuning of the resonance of a probe circuit (e.g., the NMR probe circuit of an NMR spectrometer) to a value detuned from the $^1H$ resonance, thereby reducing the amplification factor of a polarizer RF coil (e.g., the NMR coil of an NMR spectrometer) at the $^1H$ resonance. In some embodiments, the quality factor Q of the probe circuit can be reduced by neutralizing the voltage in the receiver coil induced by the strong NMR signal via an electronic feedback circuit.

In some embodiments, the transfer of spin order to magnetization can be achieved using radiation damping. For example, in an ALTADENA experiment with inequivalent $^1H$ spins, e.g. with a sufficiently large splitting due to chemical shift, application of an excitation pulse (even a pulse with a small flip angle) can induce radiation damping, resulting in a net magnetization of both $^1H$ spins. In some embodiments, the radiation damping can be induced without an excitation pulse (e.g. by statistical fluctuations).

The disclosed embodiments are not limited to embodiments in which spin order on the source compound is converted to nuclear spins on $^1H$ source atoms prior to combination of the source compound with the target compound. In some embodiments, the source compound can be combined with the target compound and then the spin order can be converted to nuclear spin polarization of $^1H$ source atoms. This nuclear spin polarization can then be transferred to the target atoms using NOE, as described herein.

Source Compound Precipitation

As described above with regards to step 120 of process 100, the polarized source compound can be at least partially isolated, in accordance with disclosed embodiments. In some embodiments, the polarized source compound can be induced to solidify and precipitate, thereby creating crystals that are either polarized or that contain spin-order. As used herein, spin order generically refers to an excess of population in some electronic or nuclear state (such as a particular spin eigenstate of a spin-½ electron or nucleus, or a singlet or triplet state of a spin-1 system such as a PETS system). In some embodiments, such precipitation can be induced by reducing the solubility of the polarized or spin-order containing source compound. The solubility of the source compound in the solution can be reduced by modifying the solvent (or mixture or solvents) in which the source compound is dissolved. Solidification and precipitation of the polarized source compound can enable efficient mechanical separation of the source compound.

Solid hyperpolarized source compound particles can be used in multiple applications. Hyperpolarized source compound microparticles configured to be insoluble in aqueous solutions can be used as NMR/MRI tracers. Hyperpolarized source compound precipitates can also provide a source for transferring polarization to a target compound, as described herein.

As a non-limiting example, fumarate polarized by PHIP can be precipitated in an aqueous solution. Disodium fumarate and fumaric acid exhibit a large solubility difference (e.g., 1.42 M versus 60 mM, respectively) in an aqueous solution. Disodium fumarate was polarized and dissolved in water with a concentration of 1.2 M. Upon addition of an acid (HCl) the resulting fumaric acid quickly precipitated to form microcrystals.

Consistent with disclosed embodiments, an organic solvent can be used for precipitation of the polarized source compound. In some embodiments, the parahydrogen-induced polarization occurs in the organic solvent. Parahydrogen is typically more soluble in organic solvents than aqueous solvent, and therefore the hydrogenation can occur more efficiently in organic solvents.

In various embodiments, the hydrogenation and optionally the polarization transfer can be performed in an aqueous solution. The aqueous solution can be mixed with a miscible organic solvent for inducing precipitation. In organic solvents, carboxylic acids are typically sufficiently soluble for PHIP concentrations. For example fumaric acid is soluble to around 220 mM in acetone at room temperature. However, the salts of these acids are typically very insoluble, (e.g., below 1 mM, 0.1 mM, 0.01 mM, or lower). Therefore, precipitation in an organic solvent can be used with source compound concentrations suitable for achieving high polarization using PHIP or SABRE.

Consistent with disclosed embodiments, solidification or precipitation can separate the polarized source compound (or polarized molecules) from the hydrogenation catalysts used to hydrogenate the precursor molecule (or catalyze polarization transfer, in SABRE implementations). As described herein, the polarized source compound (or polarized molecules) can be solidified or precipitated into crystals, amorphous solid particles or polycrystal material. Following the solidification or precipitation, the source compound (or polarized molecule) can be separated from the solution containing the hydrogenation catalysts (e.g., through filtration of the precipitate and a washing step with a solvent which does not dissolve the source compound). In some embodiments, most of the hydrogenation catalyst can be separated from the polarized molecules in the sample by solidification. For example, more than 99% by weight of the hydrogenation catalyst (or 99.99%, 99.999%, or more) can be separated from the source compound (or polarized molecules).

In some embodiments, forming the polarized source compound can include cleaving a sidearm of the polarized molecule (e.g., as in PHIP-SAH). The sidearm of the polarized molecule may be cleaved through hydrolysis. In some embodiments, the cleavage of the sidearm can be performed in a solvent in which the polarized molecule is more soluble than the polarized source compound (e.g., the polarized molecule without the sidearm). Accordingly, cleavage of the sidearm can cause precipitation of the polarized source compound. In some embodiments, the solvent can be an organic solvent and the cleavage can be performed under basic conditions. Following the cleavage, the less-soluble polarized source compound can undergo rapid solidification while preserving polarization. In various embodiments, the hydrogenation, polarization transfer, and sidearm cleavage can be performed in the same solvent. In some embodiments, hydrogenation and polarization transfer can be performed in a first solution, and then a second solution can be added to the first solution prior to cleavage of the sidearm. For example, a basic solution (e.g., an aqueous solution of sodium hydroxide, or the like) can be added to cleave the sidearm.

In some such embodiments, the precipitation of the polarized precursor molecules can occur before the cleavage, such that the polarized precursor molecules retain the sidearm while solidified (e.g., are still in ester form). Such embodiments may be used, for example, when the polarized precursor molecule (e.g., with the sidearm) is more stable than the polarized source compound (e.g., without the sidearm). Such precipitation can be performed by modifying the pH of the solvent such that the solubility of the polarized molecule is reduced, or by mixing in a solution or other compounds that lowers the solubility of the polarized molecule, or by any combination thereof. In such embodiments, the cleavage can be performed after re-dissolution of the polarized molecule or the polarized source compound in another solvent (e.g., a more biocompatible solvent).

In some embodiments, the precipitation can occur after the cleavage of the sidearm from the polarized molecules (to thereby form the polarized source compound). Such precipitation can be performed by modifying the pH of the solvent such that the solubility of the polarized source compound is reduced, or by mixing in a solution or other compounds which lowers the solubility of the polarized source compound, or by any combination thereof.

In some embodiments, the conversion of spin order to polarization can occur before the polarized molecules or the polarized source compounds are made to solidify and precipitate. In other embodiments, this conversion happens after re-dissolution of the solidified source compound with the target compounds.

Source Compound Transport

As described herein with regards to FIG. 1, a polarized compound (e.g., a source compound or target compound) can be transported to a destination location from an origin location (e.g., in step 130 of process 100). Consistent with disclosed embodiments, the compound can have a long nuclear relaxation time. Accordingly, the polarized compound can be stored and transported without undergoing an unacceptable degree of depolarization (e.g., more than 90%, 80%, 70%, 60%, 50%, 40%, 30%, 20%, 10%, 9%, 8%, 7%, 6%, 5%, 4%, 3%, 2%, or 1% depolarization). Because the polarization of the source or target compound can be performed separately from any further processing of the source or target compound, polarization and further processing can be performed by separate devices, each optimized for different purposes. Furthermore, production of the polarized compound for sufficient multiple end-users can be performed at a centralized facility, enabling greater efficiencies and economies of scale.

In some embodiments, a polarized source compound can be transported to a destination location and then processed into microparticles or nanoparticles, prior to transferring polarization from the polarized source compound to a target compound. In some embodiments, the polarized source compound can be processed into microparticles or nanoparticles prior to transportation to the destination location. In various embodiments, a polarized target compound can be transported to the destination location and then dissolved into a solvent suitable for use in an intended NMR spectroscopy or MRI application.

A transportation device can be configured to transport the polarized source compound or the polarized target compound. The transportation device can be arranged and configured for transporting one or more samples of the polarized source compound or the polarized target compound (or multiple polarized source compounds or target compounds) simultaneously. The transportation device can be configured to maintain the one or more samples in a magnetic field of at least 1 Gauss (G), 2 G, 5 G, 10 G, 20 G, 50 G, 100 G, 200 G, 500 G, or 1000 G.

A permanent magnet or an electromagnet included in the transportation device can provide the magnetic field. Moreover, in some embodiments, the permanent magnet or electromagnet can be shielded to reduce the strength of the magnetic field outside the transportation device. The transportation device can also include a cooling system. The cooling system can be configured to maintain samples at a predetermined temperate or within a predetermined range of temperatures during transport. For example, the cooling system can be configured to maintain the samples at a temperature below 270 K, below 80 K, or below 4 K. In some embodiments, the transportation device can be configured to maintain the samples at approximately the temperature of dry ice, liquid nitrogen, or liquid helium. The transportation device can include insulation between the cooling system and the exterior of the transportation device, to minimize heat exchange with external environment. In some embodiments, the cooling system can be configured to maintain the temperature of the samples using a cold gas flow. In various embodiments, the cooling system can be configured to maintain the temperature of the samples using a solid or liquid coolant, such as dry ice, liquid nitrogen, or liquid helium. In various embodiments, the transportation device can include a Dewar to provide cooling of the samples. In order to distribute the polarized samples also across large distances, the container preferably can be transported by standard transportation vehicles, such as planes, trains, trucks, cars and ships.

Combining Source and Target Compound

As described herein with regards to FIG. 1, a polarized source compound can be combined with a target compound (e.g., as described in step 140 of process 100). Such combining is not limited to any particular method of polarizing the source compound. In various embodiments, the source compound can be polarized using PHIP, PHIP-SAH, or SABRE; using DNP (e.g., source $^1H$, $^{19}F$, or $^{31}P$ atoms polarized using dissolution DNP, as described herein); using PETS; or using another suitable method.

Consistent with disclosed embodiments, a polarized source compound can be combined with a target compound in a solution. In some embodiments, the solution can be produced by dissolving the polarized source compound into the solution. This solution may already contain the target compound. Alternatively, the target compound can be added to this solution (e.g., in solid form, dissolved in another solution, or the like). In some embodiments, the source compound (or the target compound) can be first processed (e.g., crushed, ground, cut, or the like) into microparticles before dissolution in order to enhance the dissolution rate. In some embodiments, the source compound can be polarized in a first solution and the target compound can be added to this first solution (e.g., in solid form, dissolved in another solution, or the like).

Consistent with disclosed embodiments, the source compound can be soluble in the solvent and can be selected to retain polarization after dissolution. For example, source compounds such as disodium fumarate have a long relaxation time when dissolved at room temperature or other temperatures in the range of −150 degrees Celsius (° C.) to −200° C., enabling dissolution while preserving the polarization of the source atoms. Potential solvents can depend on the selected source compound. As a non-limiting example, when the polarized source compound is disodium fumarate or sodium pyridinium crystals, the potential solvents can include aqueous solutions, glycerol, dimethyl sulfoxide (DMSO), and alcohols. As another non-limiting example, when the polarized source compound is pentacene:naphthalene, pentacene:p-terphenyl or 3-phenylpropanoate crystals, the potential solvents can include organic solvents such as toluene, ether, ethanol, carboxylic acids, chloroform, hexane, acetic acid, butyric acid, DMSO and mixtures or derivatives thereof. In some embodiments the solvent is deuterated to a degree of at least 50%, 60%, 70%, 80%, 90%, or more.

In some embodiments the dissolution and mixing of the source and target compound is performed in an automated system. In some embodiments the automated polarization transfer system includes a transport magnet for maintaining source compound polarization. The source compound is then loaded into a vessel for crushing and dissolution. The transfer system contains a mechanism for mechanically breaking down the source compound into smaller particles for faster dissolution, for example by a crushing head, pestle or ultrasonic probe. In a dissolution vessel a solution potentially including the target compound is mixed with the crushed source compound for rapid dissolution. A separator such as a frit is used to separate the solution with the dissolved source compound from solid particles, with the solution then pumped into the NMR spectrometer.

In some embodiments, the concentration of the source compound in solution can be selected for efficient polarization transfer to the target compound. This concentration can be at least 100 mM, 200 mM, 500 mM, 1 M, 1.5 M, 2 M, 3 M, 4 M, 5 M, 6 M, or higher. Such high concentrations can enable efficient polarization transfer from the at least one source atom of the source compound to the at least one target atom of the target compound. As may be appreciated, the concentration of the source compound in solution during polarization transfer to the target compound (e.g., step 140 of process 100) can differ from the concentration of the source compound during initial polarization of the source compound (e.g., during step 110 of process 100). In some embodiments, the source compound concentration during polarization transfer can be far greater than the source compound concentration during initial polarization (e.g., 250 mM or less, 200 mM or less, 150 mM or less, 100 mM or less, 50 mM or less, 20 mM or less, or 10 mM or less), as high source compound concentrations can inhibit the initial polarization.

In some embodiments, the concentration of the source compound can be greater than or equal to the concentration of the target compound. For example, a concentration ratio of the at least one source atom to the at least one target atom can be at least 1:1, 2:1, 5:1, 10:1, 20:1, 50:1, 100:1, 200:1, 500:1, 1000:1, or more, at most 1000:1, 500:1, 200:1, 100:1, 50:1, 20:1, 10:1, 5:1, 2:1, 1:1, or less, or a ratio that is within a range defined by any two of the preceding values. When the source compound was polarized using a PHIP or SABRE process, the concentration of any hydrogenation catalysts (or reaction byproducts such as cleaved side arms) in the solution of the source and target compounds can be less than 1 µM, 500 nM, 200 nM, 100 nM, 50 nM, 20 nM, 10 nM, 5 nM, 2 nM, 1 nM, or less, more than 1 nM, 2 nM, 5 nM, 10 nM, 20 nM, 50 nM, 100 nM, 200 nM, 500 nM, 1 µM, or more, or within a range defined by any two of the preceding values. Such reduced concentrations can be achieved by separating (e.g. using filters, liquid-liquid separation, or other suitable methods) the polarized source compound from the hydrogenation catalysts (or reaction byproducts).

Nuclear Polarization Transfer

As described herein with regards to FIG. 1, nuclear spin polarization can be transferred from polarized source atoms of a source compound to target atoms of a target compound (e.g., as described with regards to step 140 of process 100). Consistent with disclosed embodiments, the nuclear spin polarization can be transferred by cross relaxation (e.g., spin polarization induced nuclear Overhauser effect, or SPINOE).

Consistent with disclosed embodiments, the source compounds can be selected to improve polarization transfer. In some embodiments, the polarized source atoms can be selected to have a high gyromagnetic ratio, thereby inducing a high cross relaxation rate to the target atoms. In some embodiments, the ratio of cross relaxation of at least one nuclear spin of target compounds induced by the source molecules to the total relaxation of the same nuclear spins is at least 0.001, 0.005, 0.01, 0.02, 0.05, 0.1, 0.2, 0.3, 0.5, or more. In some embodiments the polarization of at least one nuclear spin on the target compounds following the cross relaxation is at least 0.01%, 0.02%, 0.05%, 0.1%, 0.2%, 0.5%, 1%, 2%, 5%, 10%, or more.

In some embodiments, the source compound can be selected to have low intramolecular relaxation on the polarized source atoms, for example by selective deuteration of portions of the source compound or by the selection of molecules with slow-relaxing $^1$H spins.

In some embodiments, the source compound can be selected such that the polarized source atoms project from the source compound and are therefore well-exposed to the surrounding environment. For instance, the polarized source atoms can be located on a portion of the source molecule that is well-exposed to the surrounding environment, such as at or near the end of a sidechain or arm of the source molecule. Such a configuration can increase cross-relaxation with the target atoms.

In some embodiments, a cross-relaxation rate can be increased through selection of the solvent in which the source and target compounds are combined, the temperature of the solvent, the magnetic field in which the NOE takes place and/or the viscosity of the solvent.

In some embodiments the source compound can be chosen to have a long relaxation time, as compared to the time required to transfer the intended amount of polarization to the target compound (e.g., in order to achieve target compound polarizations described herein). The transfer time can depend on factors including diffusion rate, concentration of source molecule, concentration of target molecule, and cross-relaxation rate. In some embodiments, the relaxation time of the source compound can be at least 10 seconds, 20 seconds, 30 seconds, 50 seconds, 100 seconds, or more.

In some embodiments, RF irradiation (e.g., the rotating frame Overhauser enhancement spectroscopy (ROESY) NMR pulse sequences, or the like) can be provided to effect polarization transfer.

In some embodiments, a first magnetic field can be applied during polarization transfer and a second, differing magnetic field can be applied during NMR spectroscopy. In some embodiments, the first magnetic field can be selected to achieve high NOE polarization between the source compound and the target compound. The differing magnetic fields can be implemented using magnetic field cycling or physical transportation of the solution from the first magnetic field into the second magnetic field.

Intermolecular NOE in liquids can be understood as a transfer of magnetization between nuclear spins on molecules in close proximity, induced by the stochastic modulation of dipole-dipole couplings via their relative motion. Intramolecular NOE enhancements are commonly measured in routine NMR analysis, while the smaller intermolecular enhancements, sensitive to average molecular distances, have found applications in studies of intermolecular interactions. Similar transfer mechanisms for hyperpolarized systems have been observed in solutions with dissolved $^{129}$Xe and with sources polarized via dissolution DNP and with PHIP. However, previous attempts at polarization transfer via SPINOE from $^{129}$Xe, from sources polarized via dissolution DNP, and from source polarized via PHIP have typically resulted in trivially small target compound signal enhancements.

The magnetization transfer from source spins S to target spins I can be described by the semiclassical Solomon equations (as described in I. Solomon, Relaxation processes in a system of two spins, *Phys. Rev.*, 1955, 99, 559-565, which reference is incorporated herein in its entirety for all purposes), introducing autorelaxation rates $\rho_s \approx 1/T_{1,S}$ and $\rho_I \leq 1/T_{1,I}$ and cross-relaxation rate $\sigma$. In the situation where the source magnetization is enhanced by a factor $\epsilon_S^{hp}$ via hyperpolarization, and $\sigma \ll |\rho_I - \rho_S|^2$, the target enhancement is given by Equation (1).

$$\epsilon_I^{hp}(t) = -\epsilon_S^{hp} \frac{\sigma}{\rho_I - \rho_S}(e^{-\rho_S t} - e^{-\rho_I t}) \quad (1)$$

Note that the magnetization transfer curve follows an initial linear buildup in the opposite direction of the hyperpolarized source magnetization. Fitting only to Equation (1) does not allow the independent determination of the cross-relaxation rate and source polarization, but a standard (thermally polarized) measurement of NOE can be used to disentangle both parameters. In such an experiment, the source spins can be saturated by continuous RF irradiation, leading to a steady-state enhancement of the target spins given by Equation (2).

$$\epsilon_I^0 = 1\sigma/\rho_I \quad (2)$$

Separate measurements of $T_1$ can then allow a to be determined unambiguously.

Consistent with disclosed embodiments, NOE can be demonstrated in solutions containing highly concentrated (e.g., 10% v/v, 20% v/v, 50% v/v, or the like) naphthalene-h8 as a source compound in $CDCl_3$. Such a solution can further contain low concentrations of acetone, 1,1,2,2-tetrachloroethane (TCE), tetrahydrofuran (THF), toluene, and/or acetone as target compounds for spin polarization transfer. Both naphthalene and the target compounds have $T_1$ relaxation times greater than 10 seconds, so polarization build-up times are long enough to be easily monitored via small flip angle experiments. Acetone and TCE can be chosen as target compounds because the $T_1$ relaxation time of acetone, 13.5 s, is shorter than that of the source, while the $T_1$ relaxation time of TCE, 35.6 s, is longer.

Figures 8A, 8B:
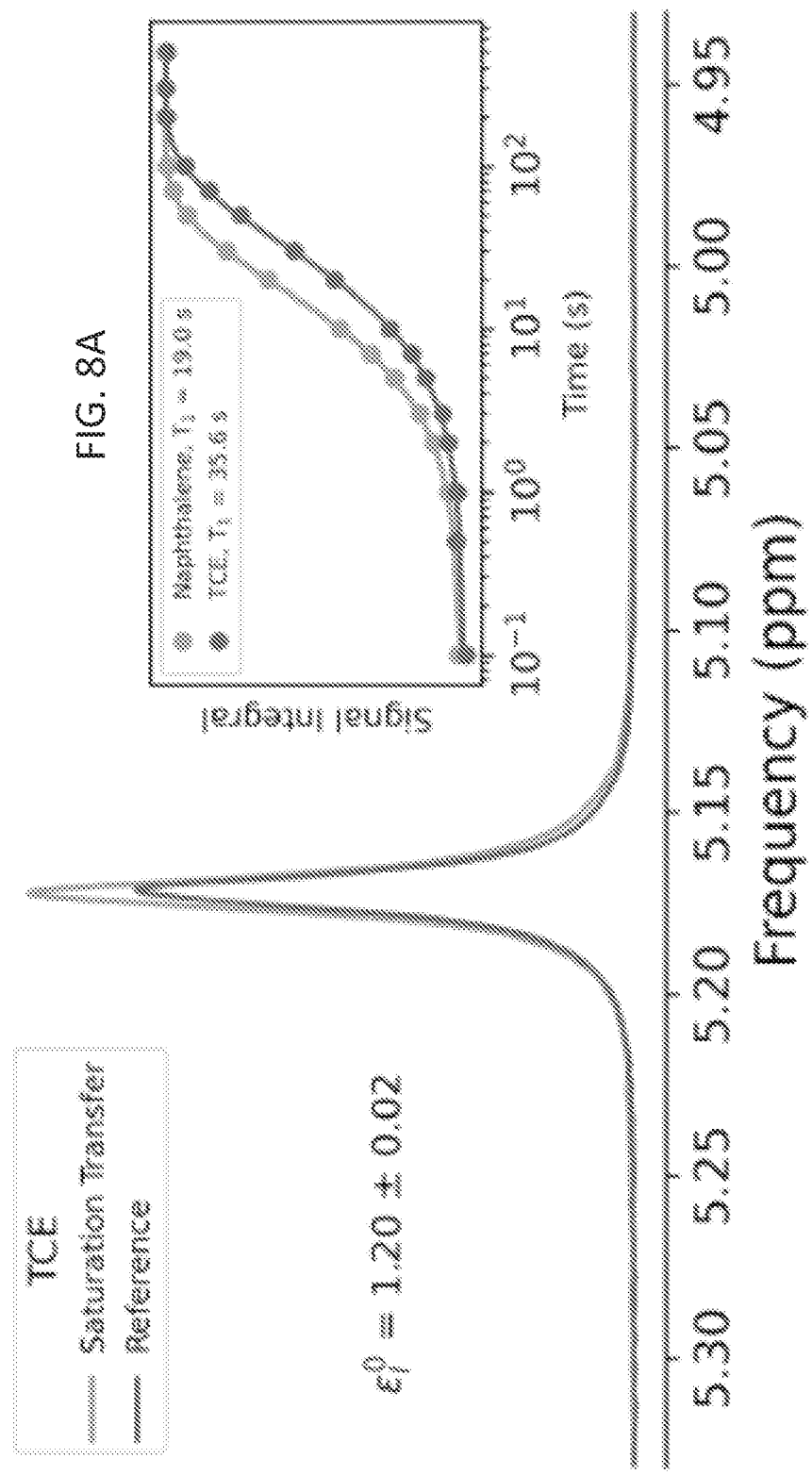
FIG. 8A depicts the measurement of target thermal $T_1=1/\rho$ relaxation times with a standard non-selective inversion recovery sequence for napthalene and 1,1,2,2-trichloroethylene (TCE), in accordance with disclosed embodiments.
FIG. 8B depicts the steady-state saturation transfer of naphthalene to TCE, in accordance with disclosed embodiments.

For thermally polarized samples, the cross-relaxation rate a can be extracted according to Equation (2) using measurements of $\rho_I$ and $\epsilon_I^0$. FIGS. 7A (napathalene as source compound and acetone as target compound) and 8A (napathalene as source compound and TCE as target compound) depict the measurement of target compound thermal $T_1 = 1/\rho$ relaxation times with a standard non-selective inversion recovery sequence. The normalized cross-relaxation rates evaluated from the thermal saturation measurements are here $\sigma(\text{acetone})=(3.7\pm1.5)*10^{-3}$ 1/s and $\sigma(\text{TCE})=(5.6\pm0.6)*10^{-3}$ 1/s, both of which are significantly higher than values of reported rates between hyperpolarized $^{129}$Xe and protons on benzene-$d_5$ and p-nitrotoluene. The difference may be explained by the higher nuclear magnetic moment, higher spin density, and greater accessibility of the naphthalene proton source as compared to dissolved $^{129}$Xe. The steady-state saturation transfer gives intermolecular NOE enhancements of Ep (acetone)=1.05±0.02, as depicted in FIG. 7B, and $\epsilon_I^0(\text{TCE})=1.20\pm0.02$, as depicted in FIG. 8B.

FIGS. 9A (pentacene:napathalene and acetone) and 10A (pentacene:napathalene and TCE) show the polarization buildup and decay at 1.45 T when the pentacene:naphthalene source compound has been optically polarized prior to dissolution in the target solution, which contains 20% v/v pentacene:naphthalene and either 25 mM acetone or 100 mM TCE in $CDCl_3$. While the acetone concentration differs between thermal and hyperpolarized experiments, this is not likely to affect the estimated cross relaxation rate because the pentacene:napathalene concentration is much higher than either target compound concentration, so the source concentration effectively determines the average intermolecular separation in solution. The polarization transfer curves are generally consistent with the characteristic profile expected from Equation (1), though there is some deviation at short times. In order to obtain better agreement, the fitting function may be modified to include an offset time $t_0$ and a stretching factor $\beta$ to Equation (1) to thereby obtain Equation (3):

$$\epsilon_I^{hp}(t) = -\epsilon_S^{hp} \frac{\sigma}{\rho_I - \rho_S} \left( e^{-\rho_S(t-t_0)^\beta} - e^{-\rho_I(t-t_0)^\beta} \right) \quad (3)$$

Figure 10A:
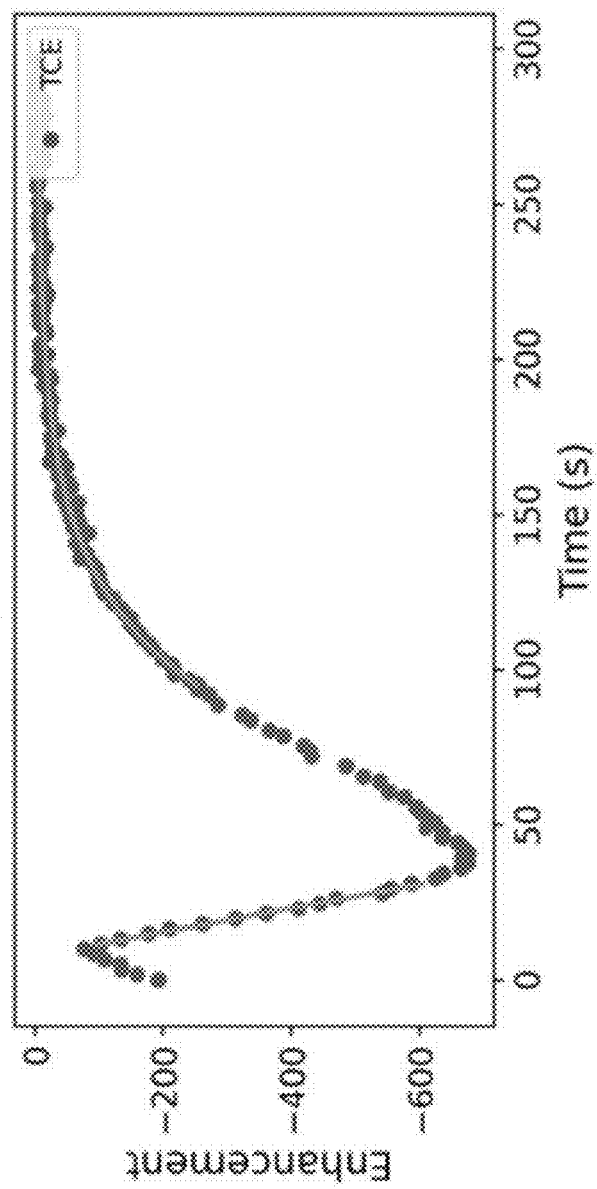
FIG. 10A depicts polarization buildup and decay for TCE at 1.45 T when the naphthalene source has been optically polarized prior to dissolution in the target solution, in accordance with disclosed embodiments.
Figure 10B:
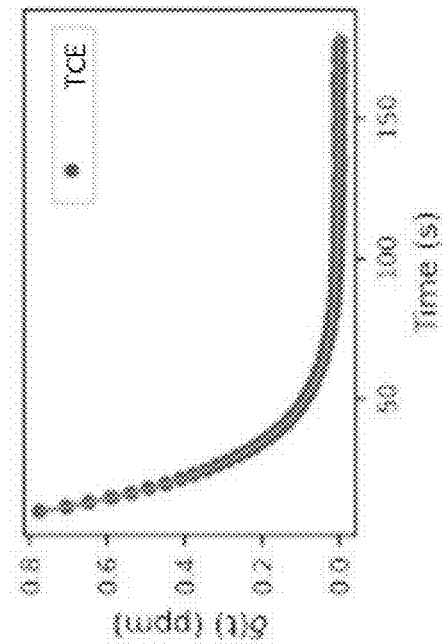
FIG. 10B depicts frequency shifts of the resonances for TCE, in accordance with disclosed embodiments.

The source compound polarization in solution at the start of the NOE buildup may be estimated based on the frequency shifts of the proton NMR resonances according to $$P = -\frac{12 B_0}{\mu_0 \hbar \gamma_I N} \delta * 10^{-6},$$

as described herein and as shown in FIGS. 9B and 10B. Such estimation yields (11.18±0.06)% initial source compound polarization for the acetone experiment and (3.461±0.006)% source compound polarization after 20 seconds for the TCE experiment. Fitting Equation (3) (and excluding the first data point) yields $\sigma=(3.62\pm0.04)*10^{-3}$ 1/s for acetone, with zero time offset and stretching factor $\beta=0.980\pm0.003$. For TCE, the fit (excluding the first seven points) yields $\sigma=(5.70\pm0.07)*10^{-3}$ 1/s with time offset $t_0=(20.9\pm0.3)$ s and stretching factor $\beta=1.022\pm0.003$. The cross-relaxation rates agree with the thermal measurements, though the physical origins of the time offset and slightly compressed exponential factor for the TCE fit are currently unclear.

In another experiment, a 38 milligram (mg) pentacene: naphthalene crystal was polarized to ~25%$^1$H polarization in an optical polarizer. Following the polarization, the crystal was transferred in a transport system and placed in the mixing-dissolution chamber. In the chamber the crystal was dissolved and mixed in DMSO-d6 (99.96%) solvent including 100 mM caffeine and a similar amount of acetone for 8 seconds. The mixture was transferred to a 60 megahertz (MHz) Spinsolve spectrometer for measurement. A selective Gaussian pulse centered around 3.2 ppm was used in order to significantly reduce the signal from the naphthalene nuclear spins. Hyperpolarized peaks from acetone, caffeine, and residual DMSO protons were observed. NMR spectra were taken every −10 seconds. The first spectrum was taken −12 seconds after the end of the mixing. The enhancement for acetone and caffeine was between 120 and 170.

Optimized Detection and Nmr Spectra

As described herein with regards to FIG. 1, the combined source and target compounds can be used in an NMR spectroscopy or MRI application. In some embodiments, the source compound NMR signal can be selectively reduced to permit an improved detection of the target compound signal. This selective reduction can prevent the NMR signal generated by the highly concentrated and polarized source compound from masking the NMR signal generated by the target compound. Absent such selective reduction, target compounds having NMR spectral features (e.g., peaks) that overlap with NMR spectral features of the source compound may be difficult to identify or characterize.

Consistent with disclosed embodiments, selective reduction of the source compound NMR signal can be achieved through reduction of the polarization of the source compound. Such a reduction can be achieved through selection of the source compound, selection of a particular pulse sequence for acquiring an NMR spectrum, or post-processing of the acquired NMR spectrum.

In some embodiments, the source compound can be selected to include at least one fast-relaxing atom (e.g., deuterium, which has a short relaxation time in both low and high magnetic fields). The solution containing the source compound can be placed in an ultralow magnetic field (e.g., lower than 1 uT, lower than 100 nT, or lower) in which the Larmor frequency difference between source atom spins and fast-relaxing atom spins is sufficiently small (e.g., smaller than 10 Hz, or smaller than 1 Hz, or less). Coupling between the source atom spin and the fast-relaxing atom spin can then cause selective relaxation of the source atom. In some embodiments, the solution containing the source compound can be diabatically transferred to the ultralow field, thereby inducing the relaxation of the source atom.

In some embodiments, relaxation of the source atom spins through coupling with the fast-relaxing atom spins can be enhanced using RF irradiation. For example, such RF irradiation can establish a Hartmann-Hahn resonance in the rotating frame between the source atom spins and fast-relaxing atom spins. As an additional example, INEPT pulse sequences can transfer polarization between the source atom spins and the fast-relaxing atom spins. For example, the source compound can be at least partially deuterated and the target compound non-deuterated. Enhanced relaxation due to the interaction with deuterium spins will selectively affect the at least partially deuterated source compound and enable reducing the masking effect of the source molecules on the NMR spectrum.

In some embodiments, a pulse sequence can be selected to reduce the source compound polarization or signal according to any suitable NMR solvent suppression technique. In some embodiments, a selected pulse sequence can be dependent on the specific J coupling of the polarized spins of the source compound. For example, when the source compound includes polarized $^1$H nuclear spins with the same chemical shift (e.g., when the source compound was polarized using PHIP or SABRE), S2M or iSLIC pulses can be applied, converting the $^1$H nuclear spins to electron spins, thereby reducing the $^1$H nuclear spin polarization. Use of such a pulse sequence can reduce the polarization of the source compound, and thus the detected source compound signal. In some embodiments sequences utilizing selective pulses are used.

In some embodiments, the NMR spectrum can be post-processed to correct for the magnetic field produced by the high magnetization of the source compound. This magnetic field can create a significant drift in the target and source atom resonances, and therefore the frequencies of the detected peaks. For a long cylinder magnetized transverse to its symmetry axis, the magnetic field within a small spherical cavity inside the cylinder is $B_M = \mu_0 M/2 - 2\mu_0 M/3 = -\mu_0 M/6$, with nuclear magnetization $M = NPh\gamma_I I$, where N is the number density of nuclear spins, P is the spin polarization, h is the reduced Planck constant, and $\gamma_I$ is the nuclear gyromagnetic moment of spins I. The nuclear spin polarization can therefore be determined based on the frequency shift $\delta$ (expressed in ppm):

$$P = -\frac{12 B_0}{\mu_0 \hbar \gamma_I N} \delta * 10^{-6}.$$

For example, when the magnetic field of the spectrometer is 1.45 T, a shift of −1.00 ppm can correspond to a 5.73% proton polarization.

The NMR spectrum can also be post-processed to correct for effects of the source compound signal. Such effects can include a large broad peak centered at the source compound frequency. This broadening can be due to back action of the detection circuit on the source compound spins, which produces negative feedback, referred to in NMR as "radiation damping". In some implementations, positive feedback can be possible when the source is oppositely polarized, as in the so-called "RASER" (radio amplification by stimulated emission of radiation) effect.

The source compound signal can be strong enough to affect other spin species. The relatively short-lived magnetic fields induced by the precessing spins and radiation damping can couple to other spins. Such magnetic fields can act similar to weak RF pulses, inducing a frequency-dependent phase shift on other resonances. These magnetic fields can be related to the radiation-damped signals measured by the spectrometer. As such, the phase of target compound resonances were approximately linearly dependent on the magnitude of the naphthalene signal at the target resonance frequency. In some embodiments, the fit of the source compound signal can be multiplied by a constant to define a frequency-dependent phase correction for other spin species (e.g., spin species associated with the target compound).

The width of the radiation-damped signal can be related to the magnitude of the source compound magnetization and the intensity of the radiation damping itself, so the phase of the target resonance and the width of the radiation-damped signal can be related.

Figure 10C:
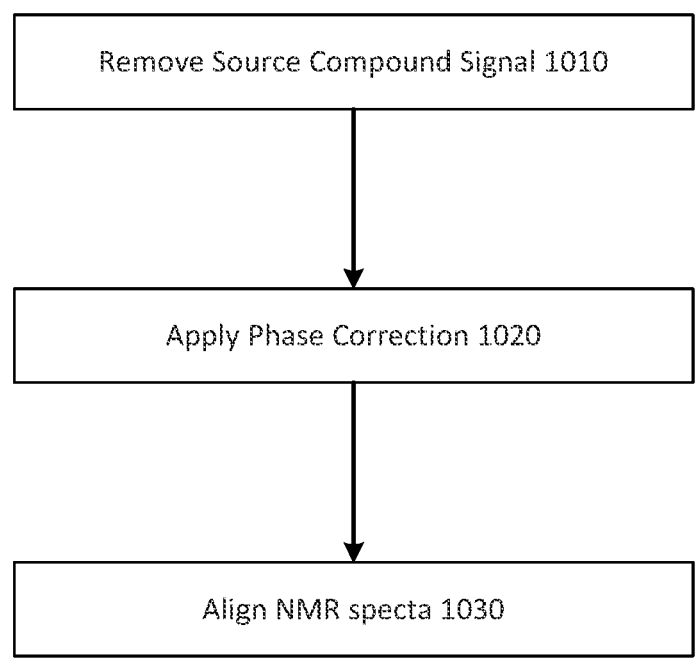
FIG. 10C depicts a post-processing method for separating the effects of the sample magnetic field and the source compound signal from the remainder of the acquired NMR spectrum, in accordance with disclosed embodiments.

FIG. 10C depicts a post-processing method 1000 for separating the effects of the sample magnetic field and the source compound signal from the remainder of the acquired NMR spectrum, in accordance with disclosed embodiments. In this manner, performance of method 1100 can improve detection of the 1D NMR spectrum of the target compound. Method 1100 can be performed using multiple NMR spectra repeatedly or periodically acquired by the NMR spectrometer. As may be appreciated, the NMR spectra generated by method 1000 can be analyzed in the same manner as conventional NMR spectra. In some embodiments, the order of operations in method 1000 can be changed. For example, the phase shift due to the source compound magnetization can be determined prior to subtracting the source compound signal (e.g., step 1030 can be performed prior to one or more of steps 1010 and 1020).

In step 1010, the source compound signal can be removed from each acquired NMR spectrum, consistent with disclosed embodiments. In some implementations, the source compound signal can be fit to a complex Lorentzian (or sum of Lorentzians) lineshape. Such a Lorentzian may have the following formula:

$$L(v, v_0, \sigma, A, \theta) = Ae^{i\theta} \frac{-i(v-v_0)\sigma + \sigma^2}{\pi\sigma((v-v_0)^2 + \sigma^2)} \tag{4}$$

Figure 10D:
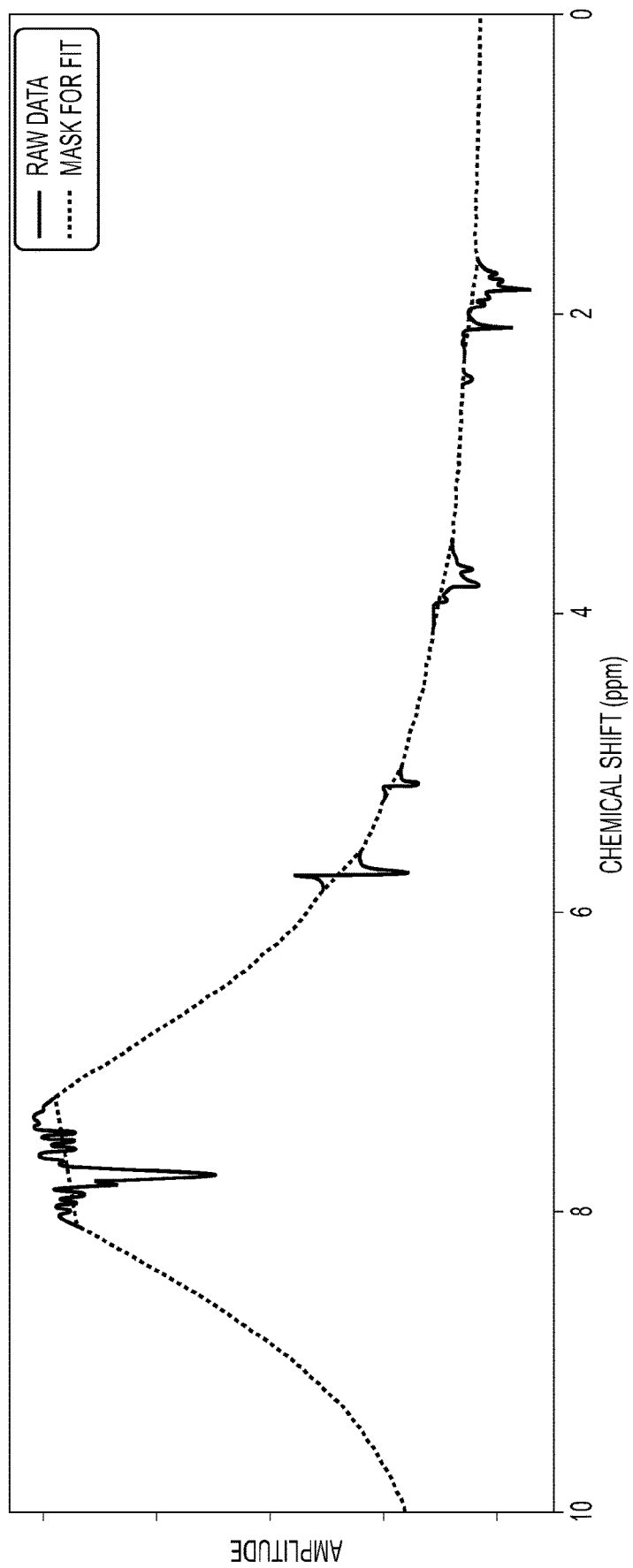
FIGS. 10D to 10K depict the effect of steps of the method of FIG. 10C on exemplary acquired NMR spectra, in accordance with disclosed embodiments.
Figure 10E:
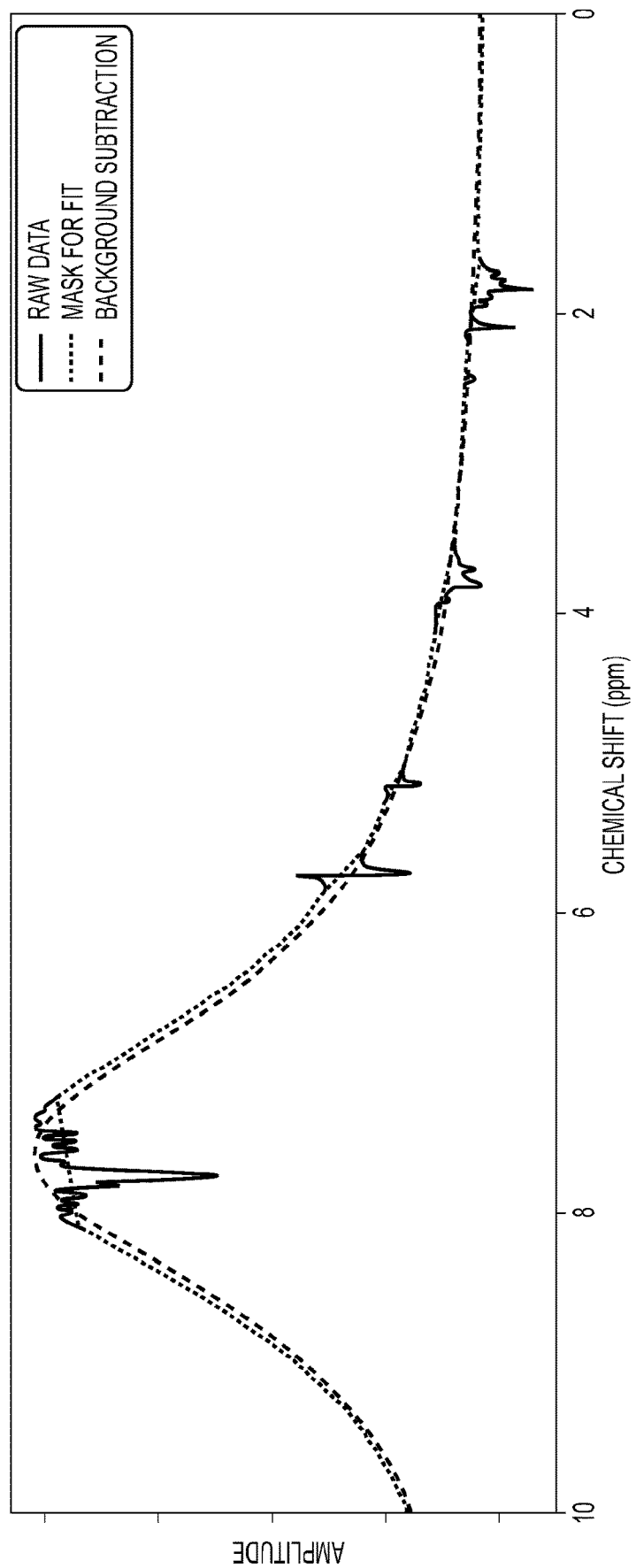
Figure 10F:
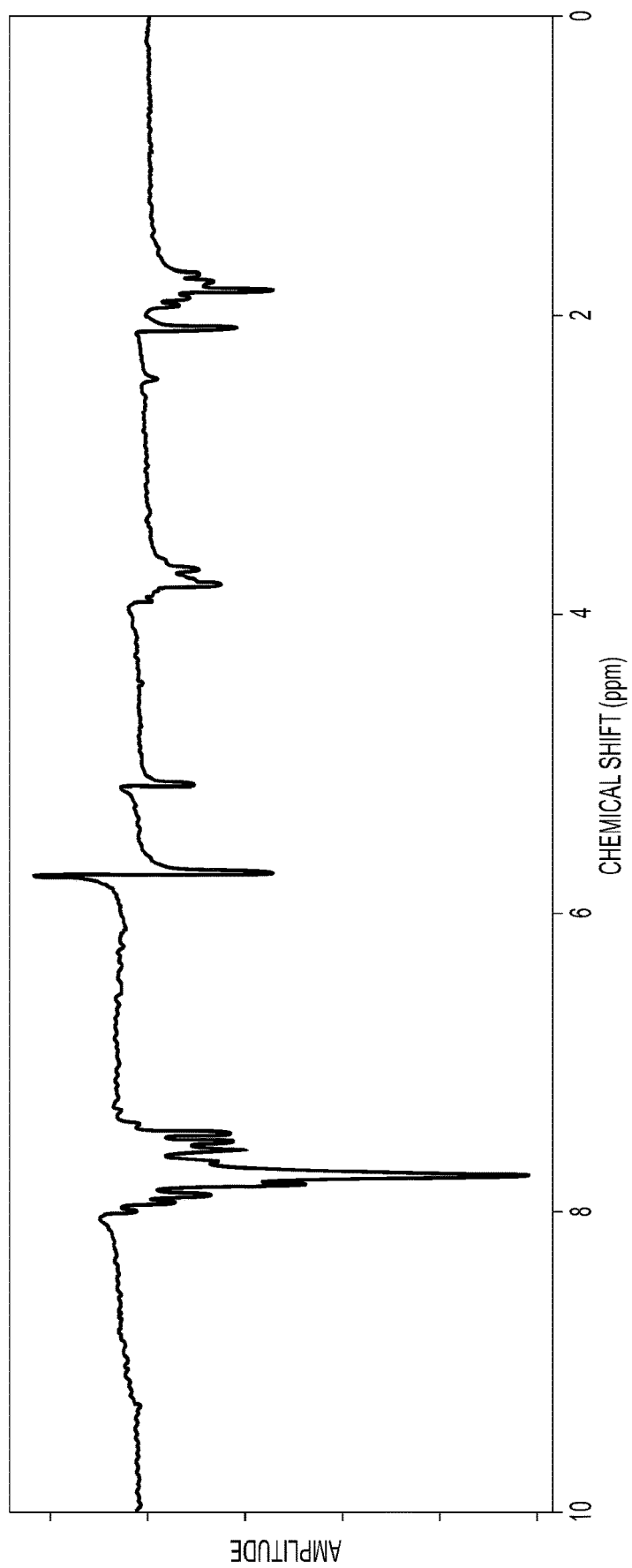

FIG. 10D depicts an exemplary spectrum with the masked data used for the fit, where the peaks from target molecules have been excluded from the calculation of the fit. FIG. 10E depicts the complex Lorentzian fit. The source compound lineshape can be subtracted from the NMR spectrum to yield the spectrum depicted in FIG. 10F. Any residual distortion of the NMR spectrum baseline can be corrected using a moving average or other standard techniques.

In step 1020, a nonlinear phase correction can be applied based on the fit of the source compound signal, followed by standard zero- and first-order phase adjustment. In addition to the standard zero- and first-order phase adjustment, a second-order correction can be estimated by multiplying the normalized Lorentzian (A=1) of the source background by a constant $\varphi_2$. The phased, background-subtracted spectrum is given by $\varphi S(v)$, where $S(v)$ is the background subtracted spectrum and cp is the phase correction including zero, first, and second order terms:

$$\varphi = \exp[-i(\varphi_0 + \varphi_1 v + \varphi_2 L(v, v_{0bg}, \sigma_{bg}, \theta_{bg}, A=1))] \tag{5}$$

Figure 10G:
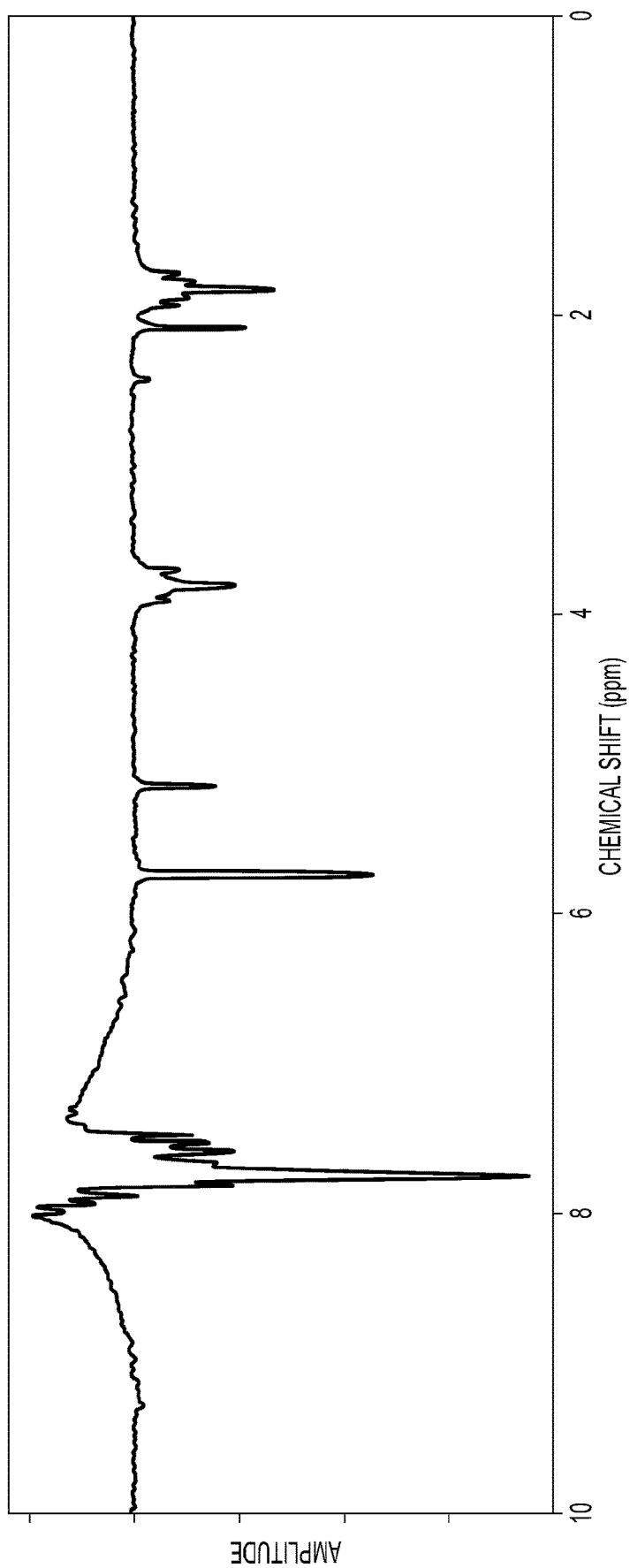
Figure 10H:
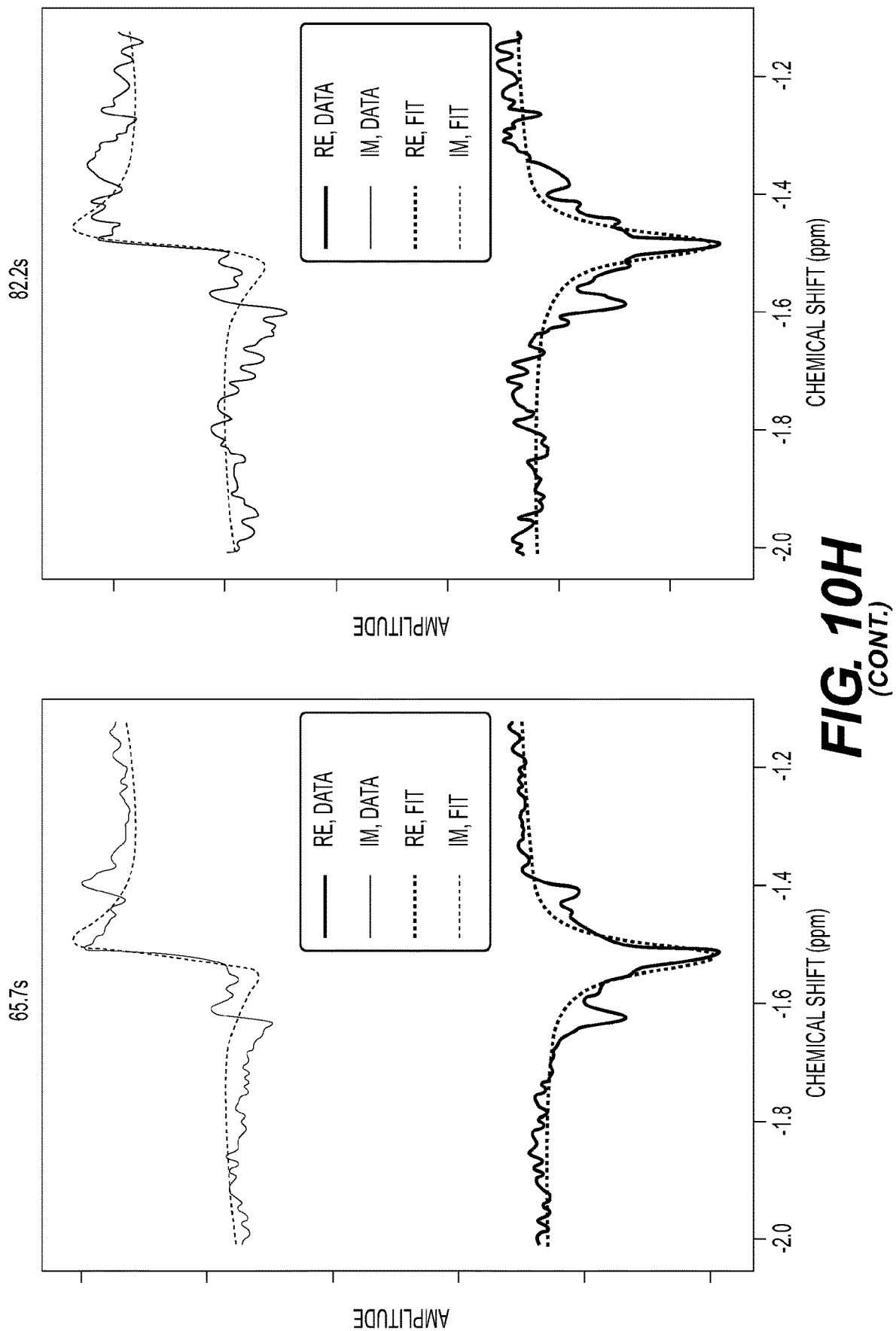

Applying the zeroth-, first- and second-order phase corrections give the result of FIG. 10G, where the baseline is mostly flat and only the narrow features of the naphthalene source signal remain.

Figure 10I:
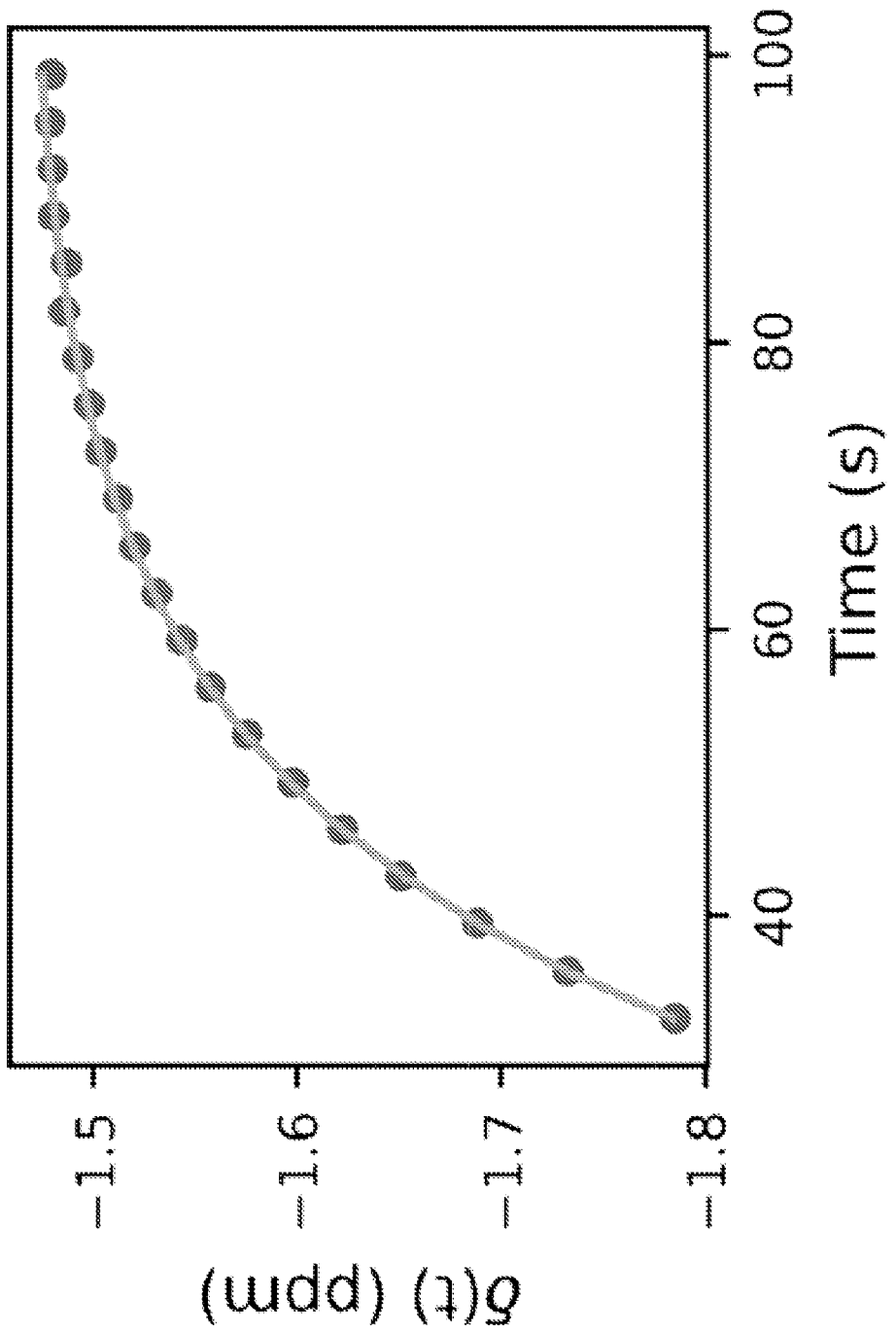
Figure 10J:
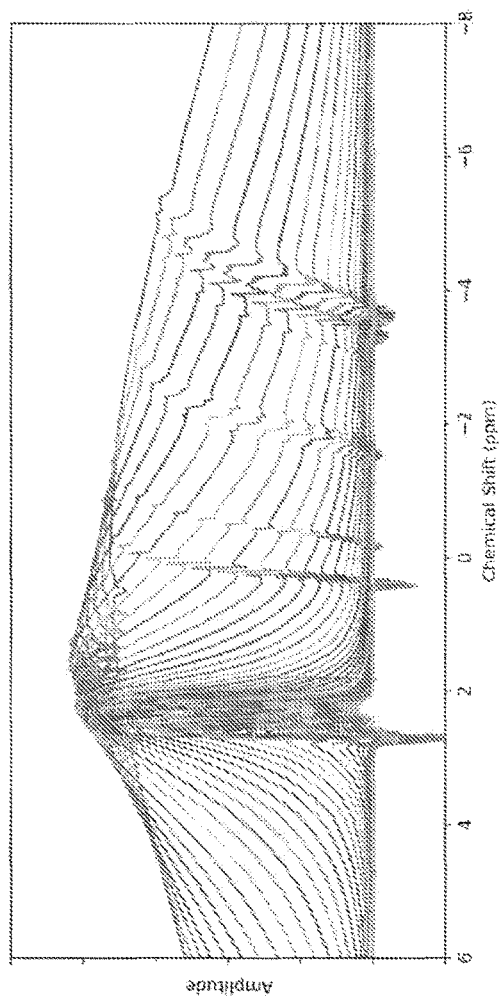
Figure 10K:
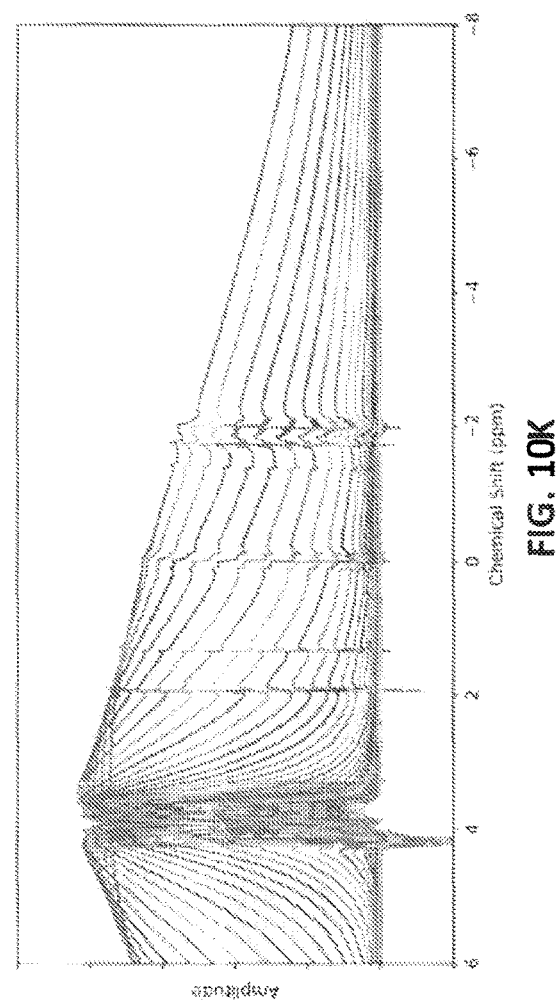

In step 1030, the NMR spectra can be aligned, consistent with disclosed embodiments. In some implementations, a complex Lorentzian (or sum of Lorentzian) lineshape can be fitted to a target compound signal for each NMR spectrum. In the example shown in FIG. 10H, a complex Lorentzian is fit to the higher frequency peak for THF. Examples of this fit are shown for times 32.9, 49.3, 65.7, and 82.2 seconds. The real and imaginary components are labeled in each plot. The center frequencies for each target compound lineshape can be extracted. These center frequencies can then be fitted to a decaying exponential, as shown in FIG. 10I, to find the exponential decay in the phase shift due to the decaying naphthalene source compound magnetization over time. Alternatively, the center frequencies for the source compound lineshapes from step 1010 can be extracted. In either implementation, the decaying exponential can define the frequency shifts necessary to align the NMR spectra. When the source compound lineshapes are used to determine the frequency shifts, some additional manual alignment adjustments can be performed. Once the phase shift for each spectra has been determined, each spectra can be shifted by the determined amount to align the spectra, correcting the chemical shift axis of each spectrum. FIG. 10J shows the spectra prior to correcting the chemical shift axis, while FIG. 10K shows the spectra following correction of the chemical shift axis.

In some embodiments the radiation damping can be utilized to enable several polarization transfer and detection repetitions. Due to the very high magnetization of the source compound, following an excitation pulse the radiation damping rapidly rotates the source magnetization/polarization back to the z axis, preferably in less than 100 ms, 50 ms, 30 ms, 10 ms, 5 ms. As this rate can be faster than the rate of source compound decoherence ($T_2$ or $T_2^*$), a significant amount of the source polarization is maintained following the excitation pulse, even if the excitation pulse angle was 90 degrees. Thus, a large signal can be acquired from the target molecules without a large loss of source compound polarization. This can be utilized for repeated measurements before the source compound relaxes back to thermal equilibrium, enabling signal averaging or multi-dimensional spectroscopy.

In some embodiments the long relaxation time of the source compound can be used for detecting signals of target compounds with short relaxation times, for example less than 10 seconds, less than 5 seconds, less than 2 seconds, less than 1 second, less than 500 ms, less than 200 ms, less than 100 ms, less than 50 ms, less than 10 ms, or less. These target compounds are typically very difficult to polarize with methods where the polarization occurs outside of the NMR spectrometer such as dissolution DNP, due to fast relaxation during the transport of the molecules to the NMR spectrometer and detection. In accordance with disclosed embodiments, however, as the target compound can remain in constant NOE interaction with the source compound, target compound polarization buildup can remain for the relaxation time of the source molecule, thereby enabling the detection of polarization in fast-relaxing target compounds. In addition, as the polarization buildup maximum value may be limited by a short relaxation time of the target compound, several excitation pulses with close to maximum polarization buildup can be used within the longer relaxation time of the source compound, enabling signal averaging or multi-dimensional spectroscopy. In some embodiments, ultrafast 2D sequences can be used for two-dimensional spectroscopy, as described in "Ultrafast 2D NMR: an emerging tool in analytical spectroscopy" by P. Giraudeau and L. Frydman, which is incorporated herein by reference in its entirety for all purposes.

Separation of Source and Target Compound

As described herein with regards to FIG. 1, following polarization transfer, the target compound can be separated from the source compound. In some embodiments, such separation step can produce a mixture including the target compound and some trace concentration (e.g., less than 1 mM, 500 micromolar (04), 200 µM, 100 µM, 50 µM, 20 µM, 10 µM, 5 µM, 2 µM, 1 µM, 500 nanomolar (nM), 200 nM, 100 nM, 50 nM, 20 nM, 10 nM, 5 nM, 2 nM, 1 nM, 500 picomolar (pM), 200 pM, 100 pM, 50 pM, 20 pM, 10 pM, 5 pM, 2 pM, or 1 pM) of the source compound remain in the mixture. In some embodiments, such separation can include removal of at least 90% (e.g., removal of at least 99%, 99.9%, 99.99% or more) of the source compound from a mixture of the source and target compounds.

Consistent with disclosed embodiments, the source compound can be unsuitable for use in certain NMR spectroscopy or imaging applications. Separation of the source and target compounds can enable use of the resultant mixture in such applications. For example, the source compound can be or include non-biocompatible material, while the target compound can be biocompatible. Following the polarization transfer, the polarized biocompatible target compound can be separated from the non-biocompatible compound, producing a polarized biocompatible resultant mixture. The resultant mixture can be used as a magnetic resonance probe. As a further example, the target compound can be used to detect tissue metabolism in vitro or in vivo (e.g., hyperpolarized MRI application). For such applications, toxicity, biocompatibility, or regulatory requirements may necessitate separation of the source compound from the target compound. Additionally, process control and result reproducibility requirements may necessitate separation of the source compound from the target compound. As an additional example, the resultant mixture could be used in applications (e.g., NMR spectroscopy) in which the magnetic resonance signal of the source compound might otherwise mask the magnetic resonance signal of the target compound, making distinguishing between the two signals difficult.

Consistent with disclosed embodiments, separation of the source and target compounds can be performed in close proximity to an MRI or NMR device, as the relaxation time of the target compound may be short (e.g., on the order of a few minutes or several seconds). In some embodiments, the target compound can be used (e.g., injected or probed) in the liquid state. In such embodiments, the mixture of source and target compounds can be dissolved before the extraction of the target compound. In some embodiments, the dissolution step can be performed by heating the mixture or by introducing an additional solvent which dissolves the target compound. In various embodiments of the invention, the compound can be separated from the solution by filtering out particles of the compound (e.g., using mechanical filtration with commercial sterility filters, or the like) or by centrifuging the mixture and removing the particles of the compound.

When the source and target compounds are solutes in a solution, the compound can be removed from the solution using liquid-liquid extraction, high-performance liquid chromatography (HPLC) methods (e.g., for separation of polar and non-polar molecules), introduction of an agent that undergoes a chemical reaction with the compound that enables a separation route, or other suitable methods. Separation of the source and target compounds can be achieved using methods similar to the separation of the source compound from hydrogenation catalysts or reaction byproducts (e.g., sidearms, or the like) when using PHIP, PHIP-SAH or SABRE polarizations methods, as described herein. For example, when the source compound dissolves better in the organic phase and the target compound in an aqueous phase, a liquid-liquid extraction between aqueous and organic phases can facilitate fast purification of the target compound. In some embodiments, one or more quick iterations of liquid-liquid extraction can be performed, depending on the required purity of the target compound. In various embodiments, liquid-liquid extraction can be performed in less than 2 minutes, 1 minute, 20 seconds, 10 seconds, 5 seconds, or 1 second. In some embodiments, liquid-liquid extraction can be performed as an additional purification step following other extraction and separation methods.

Exemplary Phip Polarization and Transfer Device

Figure 11:
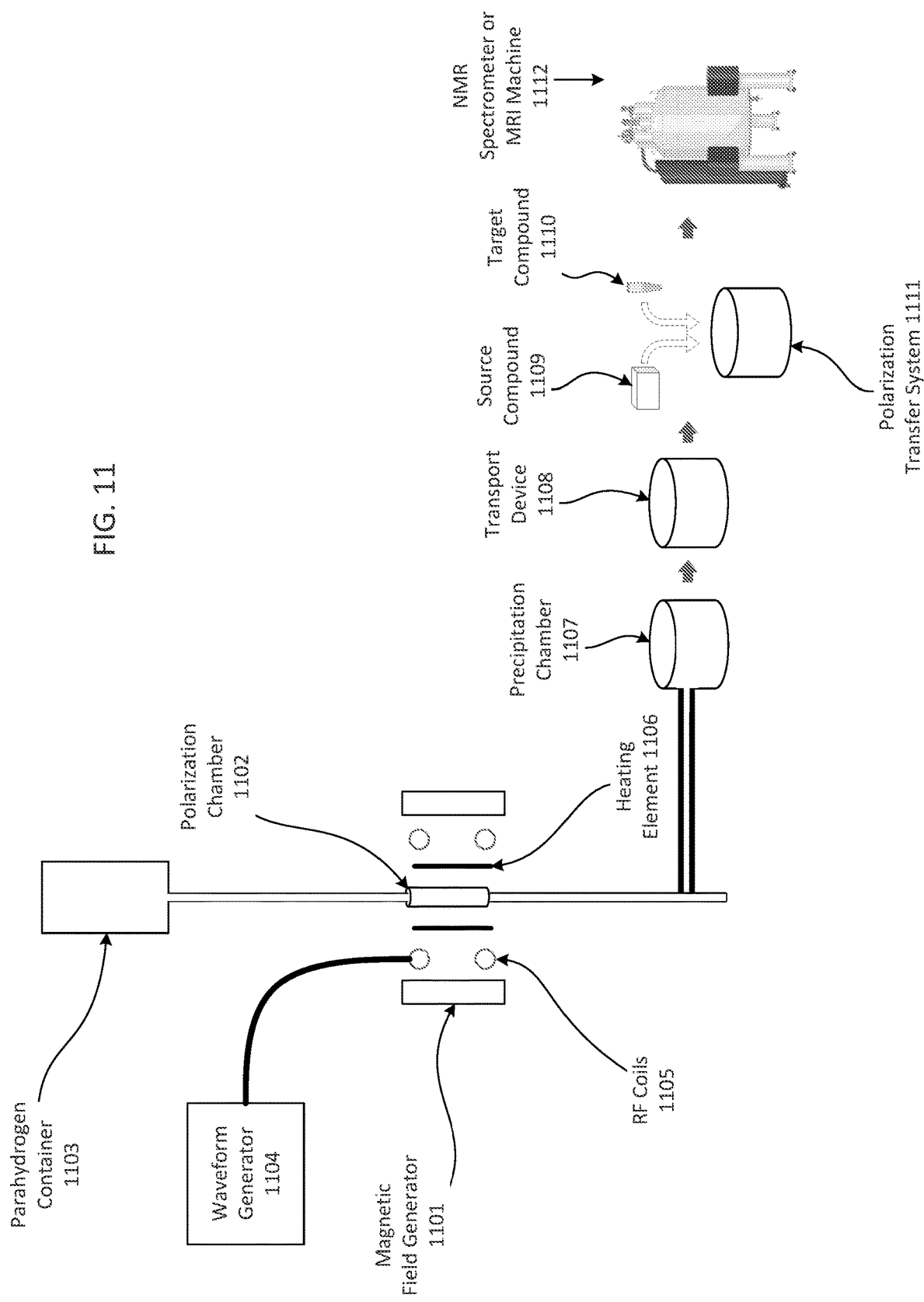
FIG. 11 depicts an exemplary PHIP precipitation system and process, consistent with disclosed embodiments.

FIG. 11 depicts an exemplary PHIP precipitation system and process, consistent with disclosed embodiments. Magnetic field generator 1101 (e.g., a permanent magnet, permanent magnet array, or electromagnet) can be configured to produce a magnetic field of at least about 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, or less, or within a range defined by any two of the preceding values, such as between 10 mT and 5000 mT. In some embodiments, the magnetic field produced by magnetic field generator 1101 can have a magnetic field inhomogeneity of greater than 1 ppm and less than 1000 ppm over a volume of 1 milliliter (mL), 2 mL, 5 mL, 10 mL, 20 mL, 50 mL, 100 mL, or more. The magnetic field inhomogeneity may be measured as the variance of the magnetic field over the volume, or according to any other statistical metric. In some embodiments, magnetic field generator 1101 can produce a magnetic field having the aforementioned inhomogeneity without active shimming.

Polarization chamber 1102 can be configured to contain the solution. In use, a precursor to the source compound can be dissolved in the solution and then subjected to a chemical reaction with parahydrogen (e.g., parahydrogenated), to form a parahydrogenated precursor. In some embodiments, parahydrogen may be bubbled into the solution through a connection (e.g., a gas line or the like) to parahydrogen container 1103. In some embodiments, parahydrogenation can be performed outside polarization chamber 1102 (and optionally outside the magnetic field established by magnetic field generator 1101). For example, in a separate parahydrogenation chamber (not shown in FIG. 11) the parahydrogen can be bubbled into the solution through a gas line, or the solution can be sprayed into a parahydrogen environment through a liquid transport line. Waveform generator 1104 may produce RF pulses (or audio-frequency pulses in relatively low magnetic fields), which can be applied to polarization chamber 1102 using RF coils 1105. Waveform generator 1104 can be or include an arbitrary waveform generator, and can produce a sequence of RF pulses suitable to conversion of spin order to nuclear polarization in the parahydrogenated precursor. In some embodiments, RF coils 1105 may be, be connected to, or include an NMR probe for performing NMR measurements. Such NMR measurements can be used for monitoring and quality control of source compound polarization. Heating element 1106 can be configured to control the temperature inside polarization chamber 1102. For example, for improved hydrogenation, the solution temperature may be elevated above 30° C., 40° C., 50° C., 60° C., 70° C., 80° C., 90° C., 100° C., or greater temperatures. In some embodiments, heating element 1106 utilizes optical, microwave, or RF energy to control the temperature. In some embodiments, heating element 1106 utilizes temperature-controlled flowing air to control the temperature.

Precipitation chamber 1107 can be configured to separate the polarized source compound from any hydrogenation catalysts or reaction byproducts (e.g., sidearms, or the like). In use, the solution containing the polarized source compound can be automatically, semi-automatically, or manually transferred to precipitation chamber 1107. Precipitation can be initiated in precipitation chamber 1107 using any of the methods described herein. For example, a compound can be added to the solution to initiate precipitation. In some embodiments, the compound can be a base. When the polarized parahydrogenated precursor is an ester of the source compound, the added compound can cleave the ester and initiate the precipitation of the polarized source compound. Precipitation chamber 1107 can be configured to enable separation of the precipitate from the supernatant, thus allowing separation of the polarized source compound from the catalysts and solvent (e.g., organic solvent) used for the hydrogenation and polarization of precursor to thereby form the source compound. Furthermore, such precipitation can enable the concentration of the source compound to be changed (e.g., from low concentrations suitable for polarization of the source compound to high concentrations suitable for transfer of polarization to the target compound using NOE).

In some embodiments, a further purification step can occur in the precipitation chamber 1107, during which concentration of the hydrogenation catalyst may be reduced from the 0.1-100 mM range to less than 1 µM, 500 nM, 200 nM, 100 nM, 50 nM, 20 nM, 10 nM, 5 nM, 2 nM, 1 nM, or less. Such a reduction may be accomplished by washing the precipitated polarized source compound with a biocompatible solvent. The biocompatible solvent can be selected such that the precipitated polarized source compound is insoluble in this solvent.

In some embodiments, the hydrogenation of new precursor molecules, polarization transfer, and precipitation steps may be performed repeatedly in a predetermined time period. In some embodiments, the predetermined time period may be within a relaxation time of the nuclear spin of interest in the solid phase. In some embodiments, the hydrogenation, polarization transfer and precipitation steps may be performed rapidly, such as on the order of a couple of minutes or a couple of seconds, to enable collection of a larger volume of solid polarized particles. In some embodiments, these steps may be performed in a continuous flow system. In some other embodiments, these steps may be performed in several discrete steps.

Following the precipitation and purification the hyperpolarized particles may be stored and transported in transport device 1108. The transport device may include a permanent magnet or electromagnet for generating a magnetic field higher than 10 mT. Preferably the transport device includes a coolant for cooling the temperature of the hyperpolarized particles to 273.15K or below, 150K or below, 80K or below, 30K or below. A suitable transport device is described herein with regards to FIG. 13.

Following precipitation and transport, source compound 1109 can be mixed with a solution containing the target compound 1110 in polarization transfer system 1111. In some embodiments, polarization can be transferred from source atoms of source compound 1109 to target atoms of target compound 1110 by SPINOE. In some embodiments, polarization transfer system 1111 can be temperature controlled to increase the polarization transfer efficiency or polarization transfer rate. In some embodiments, the solution containing the source compound and the target compound can then be used by NMR spectrometer or MRI machine 1112 for hyperpolarized NMR or MRI. In some embodiments, the transfer of polarization to the target atoms can be followed by another transfer from the target atoms to a different nuclear spin on the target compound, for example by an INEPT sequence. In some embodiments, polarization transfer system 1111 can be part of NMR spectrometer or MRI machine 1112.

Exemplary Pets Polarization and Transfer Device

Figure 12:
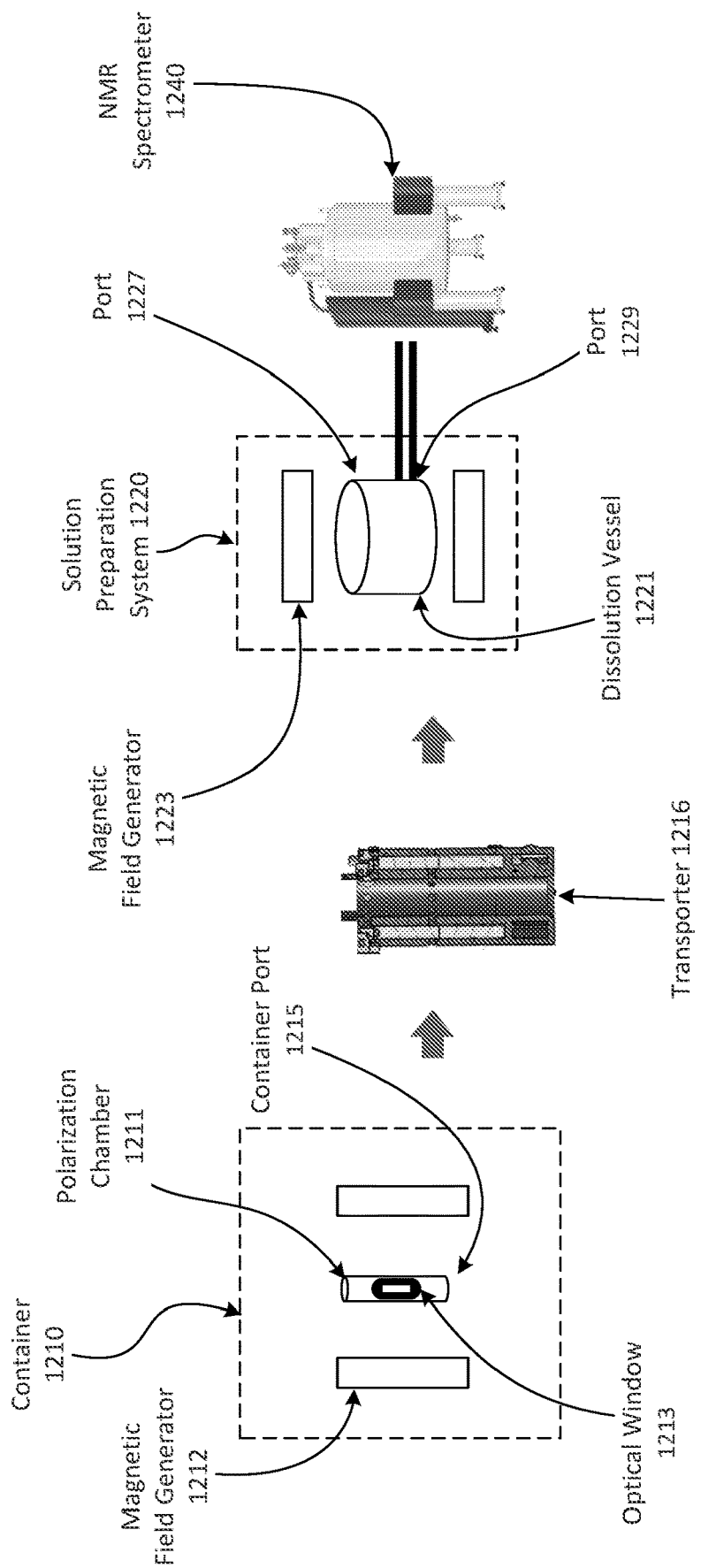
FIG. 12 depicts an overview of a setup and components of a photoexcited triplet state (PETS) polarizer, in accordance with disclosed embodiments.

FIG. 12 depicts the overview of the setup and components of a PETS polarizer, in accordance with disclosed embodiments. The PETS polarizer can include a container 1210 and a solution preparation system 1220. The container 1210 can include a polarization chamber 1211 and a magnetic field generator 1212. The solution preparation system 1220 can include a dissolution vessel 1221, a magnetic field generator 1223, and a processing means 1225.

Figure 13:
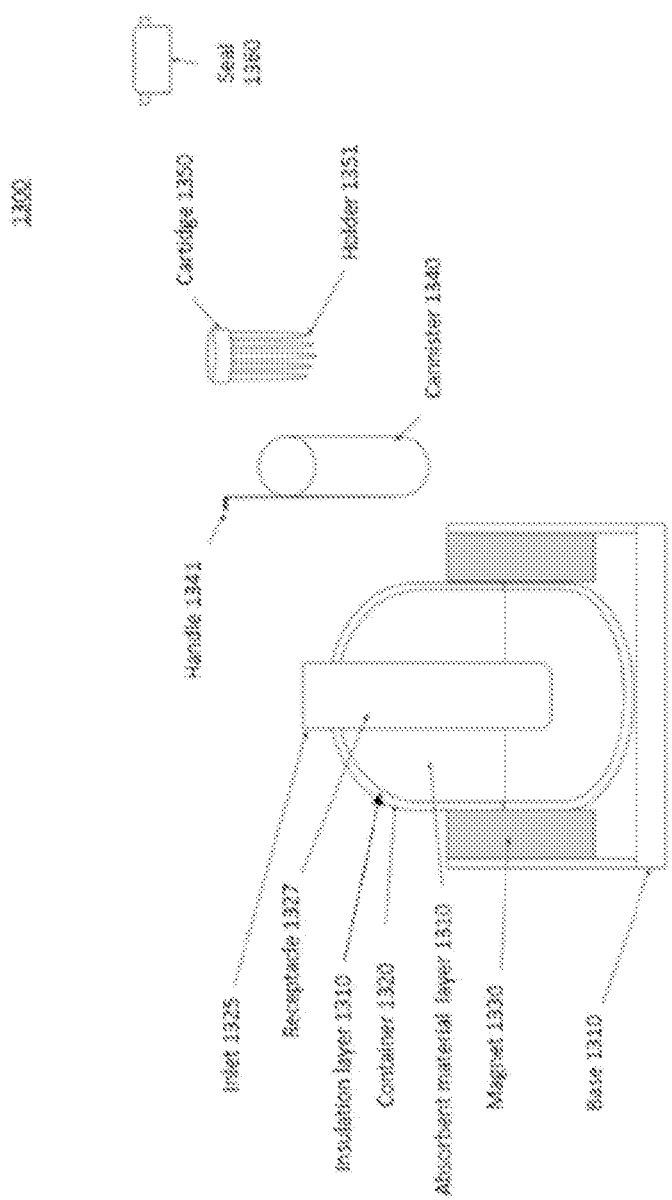
FIG. 13 depicts an exemplary transport system, consistent with disclosed embodiments.
Figure 14:
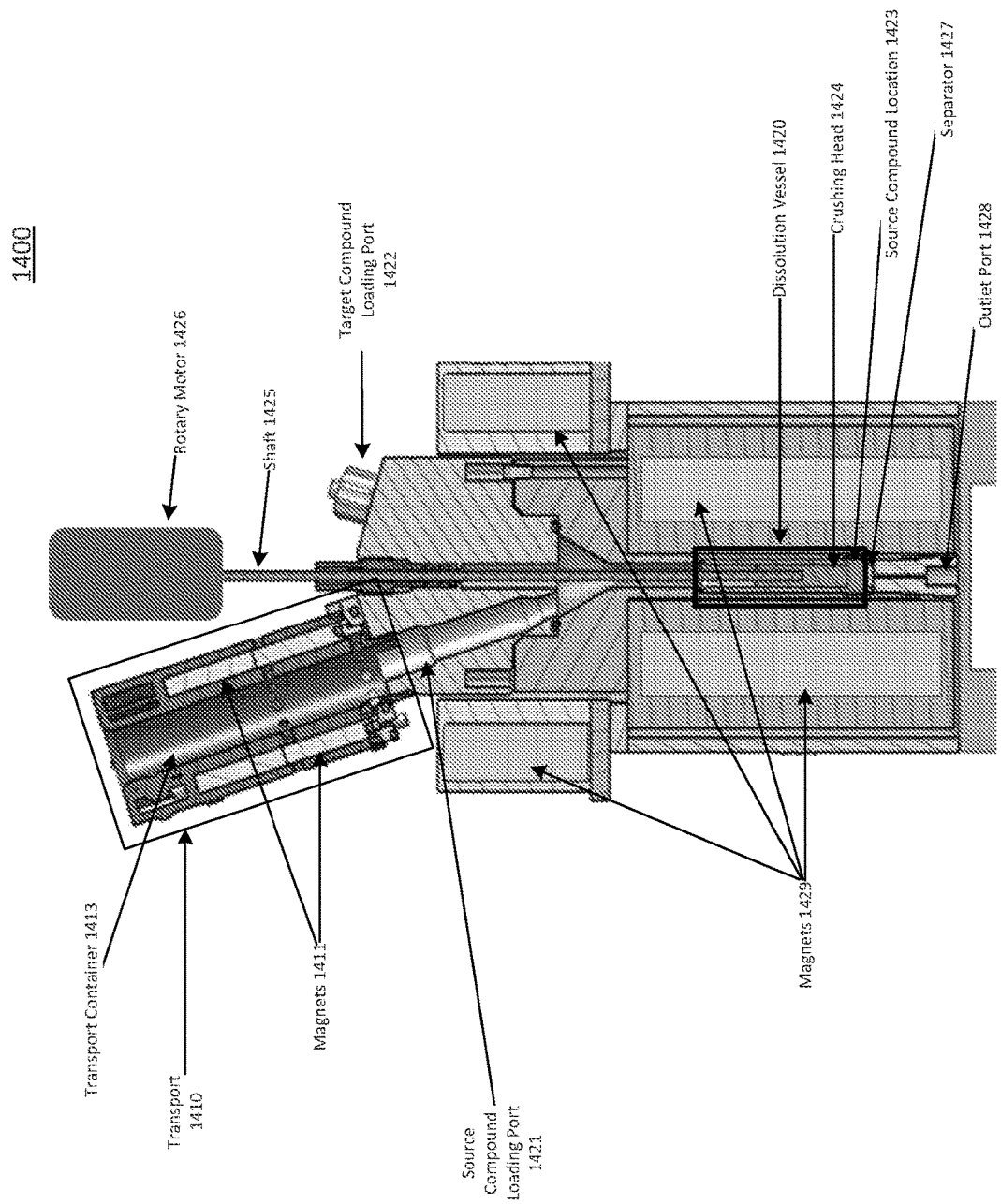
FIG. 14 depicts an exemplary system for automatically combining a solid source compound with a target compound, consistent with disclosed embodiments.
Figure 15:
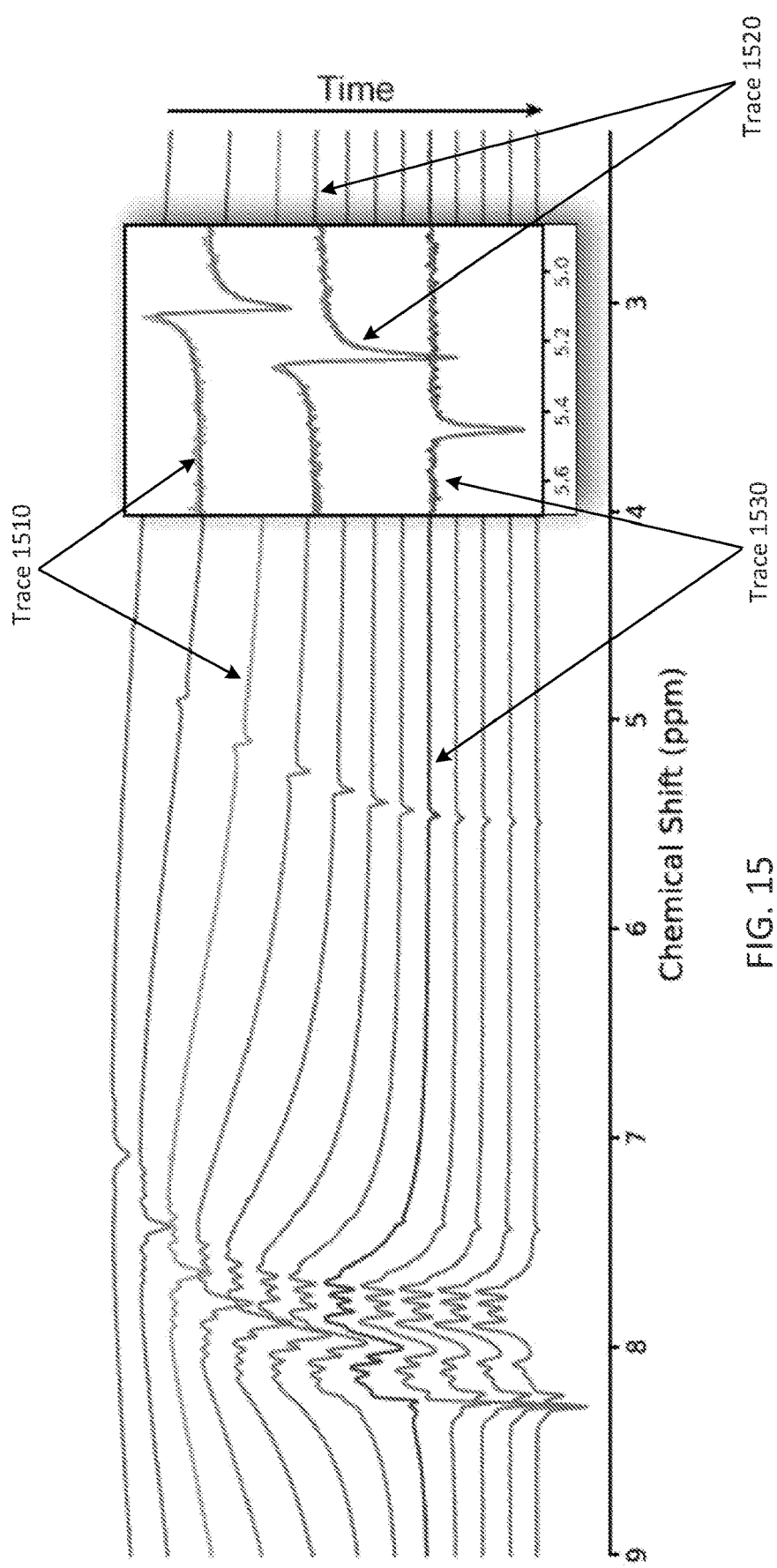
FIG. 15 depicts a series of NMR spectra acquired following injection of a hyperpolarized solution into a spectrometer, in accordance with disclosed embodiments.

Polarization chamber 1211 can be configured to contain the solution in an internal volume of polarization chamber 1211. In use, a source compound comprising at least one PETS moiety can be housed in polarization chamber 1211. In some embodiments, the source compound can be a crystalline host doped with a dopant. In various embodiments, the crystalline host can include at least one of naphthalene, p-terphenyl, or benzoic acid. In some embodiments, the dopant can be pentacene. In some embodiments, polarization chamber 1211 can include at least one optical window 1213. Optical window 1213 can be configured to couple to a light source (not shown in FIG. 12). In use, the light source can provide light for optical polarization of the at least one PETS moiety. Consistent with disclosed embodiments, polarization chamber 1211 can include at least one container port 1215. The at least one container port 1215 can permit the automatic, semi-automatic, or manual passage of the source compound from the internal volume, through the at least one container port, and to a solution preparation system. For example, the source compound can exit polarization chamber 1211 through the at least one container port 1215 into transporter 1216 (e.g., a transporter as depicted in FIG. 13 or 14). Transporter 1216 can be transported to solution preparation system 1220 and the source compound placed within solution preparation system 1220. As an additional example, a manifold or conveyor can transport the source compound (e.g., automatically or semi-automatically in response to user input) from polarization chamber 1211 through the at least one container port 1215 into dissolution vessel 1221.

Magnetic field generator 1213 can at least partially surround the internal volume of polarization chamber 1211. Magnetic field generator 1213 (e.g., a permanent magnet, permanent magnet array, or electromagnet) can be configured to produce a magnetic field of at least about 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, or less, or within a range defined by any two of the preceding values, such as between 10 mT and 5000 mT within the internal volume of polarization chamber 1211. In some embodiments, magnetic field generator 1213 can be or include at least one solenoid. In some embodiments, the magnetic field produced by magnetic field generator 1213 can have a magnetic field inhomogeneity of greater than 1 ppm, 2 ppm, 5 ppm, 10 ppm, 20 ppm, 50 ppm, 100 ppm, 200 ppm, 500 ppm, 1000 ppm, or more, less than 1000 ppm, 500 ppm, 200 ppm, 100 ppm, 50 ppm, 20 ppm, 10 ppm, 5 ppm, 2 ppm, 1 ppm, or less, or within a range defined by any two of the preceding values. In some embodiments, the magnetic field inhomogeneity is measured over a volume of 1 ml, 2 ml, 5 ml, 10 ml, 20 ml, 50 ml, 100 ml, or more. In some embodiments, magnetic field generator 1213 can produce a magnetic field having the afore-mentioned inhomogeneity without active shimming.

In some embodiments, dissolution vessel 1221 can be configured to couple to the at least one container port 1215. In various embodiments, dissolution vessel 1221 be configured to receive source compound transported in transporter 1216 (e.g., a transporter as depicted in FIGS. 13 and 14). In use, dissolution vessel 1221 can receive the source compound (e.g., following passage of the source compound through the at least one container port 1215 and automatic, semi-automatic, or manual transportation of the source compound). Dissolution vessel 1221 can be configured to receive a pressurized gas and solution. Dissolution vessel 1221 can be configured to receive the solution through port 1227. In use, a target compound can be dissolved in the first solution. Dissolution vessel 1221 can receive the pressurized gas from a gas container 1230. The pressurized gas can be an inert gas. In some embodiments, the pressured gas can be nitrogen, argon, or any combination thereof. Consistent with disclosed embodiments, polarization chamber 1211 can include port 1229, which can permit the automatic, semi-automatic, or manual passage of a solution from the dissolution vessel 1221, through port 1229, to an NMR tube. In some embodiments, port 1129 can be coupled to a flow system. In some embodiments, the flow system can be a tube or manifold that permits or causes (e.g., using a pump) the flow of the solution to the NMR tube (which may be inside or outside the bore of an NMR magnet). For example, the solution can flow from port 1129 through a manifold into a tube inside the NMR magnet. In another example, port 1129 can be directly connected to an NMR tube, which can be carried or shuttled (e.g., mechanically, pneumatically, by hand, etc.) into the NMR magnet. The disclosed embodiments are not limited to a particular flow system.

In use, the flow system can be configured to receive the second solution formed by combining the crushed source compound with the solution added to dissolution chamber 1221 and to transport this second solution to NMR tube 1241 (not shown in FIG. 12) located within NMR spectrometer 1240.

Magnetic field generator 1223 can at least partially surround dissolution vessel 1221. Magnetic field generator 1223 (e.g., a permanent magnet, permanent magnet array, or electromagnet) can be configured to produce a magnetic field of at least about 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, or less, or within a range defined by any two of the preceding values, such as between 10 mT and 5000 mT within dissolution vessel 1221. In some embodiments, magnetic field generator 1223 can be or include at least one solenoid.

Processing means 1225 (not shown in FIG. 12) can be disposed at least partially within dissolution vessel 1221. Processing means 1225 can be configured to process (e.g., break, crush, cut, grind, or the like) the source compound into fragments of desired dimensions. In use, processing means 1225 can process the source compound, thereby permitting or speeding dissolution of the source compound in the solution received through the solution port, thereby generating a second solution.

In some embodiments, the processing means can be an ultrasonic probe. In some embodiments, processing means can include a cutting, grinding or crushing head (e.g., a processing head) for mechanical processing the source compound. The processing head can be mechanically coupled to a shaft. In some embodiments, the shaft can be configured to permit motion within the dissolution vessel. In some embodiments, the motion can include motion along the axis of the shaft. The shaft can advance within dissolution vessel 1221, causing the processing head to process the source compound (e.g., against the walls of the dissolution vessel 1221). In some embodiments, the motion can include motion around the axis of the shaft, and/or around a second axis parallel to the axis of the shaft. This motion can cause the processing head to rotate within the dissolution vessel, causing the processing head to process the source compound. In some embodiments, the processing head can force the source compound against a filter (e.g., a frit), such that particles of the source compound less than a certain size pass through the filter. In some embodiments, the shaft can be mechanically coupled to a rotary motor. The rotary motor can be configured to provide the motion to the processing head via the shaft to thereby process the source compound.

Exemplary Transport Device

FIG. 13 describes an exemplary transport device 1300, consistent with disclosed embodiments. In some embodiments, device 1300 can include base 1310, container 1320 and magnet 1330. Device can further include canister 1340, cartridge 1350, and seal 1360.

Base 1310 can be configured to support container 1320. Magnet 1330 can be attached to base 1310 and disposed around container 1320. In some embodiments, magnet 1330 can include multiple magnets spaced around container 1320. Magnet 1330 can be configured to maintain a magnetic field with a strength between 0.1 and 4 Tesla within container 1320 (or within receptacle 1327 in container 1320) when container 1320 is placed within magnet 1330 on base 1310.

Container 1320 can include insulation layer 1321, absorbent material layer 1323, inlet 1325, and receptacle 1327. Insulation layer 1321 can be configured to insulate the inside of container 1320 from the outside environment. Insulation layer 1321 can be any suitable insulation material. Absorbent material layer 1323 can be configured to absorb a liquid coolant. For example, absorbent material layer 1323 can be suitable for absorbing liquid nitrogen or a similar cryogenic liquid. Receptacle 1327 can be a void formed in absorbent material layer 1323 below inlet 1325. In some embodiments, the void can be cylindrical. Inlet 1325 can permit access through insulation layer 1321 to the inside of container 1320.

Container 1320 can be configured to permit a liquid coolant (e.g., liquid nitrogen), to be being poured into the receptacle 1327 and absorbed into the absorbent material layer 1323. So long as sufficient liquid coolant remains, the temperature within the receptacle 1327 will approximate the temperature of the liquid coolant. In some embodiments, container 1320 can be a cryogenic dry shipper container, such as a cryostat (e.g., a Dewar, vacuum flask, or the like).

Cannister 1340 can be configured to support cartridge 1350 within receptacle 1327. In some embodiments, cannister 1340 can include a handle 1341 enabling cannister 1340 to be placed within and removed from receptacle 1327 through inlet 1325. Cartridge 1350 can be configured to hold one or more holders 1351. Cartridge 1350 can be configured and arranged such that each holder 1351 can be separately removable from cartridge 1350. Each holder 1351 can be configured to hold a sample of a polarized compound. Cartridge 1350 can be configured to within the canister and lowered into container 1320. Seal 1360 can be configured to seal the container 1320 and prevent evaporation of the coolant.

In some embodiments, device 1300 may not include base 1310. In such embodiments, magnet 1330 may be disposed within container 1320. Magnet 1330 may be disposed around receptacle 1327. In some embodiments, absorbent material layer 1323 may be disposed between magnet 1330 and receptacle 1327. In various embodiments, absorbent material layer 1323 may be disposed between magnet 1330 and an inner surface of insulation layer 1321. In such embodiments, for example, receptacle 1327 may be a void defined at least in part by the inner surface of magnet 1330.

Exemplary Device for Combining Source and Target Compounds

FIG. 14 depicts an exemplary system 1400 for automatically combining a solid source compound with a target compound, consistent with disclosed embodiments. In some embodiments, system 1400 can perform the role of solution preparation system 1220 of FIG. 12 or polarization transfer system 1111 of FIG. 11.

In some embodiments, system 1400 can include transport container 1410. Transport container 1410 can be configured to store a solid (e.g., crystalline) source compound during transport from a polarizer to system 1400. Transport 1410 can include magnets 1411 (e.g., permanent magnets, electromagnetics, or the like) disposed around a transport container 1413 for maintaining source compound polarization. Magnets 1411 can create a magnetic field within transport container 1413 of at least about 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, or less, or within a range defined by any two of the preceding values, such as between 10 mT and 2000 mT. In some embodiments, transport 1410 can include a temperature control system (e.g., a cryogenic reservoir, Dewar, or other suitable methods) for maintaining a temperature of the source compound.

In some embodiments, system 1400 can include a dissolution vessel 1420. Dissolution vessel 1420 can be connected to a source compound loading port 1421. Source compound loading port 1421 can be connected to transport container 1413 and can provide a channel for the solid source compound within transport container 1413 to move (e.g., fall through gravity and/or be blown by a compressing gas) to source compound location 1423 within dissolution vessel 1420. Target compound loading port 1422 can enable a target compound, a solvent, a solution of the target compound and a solvent, pressurized gas, or a combination or sequence of any of the foregoing, to be added to dissolution vessel 1420. In some embodiments, target compound loading port 1410 can be connected to a manifold, that is in turn connected to a pressurized gas source, target compound or target compound solution container, solvent container, or the like.

Consistent with disclosed embodiments, dissolution vessel 1420 can contain a mechanism for mechanically breaking down the solid source compound into smaller particles for faster dissolution. As depicted in FIG. 14, such a mechanism can be implemented using a crushing head 1424 connected to a shaft 1425 driven by a rotary motor 1426. In some embodiments, rotary motor 1426, shaft 1425, and crushing head 1423 can be advanced and withdrawn within dissolution vessel 1420. In this manner, the source compound can be positioned within source compound location 1423 prior to advancing and rotating crushing head 1424 (e.g., for 1 to 10 seconds, or more), thereby breaking down the source compound. Similarly, crushing head 1424 can be withdrawn prior to adding the target compound or the solution containing the target compound. Alternatively, a solution including the target compound can be added through target compound port 1422 while crushing head 1424 is advanced (e.g., during rotation of crushing head 1424). In such embodiments, the rotation of crushing head 1424 can serve to mix the target solution and the source compound. While depicted with a rotating crushing head 1424 driven by rotary motor 1426 through shaft 1425, the disclosed embodiments are not limited to such an arrangement. In some embodiments, the mechanism for mechanically breaking down the solid source compound can be implemented using a mortar and pestle arrangement or an ultrasonic probe.

Consistent with disclosed embodiments, separator 1427 can be positioned adjacent to source compound location 1423 (e.g., below or around source compound location 1423, or another suitable location). Separator 1427 can be used to separate a solution resulting from the addition to dissolution vessel 1420 of a solvent or a target solution through target compound loading port 1422. Separator 1427 can be a frit, a membrane, filter, or the like. In some instances, separator 1427 can separate dissolved source compound (or additionally dissolved target compound) from solid particles (e.g., undissolved particles of the source or target compound). In some embodiments, the solution can be forced through separator 1427. The solution can be forced through separator 1427 using gas (e.g., Nitrogen gas, argon gas, and/or another suitable inert gas) introduced through target compound loading port 1422. The solution can be forced to outlet port 1428, which can be fluidically connected to dissolution vessel 1420. In some embodiments, there may be a delay (e.g., at least about 1 millisecond (ms), 2 ms, 5 ms, 10 ms, 20 ms, 50 ms, 100 ms, 200 ms, 500 ms, 1000 ms, or more, at most about 1000 ms, 500 ms, 200 ms, 100 ms, 50 ms, 20 ms, 10 ms, 5 ms, 2 ms, 1 ms, or less, or within a range defined by any two of the preceding values) between cessation of rotation by crushing head 1424 and the introduction of gas to force the solution through separator 1427. Such a delay can enable polarization transfer from the source atoms of the source compound to the target atoms of the target compound.

In some embodiments, outlet port 1428 can be connected to an container for collecting the solution (e.g., an NMR tube, or another suitable container), or to the inlet port of an NMR or MRI device. In some embodiments, outlet port 1428 can be connected to an inlet port of the NMR or MM device.

In some embodiments, magnets 1429 can be disposed around or mounted on dissolution vessel 1420 (and optional at least partially around source compound loading port 1421 and target compound loading port 1422, shown in FIG. 14). Such magnets can be permanent magnets, electromagnets, or the like. Such magnets can generate a magnetic field within dissolution vessel 1420 of at least about 1 mT, 2 mT, 5 mT, 10 mT, 20 mT, 50 mT, 100 mT, 200 mT, 500 mT, 1000 mT, 2000 mT, 5000 mT, or more, at most about 5000 mT, 2000 mT, 1000 mT, 500 mT, 200 mT, 100 mT, 50 mT, 20 mT, 10 mT, 5 mT, 2 mT, 1 mT, or less, or within a range defined by any two of the preceding values.

Exemplary Polarization Transfer from Pentacene Doped Napathalene in Solution

Transfer of polarization to target compounds via intermolecular NOE from spin-polarized pentacene-doped naphthalene crystals dissolved in solution was investigated at room temperature and moderate magnetic fields (1.45 T). NMR signals were enhanced by factors between 200 and 1,730 (corresponding to up to 0.86% polarization) for a range of small molecules. The entire polarization process required less than one minute, did not require cryogenics, and resulted in high-resolution NMR spectra due to the absence of paramagnetic contaminants.

Hyperpolarization of Source Molecules

A pentacene-doped naphthalene crystal was optically polarized to 20% to 25% proton polarization. The polarized crystal was then transported at room temperature in a handheld permanent magnet assembly to the polarization transfer device, where it was inserted into a dissolution vessel under inert atmosphere, crushed, and dissolved into a solution of interest. Finally, the sample was injected into a 1.45 T benchtop spectrometer for measurement. For time-dependent studies, small-angle (approximately 1 degree) RF pulses were applied every 3.3 s in order to monitor source and target signals. Alternatively, in order to acquire the maximum signal intensity, a single 90-degree pulse could be applied after waiting for polarization transfer.

The proton spins of naphthalene-h8 were polarized via triplet-DNP (as described in T. Eichorn et al, "An apparatus for pulsed ESR and DNP experiments using optically excited triplet states down to liquid helium temperatures," J. Magn. Reson. 2013, 234, 58-66, which reference is incorporated herein in its entirety for all purposes) in a single crystal doped with deuterated pentacene. The photo-excited triplet state of the latter exhibited a high electron polarization of approximately 90%, largely independent of magnetic field and temperature. Naphthalene was extensively purified by zone-refinement to minimize any contamination, particularly of paramagnetic origin, and to maximize the $T_1$ relaxation time and triplet-DNP yield. The quality of the material was periodically probed during the purification process by means of delayed fluorescence. Naphthalene triplet state lifetimes exceeding 300 ms at room temperature were obtained. Pentacene-doped naphthalene crystals were grown with the self-seeding Bridgman method (as described in S. Selvakumar et al, Growth of high-quality naphthalene single crystals using selective self-seeding vertical Bridgman technique (SSVBT) and its characterization, Crystal Growth, 2005, 282, 370-375, which reference is incorporated herein in its entirety for all purposes). Pentacene doping concentrations were preferentially chosen close to saturation (on the order of 10 ppm to 100 ppm) to maximize the triplet-DNP buildup rates.

For the polarization transfer experiments, a sample was cut to approximately 40 mg with identification of the crystalline axes by optical birefringence and put into a home-built polarizer which featured cooling by liquid nitrogen to temperatures around 150° C. Control, readout, and analysis of the polarizer was performed with the software suite Qudi. The sample was rotated to its canonical orientation ($B_0$ magnetic field parallel to the pentacene X-axis) and shuttled between an electron spin resonance (ESR) cavity and an NMR coil both immersed in a field of an electromagnet which was typically maintained at 0.22 T for ESR/DNP operation and ramped up to 0.8 T for NMR readout. The crystal was aligned based on optically detected magnetic resonance (ODMR) of the pentacene fluorescence signal with an optical pump-probe scheme. Photoexcited triplet states were initialized with a pulsed laser and microwaves were synthesized by an arbitrary waveform generator (AWG), allowing the performance of advanced DNP protocols with microwave sweeps of frequency and phase.

An optimal-control enhanced transfer scheme was used to build up polarization, where the initial guess of the optimization algorithm was a 'standard' integrated solid effect (as described in A. Henstra et al, "Enhanced dynamic nuclear polarization by the integrated solid effect," *Physics Letters A,* 1988, 134, 134-136, which reference is incorporated herein in its entirety for all purposes). The optimized sequence reached polarization buildup rates ranging typically between 0.1% per minute and 1% per minute (dependent on doping concentration and sample thickness) and levelled of between 20 and 25% on average for 40 mg samples (assumed to be inhomogeneously polarized along the laser direction due to a high absorption cross section). The hyperpolarization value of naphthalene was calibrated by comparison to a thermally relaxed polarization signal.

Thermal NMR Measurements

In the experiments described herein, two benchtop spectrometers were utilized. One was included in the polarization transfer setup (1.45 T) to monitor polarization transfer and thermal calibration, and one was used to perform saturation transfer measurements to gauge cross-relaxation rates (1.88 T). Intermolecular NOE enhancements were obtained via a difference measurement where the enhanced signal was compared to a reference signal acquired with the same pulse sequence but with the saturation frequency set at an equal offset opposite to the target resonance.

Polarization Transfer to Target Compounds

In order to bring the polarization source in contact with the target compounds of choice, a polarized crystal was transported via a handheld magnet assembly ($B_0$ approximately 150 mT) from the optical polarizer to a ceramic crushing and mixing vessel. The crystal rested on a titanium frit with pore size on the order of 5 μm. In order to maximize the polarization transfer efficiency, the average distance between the source and target compounds should be reduced as much as possible. Therefore, naphthalene was dissolved in solution to a concentration 1.6 molar (M) to 1.8 M, which is not far from its saturation point in chloroform at room temperature. To achieve concentrations near 20% (v/v) naphthalene, approximately 160 µL of target solution were injected into the vessel.

The dissolution of the crystal was achieved by lowering a motor-controlled ceramic shaft into the ceramic vessel. The crushing shaft began a motor-controlled rotation, first lowering onto the crystal until just above the frit, and then rotating in position to continue dissolution. Crushing and mixing occurred for 6 seconds until the majority of the polarized naphthalene crystal was dissolved.

The material was then pushed through the titanium frit and injected over the course of 2 to 8 seconds to a 3 mm NMR tube positioned into a benchtop NMR spectrometer for monitoring the hyperpolarized signals over time. The hyperpolarized signals were monitored with small flip hard pulse excitations typically of 1 degree to 3 degrees to minimize effects of radiation damping, while still providing adequate SNR of the lower concentration target compound signals. Pulses were spaced either by 1.7 or 3.3 second acquisition periods.

In the experiments described herein, the following target solutions were used: (1) 100 millimolar (mM) propargyl acetate (Sigma Aldrich) in 99.8% D $CDCl_3$, (2) 50 mM TCE in 99.8% D $CDCl_3$, or a mixture of small molecules, (3) 25 mM acetone, 100 mM dichloromethane, 160 mM chloroform, 100 mM THF, 100 mM TCE in 99.8% D $CDCl_3$. Each target solution was bubbled with $N_2$ gas for 120 s before each experiment to expel any paramagnetic $O_2$ in order to minimize sources of nuclear spin auto-relaxation. An inert atmosphere of $N_2$ gas was also maintained during the process of crushing and dissolving the crystal, and pressurized $N_2$ gas was used to inject the hyperpolarized mixture to the NMR spectrometer.

Results and Analysis

FIG. 14 shows a series of NMR spectra acquired every 3.3 s (i.e., every three scans are shown, for clarity) following injection of the hyperpolarized solution into the spectrometer. Three traces are called out: trace 1410, trace 1420, and trace 1430. The sample considered in this example contained approximately 1.8 M naphthalene (20% v/v) and 100 mM dichloromethane in deuterated chloroform $CDCl_3$.

Figure 16B:
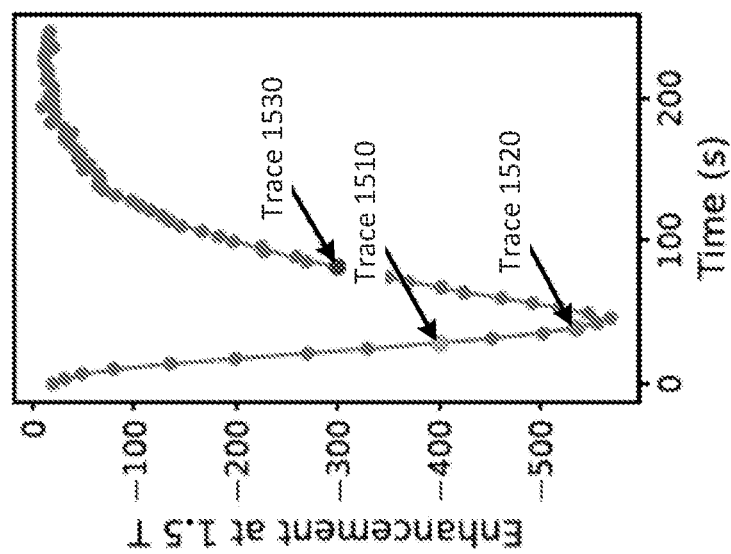
FIG. 16B depicts enhancement curves estimated for each proton site using the prior procedure, in accordance with disclosed embodiments.
Figure 16A:
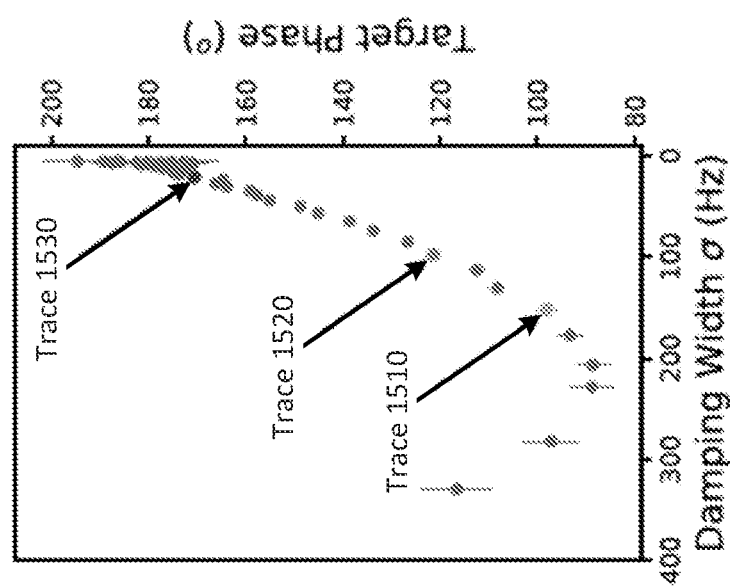
FIG. 16A depicts a relationship between a phase of a target resonance and a width of a radiation-damped signal, in accordance with disclosed embodiments.
Figure 17:
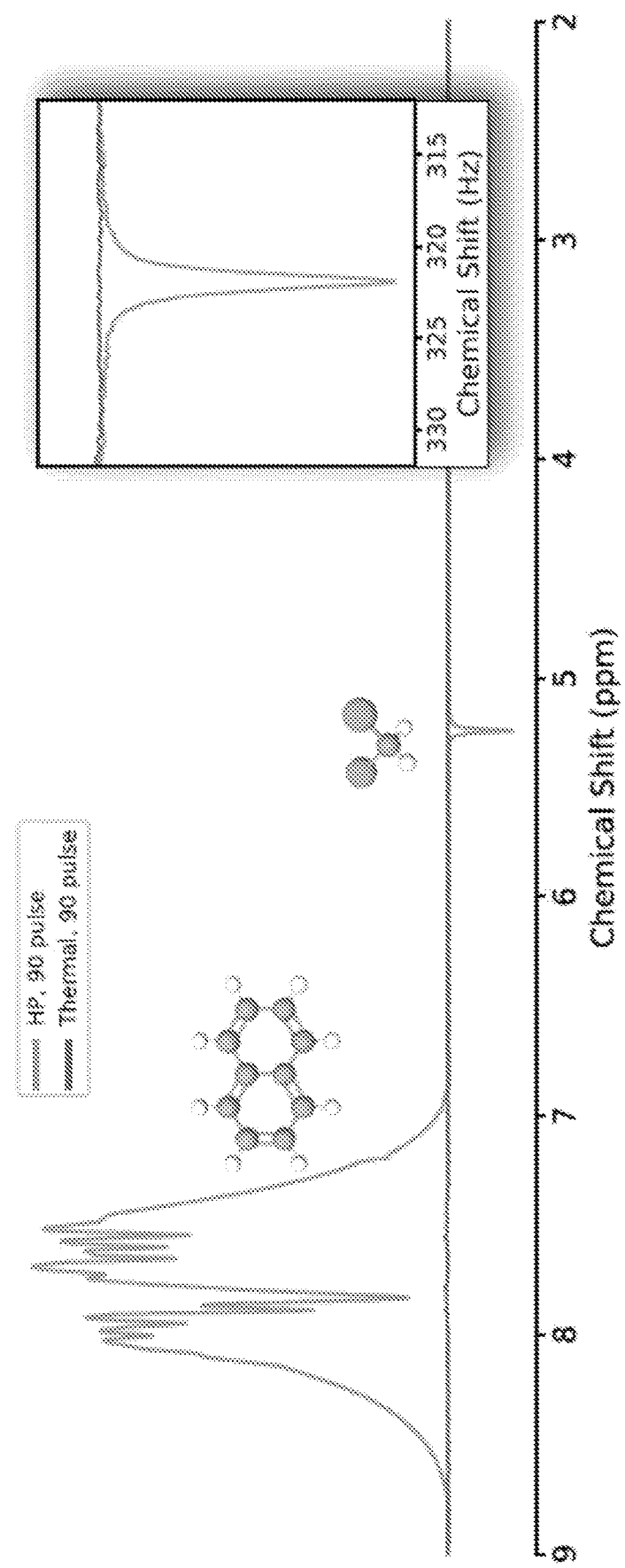
FIG. 17 depicts a spectrum acquired 35 s after injection into a spectrometer, as compared to an averaged, 90-degree flip angle thermal spectrum, in accordance with disclosed embodiments.

As described above with regards to FIG. 10C, the spectra show a number of features related to nuclear magnetization. First, the sample magnetic field produced a significant drift of the source compound and target compound resonances, shown clearly by the change in position of the dichloromethane and broadened naphthalene resonances over time. The magnetic field of the benchtop NMR spectrometer was 1.45 T, so a shift of −1.00 ppm corresponds to a 5.73% proton polarization. Second, the spectra are dominated by a large broad peak centered at the naphthalene resonance frequency. FIG. 16A depicts the relationship between the phase of the target resonance and the width of the radiation-damped signal. FIG. 16B depicts the enhancement curves estimated for each proton site using the prior procedure, in accordance with disclosed embodiments. FIG. 17 compares a 90-degree excitation of the hyperpolarized dichloromethane signal, measured after approximately 35 seconds and post-processed according to method 1000, to a single-shot thermal spectrum.

Figure 18A:
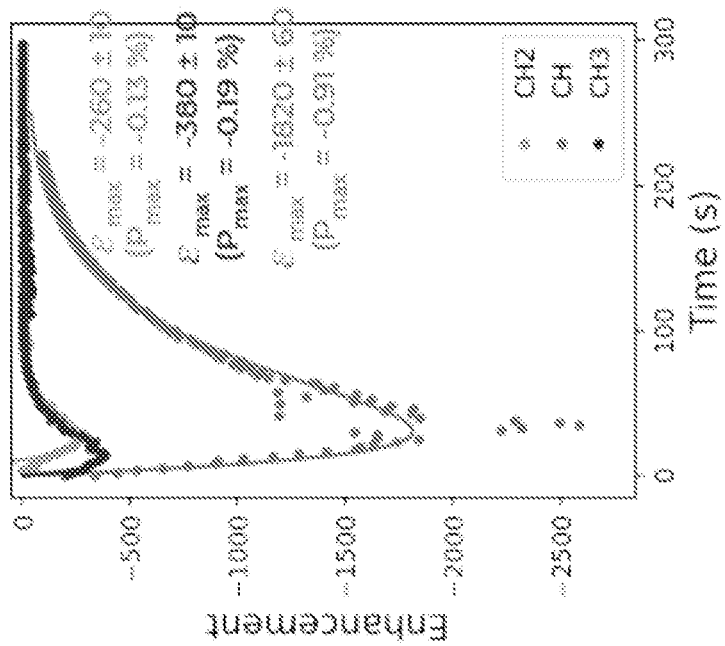
FIG. 18A depicts buildup curves, probed by 1 degree flip angles, for propargyl acetate, in accordance with disclosed embodiments.

The efficiency of the dissolution NOE polarization transfer approach was benchmarked using a mixture of 20% v/v naphthalene and 300 mM propargyl acetate in $CDCl_3$. The propargyl acetate spectrum consisted of three different proton resonances, all well separated from the naphthalene resonances. The buildup curves, probed by 1 degree flip angles are shown in FIG. 18A. These curves show the highest enhancement achieved for propargyl acetate, estimated to be a factor of −1730±60 at 1.45 T, which corresponds to −1% polarization. The CH protons exhibit a long $^1H$ $T_1$ relaxation time of about 60 s, resulting in a particularly high degree of polarization transfer, as expected from Equation (2). The $CH_2$ and $CH_3$ resonances both have $^1H$ Tis of approximately 10 seconds, and reach maximum signal enhancements of −250±10 and −360±10, respectively.

Figure 18B:
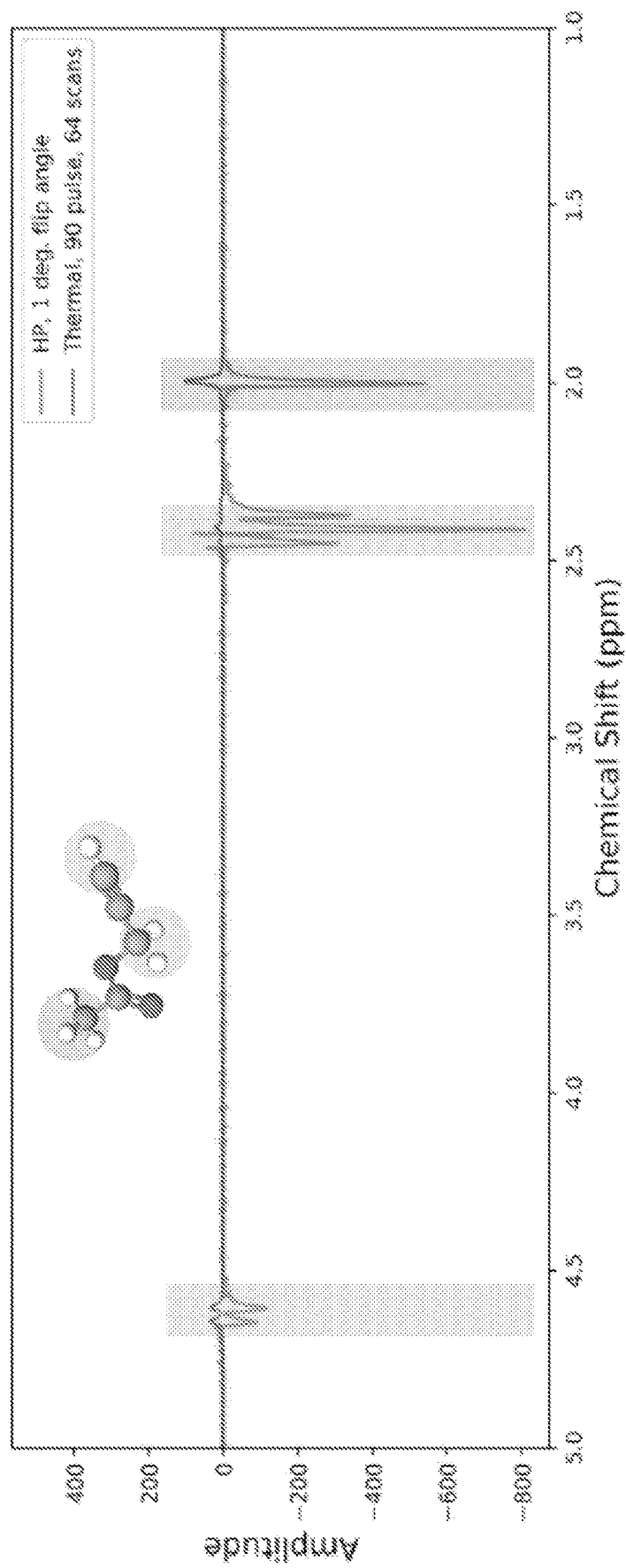
FIG. 18B depicts a hyperpolarized spectrum for propargyl acetate, compared to an averaged, 90 degree flip angle thermal spectrum, in accordance with disclosed embodiments.

The hyperpolarized spectrum is compared to an averaged, 90-degree flip angle thermal spectrum in FIG. 18B. The buildup time chosen for this comparison was approximately the time observed to show the maximum enhancement of the —CH resonance (e.g., 35 to 40 seconds). These curves show the highest enhancement achieved from propargyl acetate, estimated to be a factor of 1820±60 at 1.45 T, which corresponds to approximately 1% polarization. The CH protons exhibited a long proton $T_1$ relaxation time of about 60 seconds, resulting in a particularly high degree of polarization transfer. The $CH_2$ and $CH_3$ resonances both had proton $T_1$ times of approximately 10 seconds, and reached maximum signal enhancements of approximately 260±10 and 380±10, respectively.

Figure 18C:
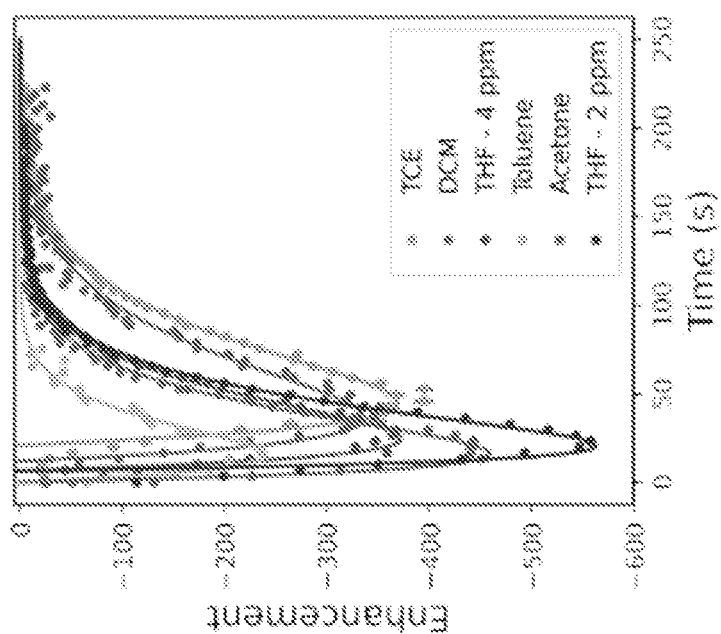
FIG. 18C depicts polarization enhancement over time for a solution including TCE, dichloromethane (DCM), tetrahydrofuran (THF), and acetone, in accordance with disclosed embodiments.
Figure 18D:
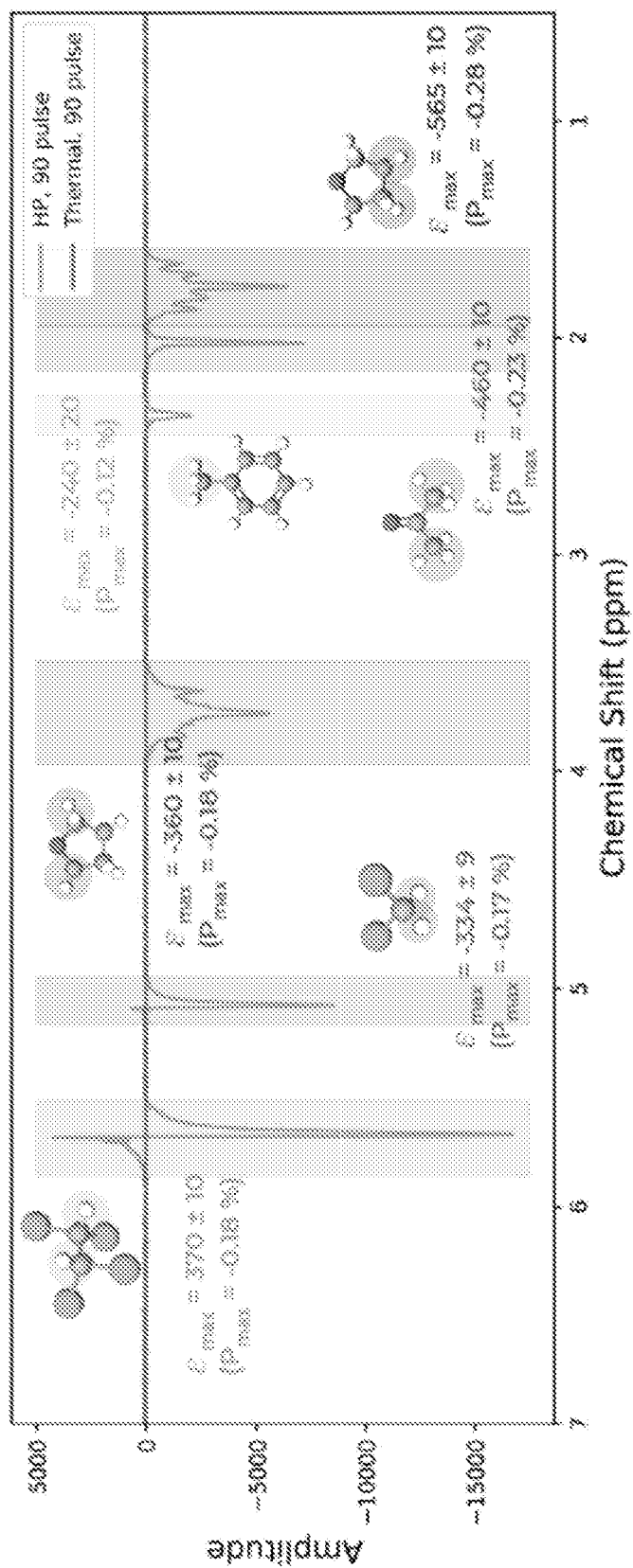
FIG. 18D depicts a hyperpolarized spectrum for the solution of FIG. 18C, compared to an averaged, 90 degree flip angle thermal spectrum, in accordance with disclosed embodiments.

In order to demonstrate applicability of the polarization transfer method for more complex NMR spectra, the procedure was applied to a $CDCl_3$ solution containing 100 mM 1,1,2,2-tetrachloroethane (TCE), 100 mM dichloromethane (DCM), 100 mM tetrahydrofuran (THF), 5-10 mM toluene and 25 mM acetone. Polarization enhancement over time for this solution is shown in FIG. 18C. The hyperpolarized spectrum is compared to an averaged, 90-degree flip angle thermal spectrum in FIG. 18D. Signal enhancements greater than 200 times relative to thermal polarization at 1.45 T were observed for all resonances, between 20 and 40 seconds after injection.

Exemplary Polarization Transfer from Phip-Polarized Diethyl Maleate in Solution

Transfer of polarization to target compounds via the intermolecular nuclear Overhauser effect (NOE) from spin-polarized deuterated and $^{13}C$-labeled diethyl maleate-1-$^{13}C$-$d_{10}$ dissolved in solution was investigated at room temperature and 1.9 T). NMR signals were enhanced by a factor of approximately 6 for ethyl acetate in solution A 0.5 mL sample of 2 M diethyl acetylene dicarboxylate-1-$^{13}C$-$d_{10}$ and 15 mM [1,4-bis(diphenylphosphino)butane](1,5-cyclooctadiene)rhodium(I) tetrafluoroborate was prepared in acetone-$d_6$. 25 µL ethyl acetate was added to the PHIP precursor solution. A pressurizable 5 mm NMR tube was filled with the solution and sealed, with a glass capillary extending to the bottom. The solution was heated to 60° C. and parahydrogen gas was bubbled through the capillary into the solution at 15 bar for 15 s. The chemical reaction caused hydrogenation of the precursor to diethyl maleate-1-$^{13}C$-$d_{10}$. Immediately afterwards, the NMR tube containing the solution was placed in a mu metal shield inside a solenoid electromagnet providing a constant 50 µT magnetic field. A transverse oscillating magnetic field was applied and ramped in intensity to convert the proton singlet order on the diethyl maleate-1-$^{13}C$-$d_{10}$ into proton magnetization. The sample was extracted from the mu metal shield and placed into a 1.9 T benchtop NMR spectrometer for signal acquisition following a 2° flip-angle rf pulse.

Results and Analysis

The diethyl maleate-1-$^{13}$C-$d_{10}$ showed a large, broad resonance at 6.5 ppm, and the ethyl acetate exhibited enhanced NMR resonances centered at 1.3, 2.0 and 4.1 ppm, corresponding to the three proton sites. FIG. 19 depicts hyperpolarized spectrum 1910, above a thermal-equilibrium spectrum 1920 acquired following a 90° flip-angle pulse after the hyperpolarized signals had relaxed. The ethyl acetate lines in the hyperpolarized spectrum are negatively enhanced, as is expected from the NOE effect.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

The embodiments may further be described using the following clauses:

1. A method for increasing a nuclear spin polarization of a target compound, comprising: (a) imparting a first non-thermal equilibrium nuclear spin polarization of at least 1% to at least one source atom of a source compound, the source atom having a nuclear gyromagnetic ratio of at least 12 megahertz per tesla (MHz/T); (b) obtaining a first solution comprising: the source compound, wherein the at least one source atom is present at a source concentration of at least 0.1 molar (M) in the first solution; and the target compound; and (c) imparting a second non-thermal equilibrium nuclear spin polarization of at least 0.01% to at least one target atom of the target compound via a nuclear Overhauser effect (NOE) transfer of the first non-thermal equilibrium nuclear spin polarization to the at least one target atom.

2. The method of clause 1, further comprising, prior to (b), placing the source compound in the first solution.
3. The method of clause 1 or 2, further comprising, prior to (b), placing the target compound in the first solution.
4. The method of any one of clauses 1-3, wherein (a) occurs prior to (b).
5. The method of any one of clauses 1-3, wherein (a) occurs subsequent to (b).
6. The method of any one of clauses 1-5, further comprising (d) extracting the target compound from the first solution and placing the target compound in a second solution.
7. The method of clause 6, wherein (d) comprises performing a liquid-liquid extraction procedure using the first solution and the second solution.
8. The method of clause 6, wherein (d) comprises crystallizing the target compound from the first solution and placing the target compound in the second solution.
9. The method of any one of clauses 1-8, further comprising performing at least one nuclear magnetic resonance (NMR) or magnetic resonance imaging (MRI) pulse sequence on the target compound.
10. The method of clause 9, wherein the at least one NMR or MM pulse sequence comprises at least one radiation-damping procedure configured to reduce radiation damping of the target compound by at least 50%, 60%, 70%, 80%, 90%, 95%, or 99% compared to a pulse sequence that does not utilize the at least one radiation-damping procedure.
11. The method of clause 10, wherein the at least one radiation-damping procedure comprises at least one Q-switching procedure or at least one detuning procedure.
12. The method of clause 11, wherein the at least one Q-switching procedure or the at least one detuning procedure is applied to an induction coil configured to receive an NMR signal or an MRI signal from the target compound.
13. The method of clause 12, wherein the at least one Q-switching procedure or the at least one detuning procedure comprises modifying a quality (Q) factor of the induction coil from: (i) a first value of at least 20 during application of a hard excitation pulse to the molecule to (ii) a second value of at most 1 during application of a frequency-selective pulse to the molecule.
14. The method of any one of clauses 1-13, wherein the source compound comprises at least one photoexcited triplet state (PETS) moiety.
15. The method of clause 14, wherein (a) comprises optically exciting a triplet state of the PETS moiety.
16. The method of any one of clauses 1-15, wherein the source compound comprises a crystalline host doped with a dopant.
17. The method of clause 16, wherein the crystalline host comprises naphthalene, p-terphenyl, or benzoic acid.
18. The method of clause 16 or 17, wherein the dopant comprises pentacene.
19. The method of any one of clauses 1-18, wherein the source compound comprises a parahydrogenated or paratriated source compound.
20. The method of clause 19, wherein the source compound comprises a PHIP-polarized parahydrogenated or paratritiated source compound.
21. The method of clause 19, wherein the source compound comprises a PHIP-SAH-polarized parahydrogenated or paratritiated source compound.

22. The method of clause 19, wherein the source compound comprises a SABRE-polarized parahydrogenated or paratriated source compound.
23. The method of clause 19, further comprising repeating (a) and to impart additional polarization to the target compound.
24. The method of any one of clauses 1-22, wherein the at least one source atom comprises hydrogen, tritium, fluorine-19, or phosphorus-31.
25. The method of any one of clauses 1-24, wherein the at least one target atom has a nuclear spin equal to ½.
26. The method of clause 25, wherein the at least one target atom comprises hydrogen, tritium, carbon-13, nitrogen-15, fluorine-19, silicon-29, phosphorous-31, iron-57, selenium-77, yttrium-89, rhodium-103, silver-107, silver-109, cadmium-111, cadmium-113, tin-117, tin-119, tellurium-123, tellurium-125, thullium-169, ytterbium-171, tungsten-183, osmium-187, platinum-195, mercury-199, thallium-203, thallium-205, lead-207, polonium-209, or plutonium-239.
27. The method of any one of clauses 1-26, wherein the at least one target atom has a nuclear spin greater than ½.
28. The method of clause 27, wherein the at least one target atom comprises deuterium, lithium-6, lithium-7, beryllium-9, boron-10, boron-11, nitrogen-14, oxygen-17, sodium-23, magnesium-25, aluminum-27, sulfur-33, chlorine-35, chlorine-37, potassium-39, potassium-41, calcium-43, scandium-45, titanium-47, titanium-49, vanadium-50, vanadium-51, chromium-53, manganese-55, cobalt-59, nickel-61, copper-63, copper-65, zinc-67, gallium-69, gallium-71, germanium-73, arsenic-75, bromine-79, bromine-81, rubidium-85, rubidium-87, strontium-87, zirconium-91, niobium-93, molybdenum-95, molybdenum-97, ruthenium-99, ruthenium-101, palladium-105, indium-113, indium-115, antimony-121, antimony-123, iodine-127, cesium-133, barium-135, barium-137, lanthanum-138, lanthanum-139, hafnium-177, hafnium-179, tantalum-181, rhenium-185, rhenium-187, osmium-189, iridium-191, iridium-193, gold-197, mercury-201, bismuth-209, or uranium-235.
29. The method of any one of clauses 1-28, wherein the at least one source atom is present at a source concentration of at least 0.2 M, 0.5 M, 1 M, 2 M, 5M, or 10 M in the first solution.
30. The method of any one of clauses 1-29, wherein (a) comprises imparting a first non-thermal equilibrium nuclear spin polarization of at least 2%, 5%, 10%, 20%, or 50% to the at least one source atom of the source compound.
31. The method of any one of clauses 1-30, wherein (c) comprises imparting a second non-thermal equilibrium nuclear spin polarization of at least 0.02%, 0.05%, 0.1%, 0.2%, 0.5%, 1%, 2%, 5%, or 10% to the at least one target atom of the target compound.
32. The method of any one of clauses 1-31, wherein a cross-relaxation term between the source atom and the at least one target atom is at most 1 Hertz (Hz), 0.5 Hz, 0.2 Hz, 0.1 Hz, 0.05 Hz, 0.02 Hz, 0.01 Hz, 0.005 Hz, 0.002 Hz, or 0.001 Hz.
33. The method of any one of clauses 1-32, wherein the target compound is present at a target concentration of at most 1,000 millimolar (mM), 500 mM, 200 mM, 100 mM, 50 mM, 20 mM, 10 mM, 5 mM, 2 mM, 1 mM, 500 micromolar (μM), 200 μM, 100 μM, 50 μM, 20 μM, 10 μM, 5 μM, 2 μM, 1 μM, 500 nanomolar (nM), 200 nM, 100 nM, 50 nM, 20 nM, 10 nM, 5 nM, 2 nM, 1 nM, or less in the first solution.
34. The method of any one of clauses 1-33, wherein the target compound is incorporated in a surface, solid, membrane, nanoparticle, or microparticle.
35. The method of any one of clauses 1-34, wherein the target compound comprises a small molecule, a peptide, a polypeptide, a protein, a nucleic acid, a ribonucleic acid, a deoxyribonucleic acid, a carbohydrate, or a polymer.
36. A system for increasing a nuclear spin polarization of a target compound, comprising: a first solution receiving module configured to receive a first solution comprising: a source compound dissolved therein, the source compound comprising at least one source atom, the at least one source non-carbon atom present at a source concentration of at least 0.1 molar (M) in the first solution; a polarization module coupled to the first solution receiving module, the polarization module configured to impart a first non-thermal equilibrium nuclear spin polarization of at least 1% to the at least one source atom of the source compound; a second solution receiving module configured to receive a second solution comprising: the target compound dissolved therein; and a mixing module fluidically coupled to the polarization module and to the second solution receiving module, the mixing module configured to mix the first solution and the second solution to thereby permit transfer of the first non-thermal equilibrium nuclear spin polarization to at least one target atom of the target compound via nuclear Overhauser effect (NOE) transfer, thereby imparting a second non-thermal equilibrium nuclear spin polarization of at least 0.01% to the at least one target atom of the target compound.
37. The system of clause 36, further comprising a chamber fluidically coupled to the first solution receiving module, the chamber configured to receive the source compound and a liquid and to mix the source compound and the liquid to thereby form the first solution.
38. The system of clause 36 or 37, wherein the polarization module comprises a parahydrogen polarization module.
39. The system of clause 36 or 37, wherein the polarization module comprises a PETS module.
40. The system of any one of clauses 36-39, wherein the system is further configured to implement the method of any one of clauses 1-35.
41. A system for increasing a nuclear spin polarization of a target compound, comprising: a container comprising: an internal volume configured to house a source compound comprising at least one PETS moiety therein; a first magnetic field source at least partially surrounding the internal volume and configured to generate a first magnetic field within the internal volume; at least one optical window configured to couple to a light source to thereby permit optical polarization of the at least one PETS moiety; and at least one container port configured to permit passage of the source compound therethrough; and a solution preparation system comprising: a dissolution vessel configured to couple to the at least one container port, to receive the source compound following passage of the source compound through the at least one container port, and to receive a pressurized gas and a first solution comprising the compound dissolved therein; a second magnetic field source at least partially surrounding the dissolution vessel and configured to generate a second magnetic field within the dissolution vessel; a crushing head located within the dissolution vessel and configured to crush the source compound to thereby permit dissolution of the source compound in the first solution to thereby generate a second solution; and at least one solution port configured to permit passage of the second solution therethrough.

42. The system of clause 41, wherein the source compound comprises a crystalline host doped with a dopant.

43. The system of clause 42, wherein the crystalline host comprises naphthalene, p-terphenyl, or benzoic acid.

44. The system of clause 42 or 43, wherein the dopant comprises pentacene.

45. The system of any one of clauses 41-44, wherein the first magnetic field source or the second magnetic field source comprises at least one solenoid.

46. The system of any one of clauses 41-45, wherein the first magnetic field or the second magnetic field has a strength of at least about 1 mT, 2 mT, 5 mT, or 10 mT.

47. The system of any one of clauses 41-46, wherein the first magnetic field or the second magnetic field has a strength of at most about 5000 mT, 2000 mT, 1000 mT, 500 mT, 200 mT, or 100 mT.

48. The system of any one of clauses 41-47, wherein the pressurized gas comprises nitrogen, argon, or any combination thereof.

49. The system of any one of clauses 41-48, further comprising a shaft mechanically coupled to the crushing head and configured to permit motion of the crushing head to thereby crush the source compound.

50. The system of clause 49, further comprising a rotary motor mechanically coupled to the shaft and configured to provide the motion to the crushing head via the shaft to thereby crush the source compound.

51. The system of any one of clauses 41-50, wherein the solution port is configured to couple to an NMR tube configured to receive the second solution therein.

52. The system of any one of clauses 41-51, wherein the solution port is configured to couple to a flow system configured to receive the second solution and to transport the second solution to an NMR tube located within an NMR spectrometer.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

What is claimed is:

1. A method for increasing a nuclear spin polarization of a target compound, comprising:
   (a) imparting a first non-thermal equilibrium nuclear spin polarization of at least 1% to at least one source atom of a source compound, the source atom having a nuclear gyromagnetic ratio of at least 12 megahertz per tesla (MHz/T);
   (b) obtaining a first solution comprising: the source compound, wherein the at least one source atom is present at a source concentration of at least 0.1 molar (M) in the first solution; and the target compound; and
   (c) imparting a second non-thermal equilibrium nuclear spin polarization of at least 0.01% to at least one target atom of the target compound via an intermolecular nuclear Overhauser effect (NOE) transfer of the first non-thermal equilibrium nuclear spin polarization to the at least one target atom.

2. The method of claim 1, further comprising, prior to (b), placing the source compound in the first solution.

3. The method of claim 1, further comprising, prior to (b), placing the target compound in the first solution.

4. The method of claim 1, wherein (a) occurs prior to (b).

5. The method of claim 1, wherein (a) occurs subsequent to (b).

6. The method of claim 1, further comprising (d) extracting the target compound from the first solution and placing the target compound in a second solution.

7. The method of claim 6, wherein (d) comprises performing a liquid-liquid extraction procedure using the first solution and the second solution.

8. The method of claim 6, wherein (d) comprises crystallizing the target compound from the first solution and placing the target compound in the second solution.

9. The method of claim 1, wherein:
   the method further comprises performing at least one nuclear magnetic resonance (NMR) or magnetic resonance imaging (MRI) pulse sequence on the target compound; and
   the at least one NMR or MRI pulse sequence comprises at least one radiation-damping procedure configured to reduce radiation damping of the target compound by at least 50% as compared to a pulse sequence that does not utilize the at least one radiation-damping procedure.

10. The method of claim 9, wherein the at least one radiation-damping procedure comprises at least one Q-switching procedure or at least one detuning procedure.

11. The method of claim 10, wherein the at least one Q-switching procedure or the at least one detuning procedure is applied to an induction coil configured to receive an NMR signal or an MRI signal from the target compound.

12. The method of claim 11, wherein the at least one Q-switching procedure or the at least one detuning procedure comprises modifying a quality (Q) factor of the induction coil from: (i) a first value of at least 20 during application of a hard excitation pulse to the molecule to (ii) a second value of at most 1 during application of a frequency-selective pulse to the molecule.

13. The method of claim 1, wherein the source compound comprises at least one photoexcited triplet state (PETS) moiety.

14. The method of claim 13, wherein (a) comprises optically exciting a triplet state of the PETS moiety.

15. The method of claim 1, wherein the source compound comprises a crystalline host doped with a dopant.

16. The method of claim 15, wherein the crystalline host comprises naphthalene, p-terphenyl, or benzoic acid.

17. The method of claim 15, wherein the dopant comprises pentacene.

18. The method of claim 1, wherein the source compound comprises a parahydrogenated or paratritiated source compound.

19. The method of claim 18, wherein the source compound comprises:
   a PHIP-polarized parahydrogenated or paratritiated source compound,
   a PHIP-SAH-polarized parahydrogenated or paratritiated source compound, or a SABRE-polarized parahydrogenated or paratritiated source compound.

20. The method of claim 1, further comprising repeating (a) and (c) to impart additional polarization to the target compound.

21. The method of claim 1, wherein the at least one source atom comprises hydrogen, tritium, fluorine-19, or phosphorus-31.

22. The method of claim 1, wherein the at least one target atom has a nuclear spin equal to ½.

23. The method of claim 22, wherein the at least one target atom comprises hydrogen, tritium, carbon-13, nitrogen-15, fluorine-19, silicon-29, phosphorous-31, iron-57, selenium-77, yttrium-89, rhodium-103, silver-107, silver-109, cadmium-111, cadmium-113, tin-117, tin-119, tellurium-123, tellurium-125, thullium-169, ytterbium-171, tungsten-183, osmium-187, platinum-195, mercury-199, thallium-203, thallium-205, lead-207, polonium-209, or plutonium-239.

24. The method of claim 1, wherein the at least one target atom has a nuclear spin greater than ½.

25. The method of claim 24, wherein the at least one target atom comprises deuterium, lithium-6, lithium-7, beryllium-9, boron-10, boron-11, nitrogen-14, oxygen-17, sodium-23, magnesium-25, aluminum-27, sulfur-33, chlorine-35, chlorine-37, potassium-39, potassium-41, calcium-43, scandium-45, titanium-47, titanium-49, vanadium-50, vanadium-51, chromium-53, manganese-55, cobalt-59, nickel-61, copper-63, copper-65, zinc-67, gallium-69, gallium-71, germanium-73, arsenic-75, bromine-79, bromine-81, rubidium-85, rubidium-87, strontium-87, zirconium-91, niobium-93, molybdenum-95, molybdenum-97, ruthenium-99, ruthenium-101, palladium-105, indium-113, indium-115, antimony-121, antimony-123, iodine-127, cesium-133, barium-135, barium-137, lanthanum-138, lanthanum-139, hafnium-177, hafnium-179, tantalum-181, rhenium-185, rhenium-187, osmium-189, iridium-191, iridium-193, gold-197, mercury-201, bismuth-209, or uranium-235.

26. The method of claim 1, wherein the at least one source atom is present at a source concentration of at least 1 M in the first solution.

27. The method of claim 1, wherein (a) comprises imparting a first non-thermal equilibrium nuclear spin polarization of at least 2% to the at least one source atom of the source compound.

28. The method of claim 1, wherein (c) comprises imparting a second non-thermal equilibrium nuclear spin polarization of at least 1% to the at least one target atom of the target compound.

29. The method of claim 1, wherein a cross-relaxation term between the source atom and the at least one target atom is at most 1 Hertz (Hz).

30. The method of claim 1, wherein the target compound is present at a target concentration of at most 1,000 millimolar (mM) in the first solution.

* * * * *